(12) United States Patent
Gatignol et al.

(10) Patent No.: US 9,932,364 B2
(45) Date of Patent: Apr. 3, 2018

(54) ANTISENSE-BASED SMALL RNA AGENTS TARGETING THE GAG OPEN READING FRAME OF HIV-1 RNA

(71) Applicant: THE ROYAL INSTITUTION FOR THE ADVANCEMENT OF LEARNING/MCGILL UNIVERSITY, Montreal (CA)

(72) Inventors: Anne Gatignol, Montreal (CA); Robert Scarborough, Montreal (CA)

(73) Assignee: The Royal Institution for the Advancement of Learning/McGill University, Montreal (CA)

( * ) Notice: Subject to any disclaimer, the term of this patent is extended or adjusted under 35 U.S.C. 154(b) by 0 days.

(21) Appl. No.: 14/912,100

(22) PCT Filed: Aug. 25, 2014

(86) PCT No.: PCT/CA2014/050814
§ 371 (c)(1),
(2) Date: Feb. 15, 2016

(87) PCT Pub. No.: WO2015/027334
PCT Pub. Date: Mar. 5, 2015

(65) Prior Publication Data
US 2016/0201061 A1   Jul. 14, 2016

Related U.S. Application Data

(60) Provisional application No. 61/869,852, filed on Aug. 26, 2013.

(51) Int. Cl.
*C07H 21/04* (2006.01)
*C07H 21/02* (2006.01)
*C12N 15/113* (2010.01)

(52) U.S. Cl.
CPC ......... *C07H 21/02* (2013.01); *C12N 15/1132* (2013.01); *C12N 2310/11* (2013.01); *C12N 2310/12* (2013.01); *C12N 2310/14* (2013.01); *C12N 2310/531* (2013.01)

(58) Field of Classification Search
None
See application file for complete search history.

(56) References Cited

U.S. PATENT DOCUMENTS 8,008,472 B2 *  8/2011  McSwiggen ....... C12N 15/1132
                                              514/44 A

FOREIGN PATENT DOCUMENTS

| CN | 102352360 A | 11/2011 |
| WO | WO 94/08004 | 4/1994 |
| WO | WO 97/46673 | 12/1997 |
| WO | WO 06/023491 | 3/2006 |
| WO | PCT/CA2014/050814 | 11/2014 |

OTHER PUBLICATIONS

And McIntyre et al. (BMC Biotechnology 2006, 6:1 pp. 1-8).*
Altschul et al., Gapped BLAST and PSI-BLAST: a new generation of protein database search programs, Nucleic Acids Res 25: 3389-402, 1997.
Amarzguioui et al., Tolerance for mutations and chemical modifications in a siRNA, Nucleic Acids Res 31:589-595, 2003.
Amarzguioui et al., Rational design and in vitro and in vivo delivery of Dicer substrate siRNA. Nat Protoc 1:508-517, 2006.
Asif-Ullah et al., Development of ribozyme-based gene-inactivations; the example of the hepatitis delta virus ribozyme. Curr Gene Ther 7: 205-16, 2007.
Bennett et al., Gene therapy strategies for HIV/AIDS: Preclinical modeling in humanized mice, Viruses 5:3119-3141, 2013.
Bergeron et al., Target-dependent on/off switch increases ribozyme fidelity. Nucleic Acids Res 33: 1240-8, 2005.
Bergeron et al., Functional characterization of the SOFA delta ribozyme. RNA 11: 1858-68, 2005.
Bramlage et al., HIV-1 LTR as a target for synthetic ribozyme-mediated inhibition of gene expression: site selection and inhibition in cell culture. Nucleic Acids Res 28: 4059-67, 2000.
Brummelkamp et al., A system for stable expression of short interfering RNAs in mammalian cells. Science 296: 550-553, 2002.
Burnett et al., RNA-based therapeutics: current progress and future prospects. Chem Biol 19: 60-71, 2012.
Caplen et al., Specific inhibition of gene expression by small double-stranded RNAs in invertebrate and vertebrate systems. Proc Natl Acad Sci U S A 98:9742-9747, 2001.
Chang et al., Enhanced expression and HIV-1 inhibition of chimeric tRNA(Lys3)-ribozymes under dual U6 snRNA and tRNA promoters. Mol Ther 6: 481-9, 2002.
Chang et al., Asymmetric shorter-duplex siRNA structures trigger efficient gene silencing with reduced nonspecific effects, Mol Ther 17:725-732, 2009.
Chu et al., Potent RNAi by short RNA triggers, RNA 14:1714-1719, 2008.
Clerzius et al., The PKR activator, PACT, becomes a PKR inhibitor during HIV-1 replication. Retrovirology 10: 96, 2013.
Czauderna et al., Structural variations and stabilising modifications of synthetic siRNAs in mammalian cells. Nucleic Acids Res 31:2705-2716, 2003.
Daniels et al., Characterization of the TRBP domain required for Dicer interaction and function in RNA interference. BMC Mol Biol 10:38, 2009.
Daniels et al., The multiple functions of TRBP, at the hub of cell responses to viruses, stress, and cancer. Microbiol Mol Biol Rev 76:652-666, 2012.
D'Anjou et al., Molecular Validation of PACE4 as a Target in Prostate Cancer. Transl Oncol 4: 157-72, 2011.
De Clercq, Antiretroviral drugs. Curr Opin Pharmacol. 10:507-515, 2010.
DeYoung et al., A. Computer analysis of the conservation and uniqueness of ribozyme-targeted HIV sequences. Methods Mol Biol. 74:27-36, 1997.
DiGiusto et al., RNA-based gene therapy for HIV with lentiviral vector-modified CD34+ cells in patients undergoing transplantation for AIDS-related lymphoma. Sci Transl Med 2:36ra43, 2010.

(Continued)

*Primary Examiner* — Kimberly Chong
(74) *Attorney, Agent, or Firm* — Alain Dumont

(57) ABSTRACT

Antisense nucleic acid molecules, such as ribozymes, shRNA and siRNA, targeting the Gag region of HIV-1 open reading frame, and uses thereof for inhibiting HIV-1 replication and infection, are disclosed. The antisense nucleic acid molecules more specifically target a sequence corresponding to about nucleotide 1495 to about nucleotide 1526, or nucleotide 1497 to about nucleotide 1521, of HIV-1 clone pNL4-3.

17 Claims, 17 Drawing Sheets

(56) References Cited

OTHER PUBLICATIONS

Eekels et al., Toward a durable treatment of HIV-1 infection using RNA interference. Prog Mol Biol Transl Sci 102:141-163, 2011.
Elbashir et al., Duplexes of 21-nucleotide RNAs mediate RNA interference in cultured mammalian cells. Nature 411:494-498, 2001.
Elbashir et al., Functional anatomy of siRNAs for mediating efficient RNAi in Drosophilamelanogaster embryo lysate. EMBO J 20:6877-6888, 2001.
Fiola et al., Gene targeting in the Gram-Positive bacterium Lactococcus lactis, using various delta ribozymes. Appl Environ Microbiol 72: 869-79, 2006.
Fire A et al., Potent and specific genetic interference by double-stranded RNA in Caenorhabditis elegans. Nature 391:806-811, 1998.
Foster et al., Comprehensive evaluation of canonical versus Dicer-substrate siRNA in vitro and in vivo. RNA 18:557-568, 2012.
Gao et al., A comprehensive panel of near-full-length clones and reference sequences for non-subtype B isolates of human immunodeficiency virus type 1. J Virol 72: 5680-98, 1998.
Good et al., Expression of small, therapeutic RNAs in human cell nuclei. Gene Ther 4: 45-54, 1997.
Haasnoot et al., Nucleic acids-based therapeutics in the battle against pathogenic viruses. Handb Exp Pharmacol: 243-63, 2009.
Hemelaar et al., Global trends in molecular epidemiology of HIV-1 during 2000-2007. AIDS 25: 679-89, 2011.
Hoxie et al., Novel cell and gene therapies for HIV, Cold Spring Harb Perspect Med 2:a007179, 2012.
Kanasty et al., Delivery materials for siRNA therapeutics. Nat Mater 12:967-977, 2013.
Khvorova et al., Functional siRNAs and miRNAs exhibit strand bias, Cell 115:209-216, 2003.
Kim et al., Synthetic dsRNA Dicer substrates enhance RNAi potency and efficacy, Nat Biotechnol 23:222-226, 2005.
Kumar et al., T cell-specific siRNA delivery suppresses HIV-1 infection in humanized mice, Cell 134:577-586, 2008.
Kusagawa et al., Isolation and characterization of a full-length molecular DNA clone of Ghanaian HIV type 1 intersubtype A/G recombinant CRF02_AG, which is replication competent in a restricted host range., AIDS Res Hum Retroviruses;17:649-655, 2001.
Laine et al., In vitro and in vivo cleavage of HIV-1 RNA by new SOFA-HDV ribozymes and their potential to inhibit viral replication, RNA Biol 8: 343-53, 2011.
Lambeth et al., Short hairpin RNA-mediated gene silencing, Methods Mol Biol 942:205-232, 2013.
Le Douce, V., Janossy, A., Hallay, H., Ali, S., Riclet, R., Rohr, O. et al. (2012). Achieving a cure for HIV infection: do we have reasons to be optimistic, J Antimicrob Chemother 67: 1063-74.
Lee et al., Lentiviral delivery of short hairpin RNAs protects CD4 T cells from multiple clades and primary isolates of HIV, Blood 106: 818-26, 2005.
Lévesque et al., Investigating a new generation of ribozymes in order to target HCV, PLoS One 5: e9627, 2010.
Lévesque et al., Target-induced SOFA-HDV ribozyme, Methods Mol Biol 848: 369-84, 2012.
Li et al., Long-term inhibition of HIV-1 infection in primary hematopoietic cells by lentiviral vector delivery of a triple combination of anti-HIV shRNA, anti-CCR5 ribozyme, and a nucleolar-localizing TAR decoy, Mol Ther 12: 900-9, 2005.
Lucier et al., RiboSubstrates: a web application addressing the cleavage specificities of ribozymes in designated genomes, BMC Bioinformatics 7: 480, 2006.
Mandal et al., Excessive RNA splicing and inhibition of HIV-1 replication induced by modified U1 small nuclear RNAs. J Virol 84: 12790-800, 2010.
McIntyre et al., 96 shRNAs designed for maximal coverage of HIV-1 variants, Retrovirology 6:55, 2009.
McIntyre et al., The effects of stem length and core placement on shRNA activity. BMC Mol Biol 12:34, 2011.
Michienzi et al., Ribozyme-mediated inhibition of HIV 1 suggests nucleolar trafficking of HIV-1 RNA, Proc Natl Acad Sci U S A 97: 8955-60, 2000.
Mitsuyasu et al., Phase 2 gene therapy trial of an anti-HIV ribozyme in autologous CD34+ cells, Nat Med 15: 285-92, 2009.
Miyagishi et al., Optimization of an siRNA-expression system with an improved hairpin and its significant suppressive effects in mammalian cells, J Gene Med, 6:715-723, 2004.
Mochizuki et al., An infectious DNA clone of HIV type 1 subtype C, AIDS Res Hum Retroviruses 15: 1321-4, 1999.
Motard et al., A novel ribozyme-based prophylaxis inhibits influenza A virus replication and protects from severe disease, PLoS One 6: e27327, 2011.
Müller-Kuller et al., Identification and characterization of a highly efficient anti-HIV pol hammerhead ribozyme, Oligonucleotides 19: 265-72, 2009.
Naito et al., Optimal design and validation of antiviral siRNA for targeting HIV-1, Retrovirology 4: 80, 2007.
Ndungu et al., Construction and analysis of an infectious human Immunodeficiency virus type 1 subtype C molecular clone, J Virol 75: 4964-72, 2001.
Paddison et al., Short hairpin RNAs (shRNAs) induce sequence-specific silencing in mammalian cells, Genes Dev 16:948-958, 2002.
Peden et al., Changes in growth properties on passage in tissue culture of viruses derived from infectious molecular clones of HIV-1LAI, HIV-1MAL, and HIV-1ELI, Virology 185: 661-72, 1991.
Provost et al., Ribonuclease activity and RNA binding of recombinant human Dicer, EMBO J 21:5864-5874, 2002.
Puerta-Fernandez et al., Inhibition of HIV-1 replication by RNA targeted against the LTR region, AIDS 19: 863-70, 2005.
Reynolds et al., Induction of the interferon response by siRNA is cell type- and duplex length-dependent, RNA 12:988-993, 2006.
Riss et al., Cell viability assays. In Sittampalam GS, Gal-Edd N, Arkin M, Auld D, Austin C, Bejcek B, Glicksman M, Inglese J, Lemmon V, Li Z, McGee J, McManus O, Minor L, Napper A, Riss T, Trask OJ, Weidner J (ed), Assay guidance manual. Eli Lilly & Company and the National Center for Advancing Translational Sciences, Bethesda, MD, 2004.
Robichaud et al., Development of an isoform-specific gene suppression system: the study of the human Pax-5B transcriptional element, Nucleic Acids Res 36: 4609-20, 2008.
Rose et al., Functional polarity is introduced by Dicer processing of short substrate RNAs, Nucleic Acids Res 33:4140-4156, 2005.
Rossi et al., Ribozyme therapy for HIV infection, Adv Drug Deliv Rev 44: 71-8, 2000.
Rossi et al., Genetic therapies against HIV. Nat Biotechnol 25: 1444-54, 2007.
Sabariegos et al., Sequence homology required by human immunodeficiency virus type 1 to escape from short interfering RNAs, J Virol 80: 571-7, 2006.
Sajic et al., Use of modified U1 snRNAs to inhibit HIV-1 replication, Nucleic Acids Res 35: 247-55, 2007.
Sanchez-Luque et al., Inhibition of HIV-1 replication and dimerization interference by dual inhibitory RNAs, Molecules 15: 4757-72, 2010.
Sano et al., Effect of asymmetric terminal structures of short RNA duplexes on the RNA interference activity and strand selection, Nucleic Acids Res 36:5812-5821, 2008.
Scarborough et al., A conserved target site in HIV-1 Gag RNA is accessible to inhibition by both an HDV ribozyme and a short hairpin RNA. Mol Ther Nucleic Acids 3:e178, 2014.
Scarborough et al., Design and evaluation of clinically relevant SOFA-HDV ribozymes targeting HIV RNA, Methods Mol Biol 1103:31-43, 2014.
Scherer et al., Ex vivo gene therapy for HIV-1 treatment, Hum Mol Genet 20: R100-7, 2011.
Schwarz et al., Asymmetry in the assembly of the RNAi enzyme complex. Cell 115:199-208, 2003.
Siolas et al., Synthetic shRNAs as potent RNAi triggers, Nat Biotechnol 23:227-231, 2005.

(56) References Cited

OTHER PUBLICATIONS

Snead et al., RNA interference trigger variants: getting the most out of RNA for RNA interference-based therapeutics, Nucleic Acid Ther 22:139-146, 2012.
Snead et al., Molecular basis for improved gene silencing by Dicer substrate interfering RNA compared with other siRNA variants, Nucleic Acids Res 41:6209-6221, 2013.
Strapps et al., The siRNA sequence and guide strand overhangs are determinants of in vivo duration of silencing, Nucleic Acids Res 38:4788-4797, 2010.
Sun et al., Asymmetric RNA duplexes mediate RNA interference in mammalian cells, Nat Biotechnol 26:1379-1382, 2008.
ter Brake et al., Silencing of HIV-1 with RNA interference: a multiple shRNA approach, Mol Ther 14: 883-92, 2006.
Theodore et al., Construction and characterization of a stable full-length macrophage-tropic HIV type 1 molecular clone that directs the production of high titers of progeny virions, AIDS Res Hum Retroviruses 12: 191-4, 1996.
Tyagi et al., HIVsirDB: a database of HIV inhibiting siRNAs. PLoS One 6:e25917, 2011.
Unwalla et al., Use of a U16 snoRNA-containing ribozyme library to identify ribozyme targets in HIV-1. Mol Ther 16: 1113-9, 2008.
Waterhouse et al., Jalview Version 2—a multiple sequence alignment editor and analysis workbench, Bioinformatics 25:1189-91, 2009.
Watts et al., Architecture and secondary structure of an entire HIV-1 RNA genome, Nature 460: 711-6, 2009.
Whitehead et al., Silencing or stimulation? siRNA delivery and the immune system, Annu Rev Chem Biomol Eng 2:77-96, 2011.
Yu et al., Simultaneous inhibition of GSK3alpha and GSK3beta using hairpin siRNA expression vectors, Mol Ther 7:228-236, 2003.
Zeng et al., Effective Inhibition of Human Immunodeficiency Virus 1 Replication by Engineered RNase P Ribozyme, PLoS One 7:e51855, 2012.
Zhang et al., Human Dicer preferentially cleaves dsRNAs at their termini without a requirement for ATP, EMBO J 21:5875-5885, 2002.
Zhou et al., Systemic administration of combinatorial dsiRNAs via nanoparticles efficiently suppresses HIV-1 infection in humanized mice, Mol Ther 19:2228-2238, 2011.
Zhou et al., Deep sequencing analyses of DsiRNAs reveal the influence of 3' terminal over-hangs on dicing polarity, strand selectivity, and RNA editing of siRNAs, Mol Ther Nucleic Acids 1:e17, 2012.
Zhou et al., Functional in vivo delivery of multiplexed anti-HIV-1 siRNAs via a chemically synthesized aptamer with a sticky bridge, Mol Ther 21:192-200, 2013.

* cited by examiner

|  | -Rz1498 | -Rz1498Bs1 | -Rz1498Bs2 |
|---|---|---|---|
| Fmax +/- SE | 36.0 +/- 1.0 | 13.8 +/- 0.6 | 12.5 +/- 0.5 |
| Kobs +/- SE | 0.018 +/- 0.001 | 0.016 +/- 0.002 | 0.015 +/- 0.001 |

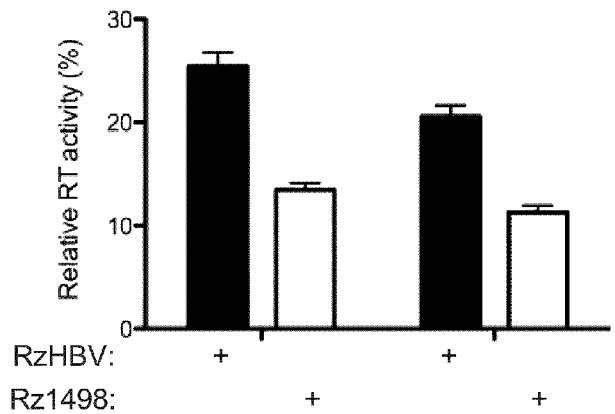
FIG. 5D
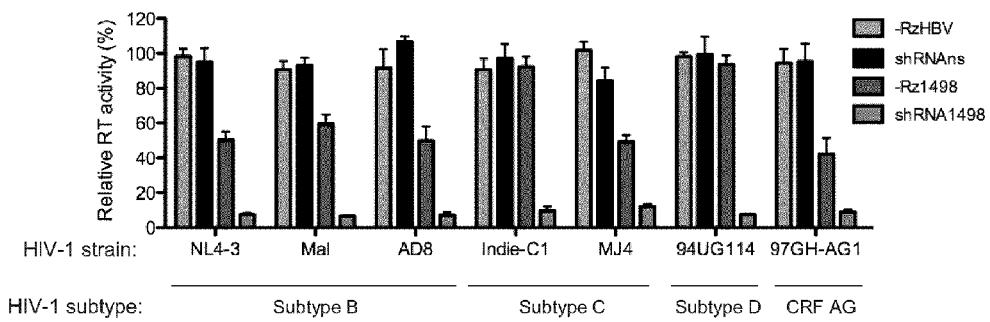
FIG. 6A
FIG. 6B

ACRI Human2 slides: 396619, 396612, 396615, 396521, 396694, 396688

Slides are a triplicate dye-swap (Green/Red) of Rz1498 vs psiRNA

Up-regulated in Rz1498 vs psiRNA     Total 25

| | log2 ratio | | | | | | | | Gene_Symbol | Target_NM | Log2 ratio ajusted (±) | | | | | | | | | | | |
|---|---|---|---|---|---|---|---|---|---|---|---|---|---|---|---|---|---|---|---|---|---|---|
| id | 396619 | 396615 | 396694 | 396612 | 396521 | 396688 | | | | | 396619 | 396615 | 396694 | 396612 | 396521 | 396688 | Mean (6) | SD | Mean (g) | SD | Mean (r) | SD |
| 17393 | -0.931 | -0.727 | -0.801 | 0.662 | 0.920 | 0.721 | | | ATXN2L | NM_148416 | 0.931 | 0.727 | 0.801 | 0.662 | 0.920 | 0.721 | 0.794 | 0.111 | 0.820 | 0.103 | 0.768 | 0.135 |
| 14991 | -0.873 | -0.807 | -0.843 | 0.692 | 1.023 | 0.620 | | | MID1IP1 | NM_021242 | 0.873 | 0.807 | 0.843 | 0.692 | 1.023 | 0.620 | 0.810 | 0.142 | 0.841 | 0.033 | 0.778 | 0.215 |
| 14906 | -0.819 | -0.439 | -0.556 | 0.398 | 0.584 | 0.150 | | | ATP11C | NM_173694 | 0.819 | 0.439 | 0.556 | 0.398 | 0.584 | 0.150 | 0.491 | 0.223 | 0.605 | 0.195 | 0.377 | 0.218 |
| 11719 | -0.789 | -0.885 | -0.746 | 0.307 | 0.572 | 0.216 | | | EI24 | JM_00100727 | 0.789 | 0.885 | 0.746 | 0.307 | 0.572 | 0.216 | 0.586 | 0.272 | 0.807 | 0.071 | 0.365 | 0.185 |
| 11504 | -0.747 | -0.708 | -0.919 | 0.505 | 0.411 | 0.634 | | | ACTB | NM_001101 | 0.747 | 0.708 | 0.919 | 0.505 | 0.411 | 0.634 | 0.654 | 0.181 | 0.791 | 0.112 | 0.517 | 0.112 |
| 11636 | -0.713 | -0.390 | -0.539 | 0.733 | 0.443 | 0.468 | | | IRS4 | NM_003604 | 0.713 | 0.390 | 0.539 | 0.733 | 0.443 | 0.468 | 0.548 | 0.144 | 0.547 | 0.162 | 0.548 | 0.161 |
| 15757 | -0.705 | -0.814 | -0.864 | 0.551 | 0.450 | 0.330 | | | CS | NM_004077 | 0.705 | 0.814 | 0.864 | 0.551 | 0.450 | 0.330 | 0.619 | 0.211 | 0.794 | 0.081 | 0.444 | 0.111 |
| 13340 | -0.685 | -0.705 | -0.553 | 0.251 | 0.625 | 0.287 | | | OAF | NM_178507 | 0.685 | 0.705 | 0.553 | 0.251 | 0.625 | 0.287 | 0.518 | 0.200 | 0.648 | 0.083 | 0.388 | 0.206 |
| 13767 | -0.680 | -0.401 | -0.451 | 0.384 | 0.636 | 0.619 | | | PABPC4 | NM_003819 | 0.680 | 0.401 | 0.451 | 0.384 | 0.636 | 0.619 | 0.529 | 0.131 | 0.511 | 0.149 | 0.546 | 0.141 |
| 12023 | -0.657 | -0.448 | -0.307 | 0.638 | 0.483 | 0.498 | | | none | NM_138471 | 0.657 | 0.448 | 0.307 | 0.638 | 0.483 | 0.498 | 0.505 | 0.129 | 0.471 | 0.176 | 0.540 | 0.085 |
| 14084 | -0.610 | -0.444 | -0.558 | 0.313 | 0.468 | 0.423 | | | none | NM_006857 | 0.610 | 0.444 | 0.558 | 0.313 | 0.468 | 0.423 | 0.469 | 0.105 | 0.537 | 0.085 | 0.401 | 0.080 |
| 3922 | -0.609 | -0.348 | -0.705 | 0.841 | 0.635 | 1.156 | | | PPP2R1A | NM_014225 | 0.609 | 0.348 | 0.705 | 0.841 | 0.635 | 1.156 | 0.716 | 0.259 | 0.554 | 0.185 | 0.877 | 0.262 |
| 5947 | -0.600 | -0.342 | -0.268 | 0.580 | 0.685 | 0.560 | | | PLAGL1 | NM_002656 | 0.600 | 0.342 | 0.268 | 0.580 | 0.685 | 0.560 | 0.506 | 0.163 | 0.403 | 0.174 | 0.608 | 0.067 |
| 3235 | -0.593 | -0.353 | -0.324 | 0.689 | 0.555 | 0.528 | | | FYN | NM_002037 | 0.593 | 0.353 | 0.324 | 0.689 | 0.555 | 0.528 | 0.507 | 0.142 | 0.423 | 0.148 | 0.591 | 0.086 |
| 1893 | -0.562 | -0.655 | -0.602 | 0.513 | 0.458 | 0.533 | | | SFRS6 | NM_006275 | 0.562 | 0.655 | 0.602 | 0.513 | 0.458 | 0.533 | 0.554 | 0.069 | 0.606 | 0.047 | 0.501 | 0.039 |
| 16368 | -0.560 | -0.610 | -0.533 | 0.385 | 0.305 | 0.567 | | | UBE2R2 | NM_017811 | 0.560 | 0.610 | 0.533 | 0.385 | 0.305 | 0.567 | 0.493 | 0.120 | 0.568 | 0.039 | 0.419 | 0.134 |
| 6374 | -0.522 | -0.422 | -0.604 | 0.524 | 0.528 | 0.561 | | | SCAMP4 | NM_079834 | 0.522 | 0.422 | 0.604 | 0.524 | 0.528 | 0.561 | 0.527 | 0.060 | 0.516 | 0.091 | 0.538 | 0.020 |
| 727 | -0.522 | -0.108 | -0.506 | 0.791 | 1.065 | 0.621 | | | UNC5B | NM_170744 | 0.522 | 0.108 | 0.506 | 0.791 | 1.065 | 0.621 | 0.602 | 0.319 | 0.379 | 0.235 | 0.826 | 0.224 |
| 10516 | -0.470 | -0.421 | -0.413 | 0.480 | 0.583 | 0.544 | | | HSPA9 | NM_004134 | 0.470 | 0.421 | 0.413 | 0.480 | 0.583 | 0.544 | 0.485 | 0.067 | 0.435 | 0.031 | 0.536 | 0.052 |
| 15923 | -0.396 | -0.477 | -0.506 | 0.311 | 0.534 | 0.698 | | | SUMF2 | NM_015411 | 0.396 | 0.477 | 0.506 | 0.311 | 0.534 | 0.698 | 0.487 | 0.131 | 0.460 | 0.057 | 0.514 | 0.194 |
| 6219 | -0.376 | -0.647 | -0.427 | 0.502 | 0.508 | 0.599 | | | CFL1 | NM_005507 | 0.376 | 0.647 | 0.427 | 0.502 | 0.508 | 0.599 | 0.510 | 0.102 | 0.483 | 0.144 | 0.536 | 0.054 |
| 2388 | -0.352 | -0.733 | -0.479 | 0.810 | 0.500 | 0.757 | | | DDR2 | NM_006182 | 0.352 | 0.733 | 0.479 | 0.810 | 0.500 | 0.757 | 0.605 | 0.186 | 0.521 | 0.194 | 0.689 | 0.166 |
| 4283 | -0.335 | -0.437 | -0.505 | 0.483 | 0.507 | 0.677 | | | EIF5A | NM_001970 | 0.335 | 0.437 | 0.505 | 0.483 | 0.507 | 0.677 | 0.491 | 0.112 | 0.426 | 0.086 | 0.556 | 0.106 |
| 11318 | -0.304 | -0.423 | -0.429 | 0.627 | 0.932 | 0.776 | | | C5 | NM_001735 | 0.304 | 0.423 | 0.429 | 0.627 | 0.932 | 0.776 | 0.582 | 0.240 | 0.385 | 0.071 | 0.778 | 0.153 |
| 7702 | -0.259 | -0.363 | -0.526 | 0.482 | 0.728 | 0.648 | | | H2AFX | NM_002105 | 0.259 | 0.363 | 0.526 | 0.482 | 0.728 | 0.648 | 0.501 | 0.174 | 0.383 | 0.135 | 0.619 | 0.125 |

| | |
|---|---|
| Max | 0.810 |
| Min | 0.469 |
| Mean | 0.563 |
| SD | 0.094 |

FIG. 15A

Down-regulated in Rz1498 vs psiRNA    Total 20

| | log2 ratio | | | | | | | Gene_Symbol | Target_NM | Log2 ratio ajusted (±) | | | | | | | Mean (6) | SD | Mean (g) | SD | Mean (R) | SD |
|---|---|---|---|---|---|---|---|---|---|---|---|---|---|---|---|---|---|---|---|---|---|---|
| id | 396619 | 396615 | 396694 | 396612 | 396521 | 396688 | | | | 396619 | 396615 | 396694 | 396612 | 396521 | 396688 | | | | | | | |
| 15523 | 0.854 | 0.525 | 0.609 | -0.999 | -0.909 | -0.800 | TMEPAI | NM_020182 | -0.854 | -0.526 | -0.609 | -0.999 | -0.909 | -0.800 | -0.783 | 0.181 | -0.663 | 0.171 | -0.903 | 0.100 |
| 15477 | 0.698 | 0.681 | 0.467 | 0.549 | 0.292 | -0.405 | C4orf35 | NM_033122 | -0.698 | -0.681 | -0.467 | -0.549 | -0.292 | -0.405 | -0.515 | 0.159 | -0.615 | 0.129 | -0.415 | 0.129 |
| 6571 | 0.630 | 0.701 | 0.937 | -0.704 | -0.515 | -1.044 | DDIT4 | NM_019058 | -0.630 | -0.701 | -0.937 | -0.704 | -0.515 | -1.044 | -0.755 | 0.198 | -0.756 | 0.161 | -0.754 | 0.268 |
| 1630 | 0.617 | 0.628 | 0.522 | -0.363 | -0.282 | -0.108 | HIST2H2BE | NM_003528 | -0.617 | -0.628 | -0.522 | -0.363 | -0.282 | -0.108 | -0.420 | 0.206 | -0.589 | 0.058 | -0.251 | 0.130 |
| 6216 | 0.607 | 0.483 | 0.611 | -0.678 | -0.567 | -0.441 | C1orf91 | NM_019118 | -0.607 | -0.483 | -0.611 | -0.678 | -0.567 | -0.441 | -0.565 | 0.088 | -0.567 | 0.073 | -0.562 | 0.119 |
| 11114 | 0.588 | 0.399 | 0.278 | -0.644 | -0.665 | -0.783 | BRUNOL6 | NM_052840 | -0.588 | -0.399 | -0.278 | -0.644 | -0.665 | -0.783 | -0.560 | 0.187 | -0.422 | 0.156 | -0.697 | 0.075 |
| 11185 | 0.534 | 0.378 | 0.628 | -0.423 | -0.207 | -0.476 | TUBD1 | NM_016261 | -0.534 | -0.378 | -0.628 | -0.423 | -0.207 | -0.476 | -0.441 | 0.144 | -0.513 | 0.126 | -0.369 | 0.142 |
| 6117 | 0.467 | -0.004 | 0.174 | -0.676 | -0.712 | -0.479 | CD180 | NM_005582 | -0.467 | 0.004 | -0.174 | -0.676 | -0.712 | -0.479 | -0.417 | 0.282 | -0.212 | 0.238 | -0.622 | 0.125 |
| 1541 | 0.458 | 0.336 | 0.719 | -0.268 | -0.198 | -0.598 | IER3 | NM_003897 | -0.458 | -0.336 | -0.719 | -0.268 | -0.198 | -0.598 | -0.430 | 0.201 | -0.504 | 0.196 | -0.355 | 0.214 |
| 4200 | 0.442 | 0.204 | 0.104 | -0.611 | -0.849 | -0.518 | APCS | NM_001639 | -0.442 | -0.204 | -0.104 | -0.611 | -0.849 | -0.518 | -0.455 | 0.272 | -0.250 | 0.174 | -0.659 | 0.171 |
| 5995 | 0.426 | 0.473 | 0.628 | -0.385 | -0.540 | -0.581 | ID4 | NM_001546 | -0.426 | -0.473 | -0.628 | -0.385 | -0.540 | -0.581 | -0.506 | 0.094 | -0.509 | 0.106 | -0.502 | 0.103 |
| 1082 | 0.423 | 0.605 | 0.600 | -0.271 | -0.449 | -0.306 | HSPA1B | NM_005346 | -0.423 | -0.605 | -0.600 | -0.271 | -0.449 | -0.306 | -0.442 | 0.141 | -0.543 | 0.104 | -0.342 | 0.094 |
| 7833 | 0.379 | 0.139 | 0.355 | -0.526 | -0.648 | -0.721 | SHANK1 | NM_016148 | -0.379 | -0.139 | -0.355 | -0.526 | -0.648 | -0.721 | -0.461 | 0.214 | -0.291 | 0.132 | -0.632 | 0.099 |
| 5599 | 0.376 | 0.615 | 0.661 | -0.077 | -0.302 | -0.603 | RN7SK | NR_001445 | -0.376 | -0.615 | -0.661 | -0.077 | -0.302 | -0.603 | -0.439 | 0.228 | -0.551 | 0.153 | -0.327 | 0.264 |
| 16736 | 0.364 | 0.443 | 0.093 | -0.692 | -0.520 | -0.576 | RPP30 | NM_006413 | -0.364 | -0.443 | -0.093 | -0.692 | -0.520 | -0.576 | -0.448 | 0.207 | -0.300 | 0.184 | -0.596 | 0.088 |
| 1423 | 0.304 | 0.682 | 0.422 | -0.368 | -0.340 | -0.407 | SIX1 | NM_005982 | -0.304 | -0.682 | -0.422 | -0.368 | -0.340 | -0.407 | -0.421 | 0.135 | -0.469 | 0.193 | -0.372 | 0.034 |
| 12510 | 0.228 | 0.343 | 0.094 | -0.682 | -0.677 | -0.683 | PPFIBP1 | NM_003622 | -0.228 | -0.343 | -0.094 | -0.682 | -0.677 | -0.683 | -0.451 | 0.263 | -0.222 | 0.125 | -0.681 | 0.003 |
| 14332 | 0.210 | 0.492 | 0.560 | -0.307 | -0.720 | -0.678 | FOXO3 | NM_001455 | -0.210 | -0.492 | -0.560 | -0.307 | -0.720 | -0.678 | -0.495 | 0.202 | -0.421 | 0.186 | -0.568 | 0.227 |
| 13245 | 0.118 | 0.193 | -0.041 | -0.556 | -0.811 | -0.847 | CD302 | NM_014880 | -0.118 | -0.193 | 0.041 | -0.556 | -0.811 | -0.847 | -0.414 | 0.376 | -0.090 | 0.119 | -0.738 | 0.159 |
| 11160 | 0.048 | -0.003 | -0.119 | -0.690 | -0.868 | -1.036 | ZNF431 | NM_133473 | -0.048 | 0.003 | 0.119 | -0.690 | -0.868 | -1.036 | -0.420 | 0.502 | 0.025 | 0.086 | -0.865 | 0.173 |

Max  -0.414
Min  -0.783
Mean -0.492
SD    0.105

FIG. 15B

| Down-regulated in sh1498 vs psiRNA | | | | | | Total 34 | | | | | | | | | | | | |
|---|---|---|---|---|---|---|---|---|---|---|---|---|---|---|---|---|---|---|
| | log2 ratio | | | | | | | | | | | | | | | | | |
| Id | 400042 | 400444 | 400436 | 393040 | 393041 | 393034 | Gene_Symbol | Target_NM | 396619 | 396615 | 396694 | 396612 | 396521 | 396688 | Mean (6) | SD | Mean (g) | SD | Mean(rc) | SD |
| 11685 | 1.494 | 0.959 | 1.377 | -0.472 | -0.402 | 0.073 | SOX3 | NM_005634 | -1.494 | -0.959 | -1.377 | -0.472 | -0.402 | 0.073 | -0.772 | 0.610 | -1.277 | 0.281 | -0.267 | 0.297 |
| 532 | 1.436 | 1.041 | 1.383 | -0.274 | -0.645 | 0.165 | GFRA1 | NM_005264 | -1.436 | -1.041 | -1.388 | -0.274 | -0.645 | -0.166 | -0.825 | 0.549 | -1.288 | 0.216 | -0.362 | 0.251 |
| 1227 | 1.423 | 0.939 | 1.150 | -0.359 | -0.352 | -0.110 | TIGD4 | NM_145720 | -1.423 | -0.939 | -1.150 | -0.359 | -0.352 | -0.110 | -0.722 | 0.522 | -1.171 | 0.243 | -0.274 | 0.142 |
| 13599 | 1.406 | 1.105 | 1.402 | -0.593 | -0.320 | -0.091 | MTERFD1 | NM_015942 | -1.406 | -1.105 | -1.402 | -0.593 | -0.320 | -0.091 | -0.820 | 0.565 | -1.304 | 0.173 | -0.335 | 0.251 |
| 16774 | 1.331 | 1.050 | 1.205 | 0.177 | -0.353 | 0.139 | TAS1R2 | NM_152232 | -1.331 | -1.050 | -1.205 | -0.177 | -0.353 | -0.139 | -0.663 | 0.611 | -1.195 | 0.141 | -0.130 | 0.249 |
| 8777 | 1.293 | 1.060 | 1.387 | -0.225 | -0.428 | 0.001 | ALDH16A1 | NM_153329 | -1.293 | -1.060 | -1.387 | -0.225 | -0.428 | 0.001 | -0.732 | 0.590 | -1.247 | 0.168 | -0.217 | 0.215 |
| 17349 | 1.244 | 0.845 | 1.292 | -0.165 | -0.375 | 0.164 | MYO9B | NM_004145 | -1.244 | -0.845 | -1.292 | -0.165 | -0.375 | 0.164 | -0.626 | 0.595 | -1.127 | 0.245 | -0.125 | 0.272 |
| 498 | 1.230 | 1.035 | 1.418 | 0.202 | -0.530 | -0.008 | CREBBP | NM_004380 | -1.230 | -1.035 | -1.418 | -0.202 | -0.530 | -0.008 | -0.737 | 0.576 | -1.228 | 0.192 | -0.247 | 0.264 |
| 7716 | 1.219 | 0.758 | 0.821 | -0.251 | -0.049 | 0.136 | ATP10D | NM_020453 | -1.219 | -0.768 | -0.821 | -0.251 | -0.049 | -0.136 | -0.495 | 0.522 | -0.936 | 0.247 | -0.055 | 0.194 |
| 2546 | 1.165 | 0.896 | 1.411 | -0.415 | -0.807 | -0.071 | NOXO1 | NM_144603 | -1.165 | -0.898 | -1.411 | -0.415 | -0.807 | -0.071 | -0.795 | 0.489 | -1.158 | 0.257 | -0.431 | 0.368 |
| 1729 | 1.127 | 0.811 | 1.401 | -0.042 | -0.413 | 0.264 | FPGS | NM_004957 | -1.127 | -0.811 | -1.401 | -0.042 | -0.413 | 0.264 | -0.588 | 0.641 | -1.113 | 0.295 | -0.064 | 0.339 |
| 16434 | 1.072 | 0.868 | 1.540 | -0.138 | -0.492 | 0.179 | HPS4 | NM_022081 | -1.072 | -0.868 | -1.540 | -0.138 | -0.492 | 0.179 | -0.655 | 0.631 | -1.160 | 0.345 | -0.150 | 0.336 |
| 5741 | 1.067 | 0.807 | 0.924 | 0.039 | -0.606 | 0.114 | none | XM_065899 | -1.067 | -0.807 | -0.934 | -0.039 | -0.606 | 0.114 | -0.557 | 0.487 | -0.936 | 0.130 | -0.177 | 0.379 |
| 12182 | 1.066 | 0.602 | 1.062 | -0.184 | -0.165 | 0.102 | NDRG2 | NM_201536 | -1.066 | -0.602 | -1.062 | -0.184 | -0.165 | 0.102 | -0.496 | 0.494 | -0.910 | 0.267 | -0.082 | 0.160 |
| 11305 | 1.064 | 0.824 | 1.393 | -0.451 | -0.649 | 0.214 | ACPT | NM_033068 | -1.064 | -0.824 | -1.393 | -0.451 | -0.649 | 0.214 | -0.695 | 0.553 | -1.094 | 0.286 | -0.295 | 0.452 |
| 6965 | 1.056 | 0.808 | 0.961 | -0.232 | -0.333 | 0.121 | SERPIND1 | NM_000185 | -1.056 | -0.808 | -0.961 | -0.232 | -0.333 | 0.121 | -0.545 | 0.467 | -0.942 | 0.125 | -0.148 | 0.238 |
| 14553 | 1.017 | 0.539 | 0.666 | -0.176 | -0.459 | -0.029 | SLC11A1 | NM_000578 | -1.017 | -0.539 | -0.666 | -0.176 | -0.459 | -0.029 | -0.481 | 0.353 | -0.741 | 0.248 | -0.221 | 0.219 |
| 16079 | 0.998 | 0.781 | 1.324 | -0.323 | -0.510 | 0.151 | MAGEB4 | NM_002367 | -0.998 | -0.781 | -1.324 | -0.323 | -0.510 | 0.151 | -0.631 | 0.521 | -1.034 | 0.273 | -0.227 | 0.341 |
| 5290 | 0.955 | 0.635 | 0.832 | -0.180 | -0.024 | -0.014 | PPM1F | NM_014634 | -0.955 | -0.635 | -0.832 | -0.180 | -0.024 | -0.014 | -0.440 | 0.419 | -0.807 | 0.161 | -0.073 | 0.093 |
| 7002 | 0.949 | 0.757 | 1.135 | -0.194 | -0.627 | 0.150 | DUOX2 | NM_014080 | -0.949 | -0.757 | -1.135 | -0.194 | -0.627 | 0.150 | -0.585 | 0.482 | -0.947 | 0.189 | -0.224 | 0.389 |
| 8224 | 0.941 | 0.696 | 1.130 | -0.518 | -0.932 | -0.257 | SEPT5 | NM_002688 | -0.941 | -0.696 | -1.130 | -0.518 | -0.932 | -0.257 | -0.746 | 0.321 | -0.922 | 0.218 | -0.569 | 0.340 |
| 8479 | 0.928 | 0.472 | 1.143 | -0.467 | -0.827 | -0.138 | C1orf198 | NM_032800 | -0.928 | -0.472 | -1.143 | -0.407 | -0.827 | -0.138 | -0.653 | 0.375 | -0.848 | 0.343 | -0.457 | 0.347 |
| 16506 | 0.917 | 0.665 | 0.642 | -0.063 | -0.260 | -0.255 | ZNF577 | NM_032679 | -0.917 | -0.665 | -0.642 | -0.063 | -0.260 | -0.255 | -0.467 | 0.324 | -0.741 | 0.153 | -0.193 | 0.112 |
| 2080 | 0.900 | 0.628 | 1.106 | -0.140 | -0.333 | -0.186 | GJB1 | NM_000166 | -0.900 | -0.628 | -1.106 | -0.140 | -0.333 | -0.186 | -0.549 | 0.396 | -0.878 | 0.240 | -0.220 | 0.101 |
| 894 | 0.757 | 0.527 | 0.988 | -0.203 | -0.539 | -0.066 | NFATC1 | NM_006162 | -0.757 | -0.527 | -0.988 | -0.203 | -0.539 | -0.066 | -0.513 | 0.341 | -0.757 | 0.231 | -0.269 | 0.243 |
| 12241 | 0.746 | 0.467 | 0.584 | -0.336 | -0.346 | -0.107 | EIF4A3 | NM_014740 | -0.746 | -0.487 | -0.584 | -0.336 | -0.346 | -0.107 | -0.434 | 0.222 | -0.606 | 0.131 | -0.263 | 0.135 |
| 16262 | 0.610 | 0.485 | 0.585 | -0.371 | -0.438 | -0.504 | GDF15 | NM_004864 | -0.610 | -0.485 | -0.585 | -0.371 | -0.438 | -0.504 | -0.499 | 0.089 | -0.560 | 0.066 | -0.438 | 0.067 |
| 12951 | 0.600 | 0.624 | 0.535 | -0.380 | -0.559 | -0.491 | RBM34 | NM_015014 | -0.600 | -0.624 | -0.535 | -0.380 | -0.559 | -0.491 | -0.532 | 0.088 | -0.586 | 0.046 | -0.477 | 0.090 |
| 11980 | 0.589 | 0.857 | 0.592 | -0.184 | -0.364 | -0.394 | LMNB1 | NM_005573 | -0.589 | -0.857 | -0.592 | -0.184 | -0.364 | -0.394 | -0.497 | 0.234 | -0.679 | 0.154 | -0.314 | 0.114 |
| 15523 | 0.559 | 0.365 | 0.390 | -0.625 | -0.563 | -0.640 | TMEPAI | NM_020182 | -0.559 | -0.365 | -0.390 | -0.625 | -0.563 | -0.640 | -0.524 | 0.118 | -0.438 | 0.106 | -0.609 | 0.041 |
| 5735 | 0.540 | 0.324 | 0.499 | -0.528 | -0.482 | -0.501 | LYPLA3 | NM_012320 | -0.540 | -0.324 | -0.499 | -0.528 | -0.482 | -0.501 | -0.479 | 0.079 | -0.454 | 0.115 | -0.504 | 0.023 |
| 2094 | 0.507 | 0.389 | 0.209 | 0.504 | 0.557 | 0.621 | ARL6IP6 | NM_152522 | -0.507 | -0.389 | -0.209 | -0.604 | -0.557 | -0.621 | -0.481 | 0.157 | -0.368 | 0.150 | -0.594 | 0.033 |
| 1849 | 0.303 | 0.406 | 0.297 | -0.629 | -0.606 | -0.490 | GJA1 | NM_000165 | -0.303 | -0.406 | -0.297 | -0.629 | -0.606 | -0.490 | -0.455 | 0.145 | -0.335 | 0.061 | -0.575 | 0.075 |
| 8036 | 0.214 | 0.205 | 0.166 | -0.702 | -0.592 | -0.620 | UBE2W | NM_018299 | -0.214 | -0.205 | -0.166 | -0.702 | -0.592 | -0.620 | -0.417 | 0.246 | -0.195 | 0.026 | -0.638 | 0.057 |
| | | | | | | | | | | | | | Max | | -0.417 | | | | | |
| | | | | | | | | | | | | | Min | | -0.825 | | | | | |
| | | | | | | | | | | | | | Mean | | -0.591 | | | | | |
| | | | | | | | | | | | | | SD | | 0.122 | | | | | |

FIG. 15D

ANTISENSE-BASED SMALL RNA AGENTS TARGETING THE GAG OPEN READING FRAME OF HIV-1 RNA

CROSS REFERENCE TO RELATED APPLICATIONS

This application is a National Entry Application of PCT application no PCT/CA2014/050814 filed on Aug. 25, 2014 and published in English under PCT Article 21(2), which itself claims the benefit of U.S. provisional application Ser. No. 61/869,852 filed on Aug. 26, 2013. All documents noted above are incorporated herein by reference in their entirety.

TECHNICAL FIELD

The present invention generally relates to the treatment of Human Immunodeficiency Virus 1 (HIV-1) infection.

SEQUENCE LISTING

Pursuant to 37 C.F.R. 1.821(c), a sequence listing is submitted herewith as an ASCII complaint text file named "11168_421-Seq_Listing_ST25.txt", created on Feb. 11, 2016 and having a size of ~30 kilobytes. The content of the aforementioned file is hereby incorporated by reference in its entirety.

BACKGROUND ART

Over 30 small molecules are available for the treatment of Human Immunodeficiency Virus 1 (HIV-1) infection, targeting the viral proteins reverse transcriptase (RT), protease and integrase, as well as the cellular entry co-receptor, CCR5[1]. Although treatment of HIV-1 with combination small molecule therapy is effective in preventing Acquired Immune Deficiency Syndrome (AIDS), it is not able to eradicate the virus and is associated with a number of short- and long-term side effects[2]. Alternative therapeutic strategies for long-term viral suppression with low adverse effects are needed.

Small RNAs represent a growing class of molecules with the potential to complement or replace current therapies. They are being evaluated for use in ex vivo gene therapy[3] and with advances that have been made in their systemic delivery[4], may soon be evaluated for use in combination drug therapy. Many small RNAs, including antisense oligonucleotides (ASONs), ribozymes (Rzs), decoys, aptamers, small nuclear (sn) RNAs, and small interfering (si) or short hairpin (sh) RNAs have been designed with diverse target sites in the HIV-1 replication cycle[5]. Antisense-based RNAs (ASONs, Rzs, snRNAs, sh/siRNAs) can be designed to target HIV-1 RNA, and several therapeutic candidates have been described.

Rzs targeting HIV-1 RNA have been made by modifying hammerhead, hairpin[6] and bacterial RNase P[7] motifs. The HDV Rz represents an alternative small Rz motif, that has evolved to function in human cells and has the potential to be used for the development of therapeutic Rzs[8]. To improve the specificity of the HDV Rz for its target RNA, the SOFA (Specific On/oFf Adaptor) module was engineered[9,10] (FIG. 1A). Several SOFA-HDV-Rzs have been identified with the potential to target human[11,12], viral[9,13,14] and bacterial[15] RNAs, including three Rzs that we have evaluated targeting the overlapping Tat/Rev coding sequence of HIV-1 RNA[16].

Optimal hammerhead Rz target sites in HIV-1 RNA have been identified using libraries of Rzs with randomized binding arms[17,18] and a library of Rzs targeting highly conserved sequences[19]. Using different methods and datasets to estimate sequence conservation, sets of optimal siRNAs[20] or shRNAs[21,22] have been identified and two of these studies have reported their conservation estimates in 19 to 21 nt frames[20,22]. Estimates have also been reported at the nucleotide (nt) level to identify or characterize Rz[23], snRNA[24] and shRNA[25] target sites.

The present description refers to a number of documents, the content of which is herein incorporated by reference in their entirety.

SUMMARY OF THE INVENTION

The present invention relates to the following items 1 to 23:

1. An antisense nucleic acid molecule directed against a sequence corresponding to about nucleotide 1495 to about nucleotide 1526 of HIV-1 clone pNL4-3 (GenBank accession No. M19921.2), or the complement thereof.

2. The antisense nucleic acid molecule of item 1, which is directed against a sequence corresponding to about nucleotide 1497 to about nucleotide 1521 of HIV-1 clone pNL4-3 (GenBank accession No. M19921.2), or the complement thereof.

3. The antisense nucleic acid molecule of item 1, which is a ribozyme.

4. The antisense nucleic acid molecule of item 3, wherein said ribozyme is a Specific On/Off Adaptor (SOFA) Hepatitis Delta Virus (HDV) ribozyme.

5. The antisense nucleic acid molecule of item 4, wherein said ribozyme comprises: a recognition domain (RD) comprising the sequence TTCCTGT, a biosensor (Bs) domain comprising the sequence AAGGGTACTA, and a blocker (BI) domain comprising the sequence GGAA.

6. The antisense nucleic acid molecule of item 4, wherein said ribozyme comprises the sequence of SEQ ID NO:142.

7. The antisense nucleic acid molecule of item 1 or 2, which is a short hairpin RNA (shRNA).

8. The antisense nucleic acid molecule of item 6, wherein the shRNA is encoded by a nucleic acid comprising one of the following stem sequences (i) to (xii):

```
(i)
                                  (SEQ ID NO: 93)
5'-GCAGGAACTACTAGTACCCT-3'

(SEQ ID NO: 118)
3'-CGTCCTTGATGATCATGGGA-5';

(ii)
                                  (SEQ ID NO: 87)
5'-ATAGCAGGAACTACTAGTAC-3'

(SEQ ID NO: 119)
3'-TATCGTCCTTGATGATCATG-5';

(iii)
                                  (SEQ ID NO: 89)
5'-TAGCAGGAACTACTAGTACC-3'

(SEQ ID NO: 120)
3'-ATCGTCCTTGATGATCATGG-5';
```

-continued (iv)
5'-AGCAGGAACTACTAGTACCC-3' (SEQ ID NO: 91)

3'-TCGTCCTTGATGATCATGGG-5'; (SEQ ID NO: 121)

(v)
5'-CAGGAACTACTAGTACCCTT-3' (SEQ ID NO: 95)

3'-GTCCTTGATGATCATGGGAA-5'; (SEQ ID NO: 122)

(vi)
5'-GGAACTACTAGTACCCTTCA-3' (SEQ ID NO: 99)

3'-CCTTGATGATCATGGGAAGT-5'; (SEQ ID NO: 123)

(vii)
5'-GCAGGAACTACTAGTACCC-3' (SEQ ID NO: 105)

3'-CGTCCTTGATGATCATGGG-5'; (SEQ ID NO: 124)

(viii)
5'-GCAGGAACTACTAGTACCCTT-3' (SEQ ID NO: 107)

3'-CGTCCTTGATGATCATGGGAA-5'; (SEQ ID NO: 125)

(ix)
5'-GCAGGAACTACTAGTACCCTTCA-3' (SEQ ID NO: 109)

3'-CGTCCTTGATGATCATGGGAAGT-5'; (SEQ ID NO: 126)

(x)
5'-GCAGGAACTACTAGTACCCTTCAGG-3' (SEQ ID NO: 111)

3'-CGTCCTTGATGATCATGGGAAGTCC-5'; (SEQ ID NO: 127)

(xi)
5'-GCAGGAACTACTAGTACCCTTCAGGAA-3' (SEQ ID NO: 113)

3'-CGTCCTTGATGATCATGGGAAGTCCTT-5'; (SEQ ID NO: 128)
or (xii)
5'-GCAGGAACTACTAGTACCCTTCAGGAACA-3' (SEQ ID NO: 115)

3'-CGTCCTTGATGATCATGGGAAGTCCTTGT-5'; (SEQ ID NO: 129)

or an analog thereof.

9. The antisense nucleic acid molecule of item 7, wherein the shRNA comprises a 3'-overhang.

10. The antisense nucleic acid molecule of item 8, wherein the shRNA is encoded by a nucleic acid comprising one of the following sequences (i) to (xii):

(i)
GCAGGAACTACTAGTACCCTACTCGAGAAGGGTACTAGTAGTTCCTGCTT; (SEQ ID NO: 130)

(ii)
ATAGCAGGAACTACTAGTACGCTCGAGGGTACTAGTAGTTCCTGCTATTT; (SEQ ID NO: 131)

(iii)
TAGCAGGAACTACTAGTACCGCTCGAGGGGTACTAGTAGTTCCTGCTATT; (SEQ ID NO: 132)

(iv)
AGCAGGAACTACTAGTACCCACTCGAGAGGGTACTAGTAGTTCCTGCTTT; (SEQ ID NO: 133)

(v)
CAGGAACTACTAGTACCCTTGCTCGAGGAAGGGTACTAGTAGTTCCTGTT; (SEQ ID NO: 134)

(vi)
GGAACTACTAGTACCCTTCACCTCGAGCTGAAGGGTACTAGTAGTTCCTT; (SEQ ID NO: 135)

(vii)
GCAGGAACTACTAGTACCCACTCGAGAGGGTACTAGTAGTTCCTGCTT; (SEQ ID NO: 136)

(viii)
GCAGGAACTACTAGTACCCTTGCTCGAGGAAGGGTACTAGTAGTTCCTGCTT; (SEQ ID NO: 137)

(ix)
GCAGGAACTACTAGTACCCTTCACCTCGAGCTGAAGGGTACTAGTAGTTCCTGCTT; (SEQ ID NO: 138)

(x)
GCAGGAACTACTAGTACCCTTCAGGTCTCGAGTCCTGAAGGGTACTAGTAGTTCCTGCTT; (SEQ ID NO: 139)

(xi)
GCAGGAACTACTAGTACCCTTCAGGAAGCTCGAGGTTCCTGAAGGGTACTAGTAGTTCCTGCTT; (SEQ ID NO: 140)

or (xii)
GCAGGAACTACTAGTACCCTTCAGGAACATCTCGAGTTGTTCCTGAAGGGTACTAGTAGTTCCTGCTT; (SEQ ID NO: 141)

or an analog thereof.

11. The antisense nucleic acid molecule of item 1 or 2, which is a small interfering RNA (siRNA).

12. The antisense nucleic acid molecule of item 10, wherein the siRNA comprises one of the following pair of sequences (i) to (iv):

(i)
si1497 sense:
AGCAGGAACUACUAGUACCCUUCdAdG (SEQ ID NO: 75)

si1497 antisense:
UAUCGUCCUUGAUGAUCAUGGGAAGUC; (SEQ ID NO: 76)

-continued (ii)
sil498 sense:
(SEQ ID NO: 77)
GCAGGAACUACUAGUACCCUUCAdGdG sil498 antisense:
(SEQ ID NO: 78)
AUCGUCCUUGAUGAUCAUGGGAAGUCC;

(iii)
sil499 sense:
(SEQ ID NO: 81)
CAGGAACUACUAGUACCCUUCAGdGdA sil499 antisense:
(SEQ ID NO: 82)
UCGUCCUUGAUGAUCAUGGGAAGUCCU;
or (iv)
sil498-29 sense:
(SEQ ID NO: 79)
GCAGGAACUACUAGUACCCUUCAGGAA sil498-29 antisense:
(SEQ ID NO: 80)
dAdTCGUCCUUGAUGAUCAUGGGAAGUCCUU;

or an analog thereof.

13. A vector comprising a nucleic acid encoding the antisense nucleic acid molecule of any one of items 1 to 12.

14. A cell comprising the antisense nucleic acid molecule of any one of items 1 to 12 and/or the vector of item 13.

15. A composition comprising (a) the antisense nucleic acid molecule of any one of items 1 to 12, the vector of item 13 and/or the cell of item 14; and (b) an excipient.

16. A method for inhibiting HIV-1 replication in a cell, the method comprising contacting said cell with an effective amount of the antisense nucleic acid molecule of any one of items 1 to 12, the vector of item 13, the cell of item 14 and/or the composition of item 15.

17. A method for treating HIV-1 infection in a subject, the method comprising administering to said subject an effective amount of the antisense nucleic acid molecule of any one of items 1 to 12, the vector of item 13, the cell of item 14 and/or the composition of item 15.

18. Use of the antisense nucleic acid molecule of any one of items 1 to 12, the vector of item 13, the cell of item 14 and/or the composition of item 15, for inhibiting HIV-1 replication in a cell.

19. Use of the antisense nucleic acid molecule of any one of items 1 to 12, the vector of item 13, the cell of item 14 and/or the composition of item 15, for the manufacture of a medicament for inhibiting HIV-1 replication in a cell.

20. Use of the antisense nucleic acid molecule of any one of items 1 to 12, the vector of item 13, the cell of item 14 and/or the composition of item 15, for treating HIV-1 infection in a subject.

21. Use of the antisense nucleic acid molecule of any one of items 1 to 12, the vector of item 13, the cell of item 14 and/or the composition of item 15, for the manufacture of a medicament for treating HIV-1 infection in a subject.

22. The antisense nucleic acid molecule of any one of items 1 to 12, the vector of item 13, the cell of item 14 and/or the composition of item 15, for inhibiting HIV-1 replication in a cell and/or treating HIV-1 infection in a subject.

23. The antisense nucleic acid molecule of any one of items 1 to 12, the vector of item 13, the cell of item 14 and/or the composition of item 15, for the manufacture of a medicament for inhibiting HIV-1 replication in a cell and/or treating HIV-1 infection in a subject.

24. Use of the antisense nucleic acid molecule of any one of items 1 to 12, the vector of item 13, the cell of item 14 and/or the composition of item 15, as a medicament.

Other objects, advantages and features of the present invention will become more apparent upon reading of the following non-restrictive description of specific embodiments thereof, given by way of example only with reference to the accompanying drawings.

BRIEF DESCRIPTION OF DRAWINGS

In the appended drawings:

FIG. 1A: The SOFA-HDV-Rz is illustrated in both its OFF and ON conformations. In the OFF conformation, the SOFA blocker (BI) base pairs with the last 4 nts of the recognition domain (RD). When the SOFA biosensor (Bs) base pairs with a specific target sequence, the RD is released from the BI sequence and binds at 3 to 5 nts upstream from the Bs binding site in the ON conformation. The first nt in the target site (n+1) must be a G, forming a wobble base pair with the RD U. The cleavage site is indicated with an arrow and the nt $C_{76}$, which can be mutated to disable the catalytic activity of the SOFA-HDV-Rz, is shown as a circle in the Rz backbone.

FIG. 2A: Criteria used to identify SOFA-HDV-Rz target sites in HIV-1 RNA based on our conservation estimates at the nt level are illustrated. The number of nts between the RD and the Bs (spacer, 3-5), and the length of the Bs (9-11), were adjusted to avoid poorly conserved positions or to reduce potential off-target effects on human RNAs. A spacer of 4 nt and Bs length of 10 nt were used as the default positioning. FIG. 2B: Target sites were excluded if they were not identical in HIV-1 NL4-3 or if the corresponding Rz had potential target sites in human RNAs using a cut-off score of 20 in the Ribosubstrates tool[26]. FIG. 2C: Sequence conservation estimates in the 5' region of HIV-1 RNA are shown for each nt position in HIV-1 NL4-3 with the selected Rz binding sites shaded in grey. SOFA-HDV-Rzs were named according to the first nt in their binding site. The dashed line represents the separation between the 5'UTR and Gag ORF. SOFA-HDV-Rz target sites that were moderately conserved, but did not meet our conservation criteria, are indicated with an asterisk (*).

FIG. 4A: Schematic representation of the SOFA-HDV-Rz1498 target site (T) and variants (Rz). SOFA-HDV-Rz1498A76 has a C to A mutation in the Rz backbone, -Rz1498Bs1 and -Rz1498Bs2 have 1 or 2 nt variants in the biosensor (Bs), indicated in lower case. FIG. 4B: Effects of each SOFA-HDV-Rz1498 variant on viral production in HEK293T cells were evaluated exactly as in FIG. 3. Rzs were evaluated in at least three independent experiments with one to three replicate transfections (reported as mean+/−SEM, n=6-10). The relative expression of Rz and 5S RNA loading control for the different conditions are shown below for one of two independent experiments performed in HEK293T cells seeded in a 12-well plate and co-transfected with twice the amount of DNA used for the evaluation of viral production in 24 well plates. FIG. 4C: Single turnover in vitro cleavage activities for SOFA-HDV-Rz1498, -Rz1498Bs1 and -Rz1498Bs2 were determined at different incubation times with a small substrate RNA (Rz>>substrate). Cleavage % was measured by dividing cleaved products by cleaved+uncleaved products, quantified from bands on a gel. A nonlinear regression one phase exponential association equation with least squares (ordinary) fit was determined using Graph Pad Prism™ for the different Rzs. All data points represent two independent experiments and are reported as mean+/−SEM (n=2). The average rate constants ($k_{obs}$) and maximum cleavage values ($F_{max}$) for the SOFA-HDV-Rzs are reported in the table.

FIGS. 5A to D show the effects of shRNA1498 on HIV-1 production. FIG. 5A: Sequences targeted by shRNA1498 and control shRNAs targeting HIV-1 RNA (shRNA522, shRNA553, and shRNA5983) are shown in relation to conservation estimates at the nt level reported in reference #51. FIG. 5B: Effects of shRNA1498 and a nonsense shRNA (shRNAns) on viral production in HEK293T cells were evaluated exactly as in FIG. 3. Rzs and shRNAs were evaluated in at least three independent experiments with one to three replicate transfections (reported as mean+/−SEM, n=6-10). The relative intracellular expression of HIV-1 Gag polyprotein (GAG, p55), matrix-capsid intermediate (MA-CA, p39), and capsid (CA, p24) proteins as well as GAPDH loading control are shown below for one of two independent experiments performed in HEK293T cells seeded in a 12-well plate and co-transfected with twice the amount of DNA used for the evaluation of viral production. Relative band intensities for Gag and CA were calculated using Image J™ software and are expressed as a fraction of the intensity of Gag in the SOFA-HDV-RzHBV control lane. FIG. 5C: The potency of shRNAs was evaluated by co-transfecting HEK293T cells seeded in a 24-well plate with 100 ng of pNL4-3 DNA and 1-750 ng of shRNA expressing plasmids. For lower amounts of shRNA plasmid DNA (1-500 ng), co-transfections were topped up to 850 ng total DNA by the addition of an irrelevant plasmid (pBluescript SK+, Stratagene, La Jolla, Calif.). Relative RT activity measurements were log transformed and a nonlinear regression log(inhibitor) vs. response equation with least squares (ordinary) fit was determined using Graph Pad Prism™ for the different shRNAs. All data-points represent at least two independent experiments with 2-3 replicates and are reported as mean+/−SEM (n=4-8). FIG. 5D: Combinations of SOFA-HDV-Rz and shRNA expressing plasmids were evaluated in HEK293T cells seeded in 24-well plates and co-transfected with 100 ng pNL4-3, 10 ng of shRNA expressing plasmid and 1 µg of Rz expressing plasmid. Data were normalized to co-transfection of 100 ng pNL4-3 with 1 µg of the empty Rz/shRNA expression plasmid and are reported as the mean+/−SEM from two independent experiments performed in triplicate (n=6).

FIGS. 6A and B show the inhibition of HIV-1 production from diverse viral strains by SOFA-HDV-Rz1498 and shRNA1498. FIG. 6A: The sequence in and around the shRNA1498 and SOFA-HDV-Rz1498 target site is shown for HIV-1 NL4-3 (M19921), MAL (K03456), AD8 (AF004394), Indie-C1 (AB023804.1), MJ4 (AF321523), 94UG114 (U88824.1) and 97GH-AG1 (AB049811.1). The overlapping target site for shRNA1498 and SOFA-HDV-Rz1498 is indicated by the brackets, with both the RD (7 nt) and Bs (10 nt) binding sites underlined. Nt variations compared to HIV-1 NL4-3 are indicated by the arrows and the start and end positions for each sequence are shown according to their annotation in Genbank. FIG. 6B: The activity of the indicated Rz and shRNA expression plasmids against the different HIV-1 strains was determined as in FIG. 3 (n=4-12). Left bars=RzHBV; $2^{nd}$ bars=shRNAns; $3^{rd}$ bars=Rz1498; right bars=shRNA1498.

FIG. 8A: Jurkat cells expressing the indicated SOFA-HDV-Rzs and shRNAs were infected with HIV-1 pNL4-3. The average RT activity (cpm) across four independent infections performed in triplicate (n=12) is shown for days 10 and 14 following infection. Left bars=RzHBV; $2^{nd}$ bars=shRNAns; $3^{rd}$ bars=Rz1498A76; $4^{th}$ bars=Rz1498; right bars=shRNA1498.

FIG. 10A: HEK293T cells were seeded in 24 well plates and transfected exactly as in FIG. 3. RT activity is expressed as counts per minute for cells transfected with the empty Rz expression plasmid (psiRNA), the irrelevant SOFA-HDV-RzHBV and SOFA-HDV-Rz1498 targeting HIV-1 RNA.

FIG. 11A: The relative intracellular expression of HIV-1 Gag polyprotein (Gag, p55), matrix-capsid intermediate (MA-CA, p39), and capsid (CA, p24) proteins as well as GAPDH loading control are shown.

FIG. 13A: 10,000 events are shown for the different cell lines, Green fluorescence levels versus Forward scatter (FSC) is plotted, showing the level of green fluorescent protein (GFP) expression and approximate cell size (FSC) for the different Jurkat cell lines.

FIG. 14A: Results for 25 by siRNAs with overlapping target sites.

FIGS. 15A to 15D show the data of microarray experiments performed as triplicate dye swaps expressed as the log 2 ratio of SOFA-HDV-Rz1498 (Rz1498, FIGS. 12A and 12B) and shRNA1498 (FIGS. 12C and 12D) compared to the empty vector cotransfected cells (psiRNA). FIG. 15A=Genes up-regulated in Rz1498-transfected cells vs. control cells; FIG. 15B=Genes down-regulated in Rz1498-transfected cells vs. control cells; FIG. 15C=Genes up-regulated in shRNA1498-transfected cells vs. control cells; FIG. 15D=Genes down-regulated in shRNA1498-transfected cells vs. control cells.

DISCLOSURE OF INVENTION

Terms and symbols of genetics, molecular biology, biochemistry and nucleic acid used herein follow those of standard treatises and texts in the field, e.g. Kornberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Eckstein, editor, Oligonucleotides and Analogs: A Practical Approach (Oxford University Press, New York, 1991); Gait, editor, Oligonucleotide Synthesis: A Practical Approach (IRL Press, Oxford, 1984); and the like. All terms are to be understood with their typical meanings established in the relevant art. Standard techniques may be used for chemical synthesis, and chemical analysis. Certain such techniques and procedures may be found for example in "Carbohydrate Modifications in Antisense Research" Edited by Sangvi and Cook, American Chemical Society, Washington D.C., 1994; "Remington's Pharmaceutical Sciences," Mack Publishing Co., Easton, Pa., 21$^{st}$ edition, 2005; and "Antisense Drug Technology, Principles, Strategies, and Applications" Edited by Stanley T. Crooke, CRC Press, Boca Raton, Fla.

The articles "a" and an are used herein to refer to one or to more than one (i.e. to at least one) of the grammatical object of the article. By way of example, "an element" means one element or more than one element. Throughout this specification, unless the context requires otherwise, the words "comprise," "comprises" and "comprising" will be understood to imply the inclusion of a stated step or element or group of steps or elements but not the exclusion of any other step or element or group of steps or elements.

Figure 1A:
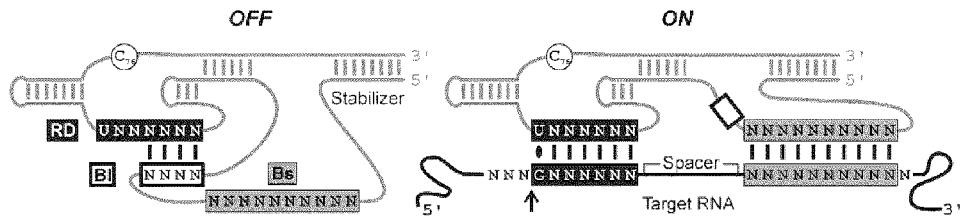
FIGS. 1A and B show a schematic representation of the SOFA-HDV-Rz and the HIV-1 RNA region used to identify SOFA-HDV-Rz target sites.

In the studies described herein, the present inventors have screened HIV-1 RNA for highly conserved target sites at its 5' end, from the beginning of the 5'UTR to the end of the gag ORF (FIG. 1A). SOFA-HDV-Rzs targeting a novel site in the gag ORF with significant activity against HIV-1 production were identified, and shRNAs/siRNAs targeting the same site were shown to be extremely potent and active inhibitors of viral production. Both types of molecules were able to inhibit HIV-1 production from diverse viral strains and were active against HIV-1 replication in a T lymphocyte cell model. The results provide evidence that targeting this site using antisense-based agents constitutes a suitable approach for HIV-1 therapy.

Accordingly, in a first aspect, the present invention provides an antisense nucleic acid molecule directed against a sequence corresponding to about nucleotide 1495 to about nucleotide 1526 of HIV-1 clone pNL4-3 (GenBank accession No. M19921.2), or a fragment thereof, or a sequence complementary thereto. Nucleotide numbering described herein uses numbering in the reference HIV-1 clone pNL4-3 (GenBank accession No. M19921.2). Nucleotides 1495 to 1526 correspond to the sequence ATAGCAGGAAC-TACTAGTACCCTTCAGGAACA (SEQ ID NO: 117). The corresponding positions/sequences (which defines the region targeted by the antisense nucleic acid molecule of the present invention) in any HIV-1 strain may be easily identified, for example by aligning the nucleotide sequence of a given HIV-1 strain with the nucleotide sequence of reference HIV-1 clone pNL4-3 (e.g., using a software for sequence alignment such as Clustal W). It will be understood that the corresponding sequences in other HIV-1 strains may not be identical to the corresponding sequence of HIV-1 clone pNL4-3 (e.g., the sequence in other HIV-1 strains may be 75, 80, 85, 90 or 95% identical to the corresponding sequence of HIV-1 clone pNL4-3), and that the sequence of the antisense nucleic acid molecule may be adapted accordingly. FIG. 6A depicts an alignment of the sequences of different HIV strains/subtypes, and shows for example that nucleotides 1497 to 1521 correspond to nucleotides 1075 to 1099 in HIV strain Mal, and nucleotides to 1488 to 1512 in HIV strain Indie-C1. In an embodiment, the antisense nucleic acid molecule directed against a sequence corresponding to about nucleotide 1498 to about nucleotide 1518 of HIV-1 clone pNL4-3.

In an embodiment, the antisense nucleic acid molecule comprises a sequence that can hybridize, under stringent conditions or highly stringent conditions, with the above-mentioned sequence corresponding to about nucleotide 1495 to about nucleotide 1526 of HIV-1 clone pNL4-3, or a fragment thereof (e.g., a fragment of at least 5, 10, 15 or 20 nucleotides located with the region defined), or the complementary sequence thereof, or a corresponding sequence with at least 75, 80, 85, 90 or 95% identity or complementarity in another HIV-1 strain. Hybridization technology is well-known in the field of molecular biology. For the purpose of illustration, the hybridization condition is a stringent condition, for example, a DNA binding to the filtration membrane is hybridized in 6× sodium chloride/sodium citrate (SSC) at about 45° C. or more, then is washed one or more times in 0.2×SSC/0.1% SDS at about 50-65° C.; or is a highly stringent condition, for example, a nucleic acid binding to the filtration membrane is hybridized in 6×SSC at about 45° C., then is washed one or more times in 0.1×SSC/0.2% SDS at about 68° C.; or is other stringent hybridization conditions known in the art (See for example, Ausubel, F. M. et al., 1989, Current Protocols in Molecular Biology, Volume 1, Green Publishing Associates, Inc. and John Wiley & Sons, Inc., New York, page 6.3.1-6.3.6 and 2.10.3).

In an embodiment, the antisense nucleic acid comprises a sequence that is fully complementary to the target sequence (or a fragment thereof) over the entire length of the oligonucleotide. In certain embodiments, oligonucleotides are 99% complementary to the target sequence (or a fragment thereof). In certain embodiments, the antisense nucleic acid comprises a sequence that is at least 95% complementary to the target sequence (or a fragment thereof). In certain embodiments, the antisense nucleic acid comprises a sequence that is at least 90% complementary to the target sequence (or a fragment thereof). In certain embodiments, the antisense nucleic acid comprises a sequence that is at least 85% complementary to the target sequence (or a fragment thereof). In certain embodiments, the antisense nucleic acid comprises a sequence that is at least 80% complementary to the target sequence (or a fragment thereof). In certain embodiments, an antisense compound comprises a region that is fully complementary to a target nucleic acid and is at least 80% complementary to the target nucleic acid over the entire length of the oligonucleotide. In certain such embodiments, the region of full complementarity is from about 6 to about 14 nucleotides in length.

In an embodiment, the antisense nucleic acid molecule directed against a sequence corresponding to about nucleotide 1497 to about nucleotide 1521 of HIV-1 clone pNL4-3. In another embodiment, the antisense nucleic acid molecule directed against a sequence corresponding to about nucleotide 1495 to about nucleotide 1524 of HIV-1 clone pNL4-3. In another embodiment, the antisense nucleic acid molecule directed against a sequence corresponding to about nucleotide 1496 to about nucleotide 1526 of HIV-1 clone pNL4-3. In another embodiment, the antisense nucleic acid molecule directed against a sequence corresponding to about nucleotide 1495 to about nucleotide 1520 of HIV-1 clone pNL4-3.

The term "antisense nucleic acid molecule" as used herein refers to any nucleic acid molecule, such as a short RNA molecule, capable of inhibiting the expression of a target polypeptide by, for example, inducing degradation of a RNA molecule encoding the target polypeptide, blocking its translation and/or stopping its replication, and includes for example microRNA (miRNA), decoys, aptamers, small nuclear (sn) RNAs, ribozyme, antisense oligonucleotides (ASONs), small interfering (si) and short hairpin (sh) RNAs. An antisense nucleic acid molecule comprises or consists of an oligonucleotide at least a portion of which is complementary to the target sequence to which it is capable of hybridizing under physiological conditions. The antisense nucleic acid molecule according to the present invention may comprise modified products produced by chemically modifying the constitution moieties, such as phosphate backbone and/or ribose and/or base etc., of the molecule. The modification methods are known in the art, which can be thio-modification and/or sterol modification and/or PEG-modification and/or glyco-modification and/or LNA-modification etc., as described for example in Dykxhoorn D M et al., *Annual Review of Biomedical Engineering*, 2006, Volume 8: pages 377-402 and Behlke M A et al., *Molecular Therapy*, 2006, Volume 13: pages 644-670.

The antisense nucleic acid molecules described herein, may be chemically modified, for example to change (e.g., increase or decrease) intracellular stability and half-life. Such modified are herein referred to as "analogs". Possible modifications include the addition of flanking sequences at the 5' and/or 3' ends of the molecule or the use of phosphorothioate (also known as thiophosphate) linkages rather than phosphodiesterase linkages within the backbone of the molecule. In addition, one or more ribose groups may be modified to add a methyl moiety to the 2'-OH to form a 2'-methoxy moiety (referred to as 2'O-methyl-modified). Also, the 2'-OH moiety can be linked to the 3' or 4'-carbon of ribose by a methylene or ethylene linker, typically a methylene linker to the 4'-carbon, to form a "locked nucleic acid" (see WO 98/39352 and WO 99/14226).

In certain embodiments, chemical modification also includes the use of nontraditional bases such as inosine, queosine, and wybutosine, as well as acetyl-, methyl-, thio-, and other similarly modified forms of adenine, cytidine, guanine, thymine, and uridine, which are not as easily recognized by endogenous endonucleases. Examples of modified bases include uridine and/or cytidine modified at the 5-position, e.g., 5-(2-amino)propyl uridine, 5-bromo uridine; adenosine and/or guanosines modified at the 8 position, e.g., 8-bromo guanosine; deaza nucleotides, e.g., 7-deaza-adenosine; and O- and N-alkylated nucleotides, e.g., N6-methyl adenosine. "Analogs" also include sequences in which one or more thymine (T) bases have been substituted for uracil (U) base and vice versa.

In certain embodiments, the sugar moiety can be modified, typically at the 2'-OH of ribose. Examples of such modifications include instances where the 2'—OH group is replaced by a group selected from H, OR, R, halo, SH, SR, $NH_2$, NHR, $NR_2$ or ON, where R is C1-C6 alkyl, alkenyl or alkynyl and halo is F, Cl, Br or I.

Further, chemical modification can encompass modified backbones such as morpholino and/or further non-natural internucleoside linkages such as siloxane, sulfide, sulfoxide, sulfone, sulfonate, sulfonamide, and sulfamate; formacetyl and thioformacetyl; alkene-containing; methyleneimino and methylenehydrazino; amide, and the like.

One or more nucleotides (or linkages) within the sequences described herein can be modified. For example, a 20-mer oligonucleotide may contain 1, 2, 3, 4, 5, 6, 7, 8, 9, 10, 11, 12, 13, 14, 15, 16, 17, 18, 19 or 20 modified nucleotides.

In an embodiment, the above-mentioned antisense nucleic acid molecule is from about 5 to about 100 nucleotides in length, in further embodiments from about 10 to about 100, from about 5 to about 50, from about 10 to about 50, from about 15 to about 50, from about 10 to about 30, from about 18 to about 29, from about 19 to about 27, from about 18 to about 25, from about 19 to about 25, or from about 19 to about 23, nucleotides in length.

In an embodiment, the antisense nucleic acid molecule is a ribozyme. The term "ribozyme" refers to enzymatic RNA molecules capable of catalyzing the specific cleavage of a target RNA. The mechanism of ribozyme action involves sequence specific hybridization of the ribozyme molecule to complementary target RNA, followed by an endonucleolytic cleavage. The ribozyme comprises one or more sequences complementary to the sequence corresponding to about nucleotide 1495 to about nucleotide 1526 (e.g., 1497 to 1521) of HIV-1 clone pNL4-3 and decreases the level of the HIV-1 Gag polyprotein and/or of one or more of its processing products, such as capsid (CA). Examples of ribozymes include, for example, Hairpin ribozyme, Hammerhead ribozyme, VS ribozyme, glmS ribozyme and delta ribozyme derived from the genome of hepatitis delta virus (HDV ribozyme). In an embodiment, the ribozyme is HDV ribozyme.

Figure 1B:
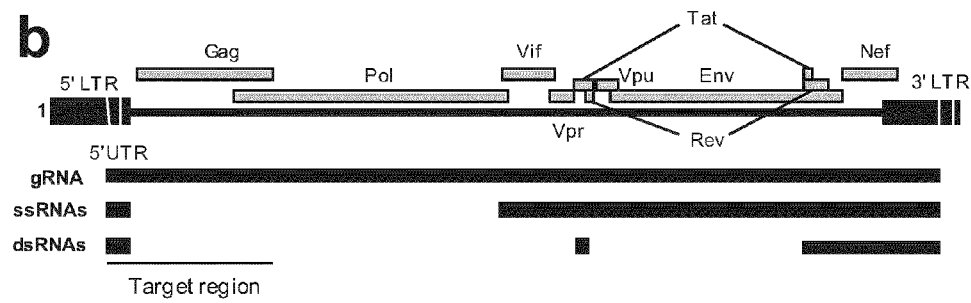
FIG. 1B: the full length genomic (g), singly-spliced (ss) and doubly-spliced (ds) RNA species of HIV-1 are illustrated. Reading frames for all HIV-1 proteins are shown above the different RNAs and the 5' region, used to identify SOFA-HDV-Rz target sites, is underlined.

In an embodiment, the ribozyme comprises a specific On/Off Adaptor (SOFA) module, as described for example in PCT publication No. WO 2006/002547. Such module, which comprises a SOFA blocker (BI) and SOFA biosensor (Bs), is useful to increase the specificity of the ribozyme by increasing the length of the recognition sequence, enabling the ribozyme only in the presence of the target RNA substrate. As shown in FIG. 1B, in the OFF conformation (in the absence of the target RNA), the SOFA blocker (BI) base pairs with the last 4 nts of the recognition domain (RD). When the SOFA biosensor (Bs) base pairs with a specific target sequence, the RD is released from the BI sequence and binds at 3 to 5 nts upstream from the Bs binding site in the ON conformation. The first nt in the target site (n+1) must be a G, forming a wobble base pair with the U in RD. The cleavage site is indicated with an arrow.

Thus, in an embodiment, the ribozyme comprises (i) a first domain (recognition domain, RD) of, e.g., about 7 nucleotides comprising a sequence that is complementary to a first sequence within the sequence corresponding to about nucleotide 1495 to about nucleotide 1526 of HIV-1 clone pNL4-3; (ii) a second domain (SOFA biosensor, Bs) of, e.g., about 5 to about 15 nucleotides, comprising a sequence that is complementary to a second sequence (different from the first sequence) within the sequence corresponding to about nucleotide 1495 to about nucleotide 1526 of HIV-1 clone pNL4-3 and (iii) a third domain (SOFA blocker, BI) of, e.g., about 3 to about 5 nucleotides (preferably 4 nucleotides), comprising a sequence that is complementary to a sequence of the recognition domain (in an embodiment the last 3 to 5 nucleotides from the RD). In an embodiment, the first and second sequences (within the sequence corresponding to about nucleotide 1495 to about nucleotide 1526 of HIV-1 clone pNL4-3 (i.e. the target RNA) are spaced apart by at least 1 nucleotide, and preferably by about 1 to about 5 nucleotides (referred to as the "spacer" in FIG. 1B).

In an embodiment, the RD comprises a sequence that is complementary to a sequence corresponding to about nucleotide 1498 to about nucleotide 1504 of HIV-1 clone pNL4-3.

In an embodiment, the Bs comprises a sequence that is complementary to a sequence corresponding to about nucleotide 1509 to about nucleotide 1518 of HIV-1 clone pNL4-3.

In an embodiment, the BI comprises a sequence corresponding to about nucleotide 1501 to about nucleotide 1504 of HIV-1 clone pNL4-3.

In an embodiment, the ribozyme comprises: a recognition domain (RD) comprising/consisting of the sequence TTCCTGT, a biosensor (Bs) domain comprising/consisting of the sequence AAGGGTACTA, and a blocker (BI) domain comprising/consisting of the sequence GGAA.

In an embodiment, the ribozyme comprises or consists of the following sequence:

(SEQ ID NO: 142)
GGGCCAGCTAGTTTAAGGGTACTAGGAACAGGGTCCACCTCCTCGCGGT

TTCCTGTGGGCATCCGTTCGCGGATGGCTAAGGGACCCTTTCTAGCTGG.

In an embodiment, the antisense nucleic acid molecule is an RNA interference agent. In an embodiment, the antisense nucleic acid molecule is a small/short interfering RNA (siRNA) molecule, i.e. a double-stranded (ds) RNA that preferably contains about 19 to 23 base pairs. The siRNA molecules may contain 3' overhangs, such as a 1- to 5-nucleotide (e.g., 2-nucleotide) 3' overhang in one or both strands. In an embodiment, the overhang is a 3'UU or 3'TT overhang. siRNAs, which are typically chemically synthesized, may be transfected directly into the cytosol of cells.

In an embodiment, the siRNA comprises or consists of one of the following pair of sequences (i) to (iv):

(i)
si1497 sense:
(SEQ ID NO: 75)
AGCAGGAACUACUAGUACCCUUCdAdG si1497 antisense:
(SEQ ID NO: 76)
UAUCGUCCUUGAUGAUCAUGGGAAGUC;

(ii)
si1498 sense:
(SEQ ID NO: 77)
GCAGGAACUACUAGUACCCUUCAdGdG si1498 antisense:
(SEQ ID NO: 78)
AUCGUCCUUGAUGAUCAUGGGAAGUCC;

(iii)
si1499 sense:
(SEQ ID NO: 81)
CAGGAACUACUAGUACCCUUCAGdGdA si1499 antisense:
(SEQ ID NO: 82)
UCGUCCUUGAUGAUCAUGGGAAGUCCU;
or (iv)
si1498-27 sense:
(SEQ ID NO: 79)
GCAGGAACUACUAGUACCCUUCAGGAA si1498-27 antisense:
(SEQ ID NO: 80)
dAdTCGUCCUUGAUGAUCAUGGGAAGUCCUU;

or an analog thereof.

In an embodiment, the antisense nucleic acid molecule is a short hairpin RNA (shRNA) molecule, which typically comprises two complementary 19-22 bp RNA sequences linked by a short loop of 4-11 nt similar to the hairpin found in naturally occurring miRNA. Expression of shRNA in cells can be obtained by delivery of plasmids or through viral or bacterial vectors.

In an embodiment, the shRNA is encoded by a nucleic acid comprising or consisting of one of the following stem sequences (i) to (xii):

(i)
(SEQ ID NO: 93)
5'-GCAGGAACTACTAGTACCCT-3'

(SEQ ID NO: 118)
3'-CGTCCTTGATGATCATGGGA-5';

(ii)
(SEQ ID NO: 87)
5'-ATAGCAGGAACTACTAGTAC-3'

(SEQ ID NO: 119)
3'-TATCGTCCTTGATGATCATG-5';

(iii)
(SEQ ID NO: 89)
5'-TAGCAGGAACTACTAGTACC-3'

(SEQ ID NO: 120)
3'-ATCGTCCTTGATGATCATGG-5';

(iv)
(SEQ ID NO: 91)
5'-AGCAGGAACTACTAGTACCC-3'

(SEQ ID NO: 121)
3'-TCGTCCTTGATGATCATGGG-5';

(v)
(SEQ ID NO: 95)
5'-CAGGAACTACTAGTACCCTT-3'

(SEQ ID NO: 122)
3'-GTCCTTGATGATCATGGGAA-5';

(vi)
(SEQ ID NO: 99)
5'-GGAACTACTAGTACCCTTCA-3'

(SEQ ID NO: 123)
3'-CCTTGATGATCATGGGAAGT-5';

(vii)
(SEQ ID NO: 105)
5'-GCAGGAACTACTAGTACCC-3'

(SEQ ID NO: 124)
3'-CGTCCTTGATGATCATGGG-5';

(viii)
(SEQ ID NO: 107)
5'-GCAGGAACTACTAGTACCCTT-3'

(SEQ ID NO: 125)
3'-CGTCCTTGATGATCATGGGAA-5';

(ix)
(SEQ ID NO: 109)
5'-GCAGGAACTACTAGTACCCTTCA-3'

(SEQ ID NO: 126)
3'-CGTCCTTGATGATCATGGGAAGT-5';

(x)
(SEQ ID NO: 111)
5'-GCAGGAACTACTAGTACCCTTCAGG-3'

(SEQ ID NO: 127)
3'-CGTCCTTGATGATCATGGGAAGTCC-5';

(xi)
(SEQ ID NO: 113)
5'-GCAGGAACTACTAGTACCCTTCAGGAA-3'

(SEQ ID NO: 128)
3'-CGTCCTTGATGATCATGGGAAGTCCTT-5';
or (xii)
(SEQ ID NO: 115)
5'-GCAGGAACTACTAGTACCCTTCAGGAACA-3'

(SEQ ID NO: 129)
3'-CGTCCTTGATGATCATGGGAAGTCCTTGT-5';

or an analog thereof.

In an embodiment, the shRNA molecules may contain 3' overhangs, such as a 1- to 5-nucleotide (e.g., 2-nucleotide) 3'-overhang in one or both strands. In an embodiment, the overhang is a 3'UU or 3'TT overhang. In an embodiment, the shRNA comprises a loop of about 4-11 nucleotides, in further embodiments about 6-10 nucleotides or about 7-9 nucleotides. In an embodiment, the loop comprises or consists of the sequence CTCGAG. In another embodiment, the loop comprises or consists of one of the following sequences: GCTCGAGG, ACTCGAGA, TCTCGAGT or CCTCGAGC.

In an embodiment, the shRNA is encoded by a nucleic acid comprising one of the following sequences (i) to (xii):

(i)
(SEQ ID NO: 130)
GCAGGAACTACTAGTACCCTACTCGAGAAGGGTACTAGTAGTTCCTGCTT;

(ii)
(SEQ ID NO: 131)
ATAGCAGGAACTACTAGTACGCTCGAGGGTACTAGTAGTTCCTGCTATTT;

(iii)
(SEQ ID NO: 132)
TAGCAGGAACTACTAGTACCGCTCGAGGGGTACTAGTAGTTCCTGCTATT;

(iv)
(SEQ ID NO: 133)
AGCAGGAACTACTAGTACCCACTCGAGAGGGTACTAGTAGTTCCTGCTTT;

(v)
(SEQ ID NO: 134)
CAGGAACTACTAGTACCCTTGCTCGAGGAAGGGTACTAGTAGTTCCTGTT;

(vi)
(SEQ ID NO: 135)
GGAACTACTAGTACCCTTCACCTCGAGCTGAAGGGTACTAGTAGTTCCTT;

(vii)
(SEQ ID NO: 136)
GCAGGAACTACTAGTACCCACTCGAGAGGGTACTAGTAGTTCCTGCTT;

(viii)
(SEQ ID NO: 137)
GCAGGAACTACTAGTACCCTTGCTCGAGGAAGGGTACTAGTAGTTCCTGCTT;

(ix)
(SEQ ID NO: 138)
GCAGGAACTACTAGTACCCTTCACCTCGAGCTGAAGGGTACTAGTAGTTCCTGCTT;

(x)
(SEQ ID NO: 139)
GCAGGAACTACTAGTACCCTTCAGGTCTCGAGTCCTGAAGGGTACTAGTAGTTCCTGCTT;

(xi)
(SEQ ID NO: 140)
GCAGGAACTACTAGTACCCTTCAGGAAGCTCGAGGTTCCTGAAGGGTACTAGTAGTTCCTGCTT;
or (xii)
(SEQ ID NO: 141)
GCAGGAACTACTAGTACCCTTCAGGAACATCTCGAGTTGTTCCTGAAGGGTACTAGTAGTTCCTGCTT;

or an analog thereof.

Reagents and kits for performing RNA interference are available commercially from for example Ambion® Inc. (Austin, Tex., USA), New England Biolabs® Inc. (Beverly, Mass., USA), Sigma-Aldrich® and Invitrogen® (Carlsbad, Calif., USA)

In another aspect, the present invention provides a nucleic acid molecule (e.g., DNA) comprising a sequence encoding the antisense nucleic acid molecule.

In another aspect, the present invention provides a vector or plasmid, such as a recombinant expression vector or plasmid, comprising the above-mentioned nucleic acid molecule (e.g., DNA). The nucleic acid molecule (e.g., DNA) comprising a sequence encoding the antisense nucleic acid molecule may be operably linked with expression controlling sequences, thereby making it possible to express the antisense nucleic acid molecule in a cell, for example a mammalian cell such as a human cell. In an embodiment, the vector is a viral vector, for example a retroviral vector, a lentiviral vector, or other vectors such as adenoviral vectors or adeno-associated vectors (AAV).

In another aspect, the present invention provides a cell (e.g., an isolated or recombinant cell) comprising the above-mentioned antisense nucleic acid molecule, nucleic acid molecule (e.g., DNA) comprising a sequence encoding the antisense nucleic acid molecule, and/or vector or plasmid. The cell can be in an isolated (or ex vivo) form, such as a cell isolated from a HIV-infected patient or a normal individual, or in vivo, or a cell strain cultured in vitro. The antisense nucleic acid molecule, nucleic acid molecule (e.g., DNA) comprising a sequence encoding the antisense nucleic acid molecule, and/or vector or plasmid may be introduced in the cell either in vitro or in vivo, by known methods such as transformation, transduction, transfection, and infection, such as calcium phosphate or calcium chloride co-precipitation-mediated transfection, DEAE-dextran-mediated transfection, liposome-mediated transfection, electroporation, microinjection and the like. Additionally, as noted above, the antisense nucleic acid molecule, and/or vector or plasmid may be introduced into a cell using a viral vector such as those derived from adenovirus, adeno-associated virus and lentivirus. Details of these and other techniques are known in the art, for example, as described in J. Sambrook and D. W. Russell, Molecular Cloning: A Laboratory Manual, Cold Spring Harbor Laboratory Press; 3rd Ed., 2001; F. M. Ausubel, Ed., Short Protocols in Molecular Biology, Current Protocols; 5th Ed., 2002; and Engelke, D. R., RNA Interference (RNAi): Nuts and Bolts of RNAi Technology, DNA Press LLC, Eagleville, P A, 2003.

In another aspect, the present invention provides a composition (e.g., a pharmaceutical composition) comprising (i) the above-mentioned antisense nucleic acid molecule, nucleic acid molecule (e.g., DNA) comprising a sequence encoding the antisense nucleic acid molecule, vector/plasmid and/or cell and (ii) a carrier/excipient (e.g., a pharmaceutically acceptable carrier/excipient).

Compositions and methods for the formulation of pharmaceutical compositions depend on a number of criteria, including, but not limited to, route of administration, extent of disease, or dose to be administered.

Pharmaceutical compositions comprising antisense compounds encompass any pharmaceutically acceptable salts, esters, or salts of such esters. In certain embodiments, pharmaceutical compositions comprising antisense compounds comprise one or more oligonucleotide, which upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an oligomeric compound, which are cleaved by endogenous nucleases within the body, to form the active antisense oligomeric compound.

Lipid moieties have been used in nucleic acid therapies in a variety of methods. In certain such methods, the nucleic acid is introduced into preformed liposomes or lipoplexes made of mixtures of cationic lipids and neutral lipids. In certain methods, DNA complexes with mono- or polycationic lipids are formed without the presence of a neutral lipid. In certain embodiments, a lipid moiety is selected to increase distribution of a pharmaceutical agent to a particular cell or tissue.

In certain embodiments, pharmaceutical compositions provided herein comprise one or more antisense compounds and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, a pharmaceutical composition provided herein comprises a delivery system.

Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition provided herein comprises one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, a pharmaceutical composition provided herein is prepared for oral administration. In certain embodiments, pharmaceutical compositions are prepared for buccal administration.

In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

In certain embodiments, a pharmaceutical composition is prepared for transmucosal administration. In certain of such embodiments penetrants appropriate to the barrier to be permeated are used in the formulation. Such penetrants are generally known in the art.

In certain embodiments, a pharmaceutical composition provided herein comprises an antisense molecule in a therapeutically effective amount. In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In certain embodiments, the antisense molecule provided herein is formulated as a prodrug. In certain embodiments, upon in vivo administration, a prodrug is chemically converted to the biologically, pharmaceutically or therapeutically more active form of the antisense molecule.

In certain embodiments, the present invention provides compositions and methods for reducing the amount or activity of a target nucleic acid in a cell. In certain embodiments, the cell is in an animal. In certain embodiments, the animal is a mammal. In certain embodiments, the animal is a rodent. In certain embodiments, the animal is a primate. In certain embodiments, the animal is a non-human primate. In certain embodiments, the animal is a human.

In certain embodiments, the present invention provides methods of administering a pharmaceutical composition comprising an antisense molecule of the present invention to an animal. Suitable administration routes include, but are not limited to, oral, rectal, transmucosal, intestinal, enteral, topical, suppository, through inhalation, intrathecal, intracerebroventricular, intraperitoneal, intranasal, intraocular, and parenteral (e.g., intravenous, intramuscular, intramedullary, and subcutaneous).

The above-mentioned antisense nucleic acid molecule, nucleic acid molecule (e.g., DNA) comprising a sequence encoding the antisense nucleic acid molecule, vector/plasmid, cell and/or compositions according to the present invention can be used to inhibit HIV-1 replication in a cell or a subject in need thereof, and/or prevent or treat HIV-1 infection (and/or Acquired Immune Deficiency Syndrome, AIDS as well as AIDS-related diseases, such as opportunistic infections, Kaposi's sarcoma or pneumocystic pneumonia) in a subject.

The term "treating" as used herein, includes but is not limited to, reducing, suppressing, inhibiting, lessening, or affecting the progression, severity, and/or scope of a condition, chance of re-occurrence or returning of a disease after a remission. In one embodiment, treating may include directly affecting or curing, suppressing, inhibiting, reducing the severity of, delaying the onset of, reducing symptoms associated with HIV-1 infection, or a combination thereof. In another embodiment, treating includes delaying progression, expediting remission, inducing remission, augmenting remission, speeding recovery, increasing efficacy of or decreasing resistance to alternative therapeutics, or a combination thereof. In an embodiment, "treating" means to ameliorate at least one clinical symptom or parameter of HIV infection or preventing it from worsening or preventing the transmission of HIV, e.g., from mother to child. For example, a treatment can result in a reduction in viral load, and/or an increase in number of $CD4^+$ T cells ("CD4 count").

The term "preventing," as used herein, includes but is not limited to, delaying the onset of symptoms, preventing relapse to a disease, decreasing the number or frequency of relapse episodes, increasing latency between symptomatic episodes, or a combination thereof.

An "effective amount" is an amount sufficient to effect a desired therapeutic effect, e.g., a reduction in viral load, and/or an increase in number of $CD4^+$ T cells. An effective amount can be administered in one or more administrations, applications or dosages. A therapeutically effective amount of a composition may depend on the composition selected. The compositions can be administered once, one or more times per day, and/or one or more times per week; including once every other day. In certain embodiments, the compositions will be administered two or three times per day. The skilled artisan will appreciate that certain factors may influence the dosage and timing required to treat effectively a subject, including but not limited to the severity of the disease or disorder, previous treatments, the general health and/or age of the subject, and any other indications present.

Treatment of a subject with an effective amount of an antisense nucleic acid described herein can include a single treatment or a series of treatments.

Dosage, toxicity and therapeutic efficacy of the antisense nucleic acids can be determined, e.g., by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Antisense nucleic acids that exhibit high therapeutic indices are preferred. While compounds that exhibit toxic side effects may be used, care should be taken to select a dose and administration schedule that minimizes severe side effects while maximizing therapeutic efficacy.

The data obtained from cell culture assays and animal studies can be used in formulating a range of dosage for use in humans. The dosage of such antisense nucleic acids lies preferably within a range of circulating concentrations that include the $ED_{50}$ with little or no toxicity. The dosage may vary within this range depending upon the dosage form employed and the route of administration utilized. For any antisense nucleic acid used in a method described herein, an effective dosage range can be estimated initially from cell culture assays. A dose can be further formulated in animal models to achieve a circulating plasma concentration range that includes the $IC_{50}$ (i.e., the concentration of the test compound that achieves a half-maximal inhibition of symptoms) as determined in cell culture. Such information can be used to determine more accurately useful doses in humans. Levels in plasma may be measured, for example, by high performance liquid chromatography (HPLC).

In an embodiment, the antisense nucleic acid molecule, nucleic acid molecule (e.g., DNA) comprising a sequence encoding the antisense nucleic acid molecule, vector/plasmid, cell and/or compositions according to the present invention further comprises a targeting moiety, i.e. to target antisense nucleic acid molecule to HIV-infected cells or tissues. For example, the antisense nucleic acid molecule, nucleic acid molecule (e.g., DNA) comprising a sequence encoding the antisense nucleic acid molecule, vector/plasmid, cell and/or compositions may comprise a moiety targeting CD4+ T cells, macrophages and/or dendritic cells. Such moiety may be a ligand (natural ligand, antibody, RNA/DNA aptamer) that recognizes a marker (e.g., cell surface marker) expressed by HIV-infected cells.

In an embodiment, the antisense nucleic acid molecule, nucleic acid molecule (e.g., DNA) comprising a sequence encoding the antisense nucleic acid molecule, vector/plasmid, cell and/or compositions according to the present invention is used in combination with one or more additional anti-HIV agents

MODE(S) FOR CARRYING OUT THE INVENTION

The present invention is illustrated in further details by the following non-limiting examples.

EXAMPLE 1

Materials and Methods

Identification of SOFA-HDV-Rz Target Sites.

Figure 2A:
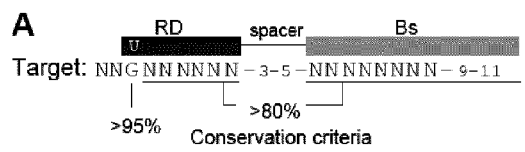
FIGS. 2A to C show the SOFA-HDV-Rz target site identification.

The use of the LANL dataset to estimate sequence conservation at the nt level has been previously described[45]. Briefly, a multiple sequence alignment of all complete HIV-1 sequences were downloaded from the LANL database using the QuickAlign™ tool and a consensus sequence with % conservation at each position was generated using Jalview sequence editor[47] and exported to Microsoft Excel (see reference 51). Several positions in the consensus sequence were represented in only a small number of sequences and positions that occurred in less than 10% of the sequences were removed from the raw data to facilitate target site selection. Highly conserved target sites were selected based on criteria illustrated in FIG. 2A. Nucleotide BLAST[48] was then used to align target sites to HIV-1 NL4-3 (M19921) and Ribosubstrates software[26] was used to evaluate the potential for the corresponding SOFA-HDV-Rzs to target human RNAs as previously described[26]. Briefly, the software identifies potential target sites for SOFA-HDV-Rzs in a cDNA database allowing for variations in the length of the spacer sequence and biosensor (FIG. 1A). Perfectly matched target sites are assigned a value of 0, and the score increases by 10 for each wobble base pair and by 100 for each mismatch. We set a value of 20 as the cut-off for potential off-target effects, representing at least two wobble base pairs between a SOFA-HDV-Rz targeting HIV-1 RNA and a potential target site in any human RNA.

Plasmid Constructs

All SOFA-HDV Rzs and shRNAs were expressed from the human RNaseP H1 promoter in the vector psiRNA-H1GFP::Zeo (InvivoGen, San Diego, Calif.). SOFA-HDV-Rz inserts were generated using an overlapping PCR strategy[11,14,28] and shRNA inserts were generated by annealing complementary oligonucleotides. Sequences for shRNA522 and shRNA553 inserts were obtained from a previous study[22] and using an identical design, shRNAns (non-sense, adapted from siControl[20]), shRNA5983 (adapted from sh1[49]) and shRNA1498 inserts were designed. The cloning strategies and sequences of all oligonucleotides used for the generation of plasmid inserts are provided below, variable SOFA-HDV-Rz DNA sequences are illustrated in Table 5. SOFA-HDV-Rz inserts were generated by PCR using DNA primers A and B (2 μM), C and D (25 nM):

TABLE 1

Sequences of DNA primers A to D used to generate SOFA-HDV-Rz inserts

| Name | Sequence (5'-3') | SEQ ID NO |
|------|------------------|-----------|
| A | TATAAGTTCTGTATGAGTTCACGGAAGACCGACCT↓CGGGCCAGCTAGTTT | 9 |
| B | CAACAACAGTGITCGGATGAACTGATGCTATGAAGACTCCAAA↓AACCAGCTAGAAAGGGTC | 10 |

TABLE 1-continued

Sequences of DNA primers A to D used to generate SOFA-HDV-Rz inserts

| Name | Sequence (5'-3') | SEQ ID NO |
|---|---|---|
| C | CCAGCTAGAAAGGGTCCCTTAgCCATCC<u>GCGAACGGATGCCC</u> | 11 |
| D | TAATACGACTCACTATAGGGCCAGCTAGTTT(Bs)(BI)CAGGGTCCACCTCCTCGCGGT(RD)<u>GGGCATCCGTTCGCG</u> | 12 |

Primers A and B include BbsI recognition sites (bold, cut site indicated with an arrow), C and D contain a common reverse and specific forward ribozyme sequence respectively (overlapping sequences underlined). The nucleotide in primer C that was mutated to produce a catalytically inactive SOFA-HDV Rz is shown as lower case (G to T mutation in this study). Variable Bs, BI and RD sequences in primer D are shown in Table 1 for each SOFA-HDV-Rz evaluated.

shRNA inserts were generated by annealing complementary sense (S) and antisense (AS) oligonucleotides (1.25 μM each in 75 mM NaCl, 40 μL, 2 min at 80° C., cooled to 37° C.):

TABLE 2

Sequences of shRNA inserts

| Name | Sequence (5'-3') | SEQ ID NO |
|---|---|---|
| shRNA522 S | <u>ACCT</u>CGCCTCAATAAAGCTTGCCTTCCTCGAGCAAGGCAAGCTTTATTGAGGCTT | 13 |
| shRNA522 AS | <u>CAAAA</u>AGCCTCAATAAAGCTTGCCTTGCTCGAGGAAGGCAAGCTTTATTGAGGCG | 14 |
| shRNA553 S | <u>ACCT</u>CGTAGTGTGTGCCCGTCTGTTCCTCGAGCAACAGACGGGCACACACTACTT | 15 |
| shRNA553 AS | <u>CAAAA</u>AGTAGTGTGTGCCCGTCTGTTGCTCGAGGAACAGACGGGCACACACTACG | 16 |
| shRNAns S | <u>ACCT</u>CGTACCGCACGTCATTCGTATCCTCGAGCATACGAATGACGTGCGGTACTT | 17 |
| shRNAns AS | <u>CAAAA</u>AGTACCGCACGTCATTCGTATGCTCGAGGATACGAATGACGTGCGGTACG | 18 |
| shRNA1498 S | <u>ACCT</u>CGCAGGAACTACTAGTACCCTACTCGAGAAGGGTACTAGTAGTTCCTGCTT | 19 |
| shRNA1498 AS | <u>CAAAA</u>AGCAGGAACTACTAGTACCCTTCTCGAGTAGGGTACTAGTAGTTCCTGCG | 20 |
| shRNA5983 S | <u>ACCT</u>CGCGGAGACAGCGACGAAGAGGCTCGAGGCTCTTCGTCGCTGTCTCCGCTT | 21 |
| shRNA5983 AS | <u>CAAAA</u>AGCGGAGACAGCGACGAAGAGCCTCGAGCCTCTTCGTCGCTGTCTCCGCG | 22 |

The nucleotides flanking the core loop sequence (bold) for the HIV-1 specific shRNA522, shRNA553 and shRNA1498 are complementary to the 21$^{st}$ nt of their target site in case of differential processing as previously described[22]. Bbsl cut site overhangs in the complementary oligonucleotides are underlined.

SOFA-HDV-Rz and shRNA inserts were ligated into Bbsl (Thermo Fischer Scientific, Waltham, Mass.) digested psiRNA-H1GFP::Zeo (InvivoGen, San Diego, Calif.) expression plasmid. All constructs were confirmed by sequencing using a primer located in the H1 promoter: 5'-TCTACGGGGTCTGACGC-3' (SEQ ID NO:23)

siRNA Oligonucleotides siRNAs were custom made by Dharmacon® with the sequences depicted in Table 3:

TABLE 3

Sequences of siRNAs

| Name | Sequence (5'-3') | SEQ ID NO |
|---|---|---|
| si1497 sense | AGCAGGAACUACUAGUACCCUUCdAdG | 24 |
| si1497 antisense | UAUCGUCCUUGAUGAUCAUGGGAAGUC | 25 |
| si1498 sense | GCAGGAACUACUAGUACCCUUCAdGdG | 26 |
| si1498 antisense | AUCGUCCUUGAUGAUCAUGGGAAGUCC | 27 |
| si1499 sense | CAGGAACUACUAGUACCCUUCAGdGdA | 28 |
| si1499 antisense | UCGUCCUUGAUGAUCAUGGGAAGUCCU | 29 |
| siNS sense | GUACCGCACGUCAUUCGUAUCCUdAdT | 30 |
| siNS antisense | TTCAUGGCGUGCAGUAAGCAUAGGAUA | 31 |

Transfections

Co-transfections of HIV-1 molecular clones with Rz or shRNA expressing plasmids were performed in either 24 or 12 well plate formats as indicated in the figure legends. 24 h prior to transfection, HEK293T cells were plated at 2×10$^5$ cells/mL and transfections were carried out using using TransiT® reagent (Mirus, Madison, Wis.) according to the manufacturers instructions. Viral production was estimated 48 h following transfection by measuring HIV-1 RT activity in the culture supernatant. To account for differences in viral production between experiments, replicates for each construct evaluated were performed in parallel with the empty vector psiRNA-H1GFP::Zeo and all data are expressed as a percentage of viral production in the empty vector co-transfected cells (Relative RT activity). For each Rz or shRNA construct evaluated we also included the irrelevant control SOFA-HDV-Rz-HBV or the nonsense control shRN-Ans, respectively.

Cell Culture

HEK293T and TZM-bl cells were maintained in Dulbec-co's modified Eagle's medium with high glucose (Hyclone, Logan, Utah) supplemented with 10% fetal bovine serum (Hyclone, Logan, Utah), 50 U/mL Penicillin and 50 µg/mL Streptomycin (Life Tech., Carlsbad, Calif.). Jurkat T cells were maintained in Roswell Park Memorial Institute (RPMI) 1640 (Hyclone, Logan, Utah) supplemented with 10% heat inactivated (55° C., 30 min) fetal bovine serum (Hyclone, Logan, Utah), 50 U/mL Penicillin and 50 µg/mL Strepto-mycin (Life Tech., Carlsbad, Calif.).

Rz Expression in HEK293T Cells

Total RNA extracts were harvested from transfected cells using Trizol reagent (Life Tech., Carlsbad, Calif.) according to the manufacturers instructions. 10 µg of total RNA was resolved on an 8% denaturing polyacrylamide gel, transferred to a nylon membrane (Amersham Hybond-N+, GE Healthcare, Little Chalfont, UK) and UV cross-linked. Membranes were incubated with ProbeSOFA followed by Probe5S and visualized using a Phosphor screen. Probe sequences, labelling and details on the Northern blot conditions are provided below.

Northern Blot

Probe labeling and sequences: 5 pmol of the oligonucleotide ProbeSOFA or 10 pmol of the oligonucleotide Probe5S were 5'-end labeled by incubation for 1 h at 37° C. with 3 U of T4 polynucleotide kinase (Affymetrix, Santa Clara, Calif.) and 3.2 pmol of [γ-$^{32}$P]ATP (6000 Ci/mmol; Perkin Elmer, Waltham, Mass.). The quantity of [γ-$^{32}$P]ATP was doubled for the ProbeSOFA labeling reaction. The labeled oligonucleotides were purified with ProbeQuant™ G50 Micro Colums (GE Healthcare, Little Chalfont, UK) and used directly for the Northern blot, their sequences were:

```
ProbeSOFA:
                                      (SEQ ID NO: 32)
5'-GAAAGGGTCCCTTAGCCATCCGCGAACGGATGCCC-3'

Probe5S:
                                      (SEQ ID NO: 33)
5'-AAAGCCTACAGCACCCGGTATTCCC-3'.
```

Northern blot conditions: Total RNA samples were dissolved in RNAse-free water and quantified (Nanvovue, Roche, Basel, Switzerland). For each condition, 10 µg of total RNA mixed with 2 volumes of loading buffer was resolved on 8% denaturing PAGE. The RNA was then transferred (90 min, 4° C., 200 mA) to a nylon membrane (Amersham Hybond-N+, GE Healthcare, Little Chalfont, UK) in 0.5×TBE using a Trans-blot cell (Bio-Rad, Hercules, Calif.). Membranes were UV crosslinked prior to pre-hybridization at 42° C. in CHURC buffer (1% (W/V) BSA, 1 mM EDTA, 500 mM phosphate buffer and 7% (W/V) SDS). After 2 to 4 h, the radio-labeled ProbeSOFA was added, and the membranes were hybridized at 42° C. overnight. Before analysis, the membranes were washed twice, 5 min each, in wash buffer #1 (2×SSC, 0.1% SDS) and twice, 15 min each, in wash buffer #2 (0.1×SSC, 0.1% SDS), all at 42° C. The results were visualized using a Phosphor Screen. For the Probe5S hybridization, the membranes were stripped by incubation in wash #2 at 80° C. for 20 min to remove the ProbeSOFA. Only 5 to 10% of the labeled Probe5S was used for the hybridization of one membrane.

In Vitro SOFA-HDV-Rz Cleavage Assay

Single-turnover conditions (Rz>>substrate) were used to evaluate the catalytic activity of SOFA-HDV-Rzs as previously described[28]. Briefly, a trace amount of 5'-end-labeled substrate (<1 nM) was incubated at 37° C. with a final concentration of 100 nM of the selected SOFA-HDV-Rz. The cleavage reactions were initiated by the addition of $MgCl_2$ and samples were taken at different time intervals and stopped with loading buffer. Recovered samples were resolved on a 20% denaturing polyacrylamide gel, visualized using a Phosphor Screen and quantified using ImageQuant® software (Molecular Dynamics, Sunnyvale, Calif.). The control reaction was performed in the absence of Rzs (replaced by water) and its last time interval sample was used to subtract the background. For each time point, the percentage of cleavage was calculated (cleaved product counts over cleaved+uncleaved products counts). Details on the DNA templates used for in vitro transcription, RNA synthesis and labelling are provided below. The $k_{obs}$ and $F_{max}$ were then calculated using GraphPad Prism™ 5 for each Rz. The rate of cleavage ($k_{obs}$) was obtained by fitting the data to the equation $F_t = F_{max}(1-e^{-kt})$, where $F_t$ is the percentage of cleavage at time t, $F_{max}$ is the maximum percent cleavage and k is the rate constant ($k_{obs}$).

DNA Templates for In Vitro Transcription:

SOFA-HDV-Rz DNA templates were generated through a PCR-based strategy with DNA oligonucleotides C and D shown in Plasmid constructs. The SOFA-HDV-Rz sense primer (D) provided the T7 RNA polymerase promoter needed for subsequent in vitro transcription. The fully double-stranded DNA sequences were produced using Pwo DNA polymerase (Roche Diagnostics). Similarly, the substrate DNA template was produced by a combination of two complementary oligonucleotides, subA and sub.

The reaction mixtures were then treated with RQ1 DNase (Promega, Madison, Wis.) at 37° C. for 20 min. After phenol/chloroform extraction the RNAs were ethanol precipitated. The pellets were dissolved in equal volumes of ultrapure water and loading buffer (95% formamide, 10 mM EDTA [pH 8.0], 0.025% xylene cyanol and 0.025% bromophenol blue). The samples were then fractionated through either 8% or 20% denaturing polyacrylamide gels (PAGE, 19:1 ratio of acrylamide to bisacrylamide) in buffer containing 45 mM Tris-borate (pH 7.5), 8 M urea, and 2 mM EDTA. The RNA products were visualized by ultraviolet (UV) shadowing. The bands corresponding to the correct sizes for both the SOFA-HDV-Rzs and the substrate were cut out of the gel and the RNAs eluted overnight at 4° C. in elution buffer (500 mM ammonium acetate, 10 mM EDTA, 0.1% SDS). The samples were again ethanol precipitated, washed, dried and dissolved in ultrapure water. The RNA was quantified by absorbance at 260 nm and diluted to the desired concentration (Rz 1 µM and Substrate 5 µM).

RNA and Probes Labelling

The RNA substrate used in cleavage reactions was 5'-end labeled as described previously (28). Briefly, the purified RNA substrate was dephosphorylated by mixing 50 pmol of RNA with 1 U of Antarctic phosphatase (New England Biolabs) in a final volume of 10 µL containing the buffer provided with the enzyme, and then incubated for 30 min at 37° C. Incubation at 65° C. for 8 min was used to inactivate the enzyme. The 5'-end labeling reaction was performed with 5 pmol of dephosphorylated RNAs that were incubated for 1 h at 37° C. with 3 U of T4 polynucleotide kinase (USB) and 3.2 pmol of [γ-$^{32}$P]ATP (6000 Ci/mmol; New England Nuclear) in the reaction buffer provided with the enzyme. The reactions were stopped by the addition of two volumes of loading buffer prior to fractionation by 20% denaturing PAGE. The RNAs were detected by autoradiography, cut out of the gel and eluted as described in RNA synthesis for in vitro transcription.

TABLE 4

Sequence of oligonucleotides subA and subB

| Name | Sequence (5'-3') | SEQ ID NO |
|---|---|---|
| subA | taatacgactcactataGGGCATAGCAGGAACTACTAGTACCCTTGGG TCGGCAGGGTCCACCTCC | 34 |
| subB | GGGTCCCTTAGCCATGCGAAGCCGCATGCCCAGGTCGGACCG CGAGGAGGTGGACCCTGCCGACCC | 35 | subA contained the T7 RNA polymerase promoter (lower case) at its 5'-end and part of a cis-acting HDV ribozyme (underlined sequence) at its 3'end. The subB primer is complementary (underlined sequence) to the forward primer and completes the cis-acting HDV ribozyme. The cis-acting HDV ribozyme permits the production of a precise 3'-end as described in Avis, J. M., et al. (2012) *Methods Mol Biol*, 941, 83-98. The final RNA substrate, SubMin1498, corresponds to the sequence in bold. All PCR reactions were ethanol precipitated prior to in vitro transcription.

RNA Synthesis for In Vitro Transcription:

The SOFA-HDV-Rz and the substrate RNA were synthesized by run-off transcriptions as described previously (28). Briefly, transcriptions were performed in the presence of purified T7 RNA polymerase (10 µg), pyrophosphatase (0.01 U, Roche, Basel, Switzerland) and PCR product (2 to 5 µM) in a buffer containing 80 mM HEPES-KOH (pH 7.5), 24 mM $MgCl_2$, 2 mM spermidine, 40 mM DTT and 5 mM of each NTP in a final volume of 100 µL at 37° C. for 2 h.

HIV-1 Protein Expression in HEK293T Cells

Figure 11A:
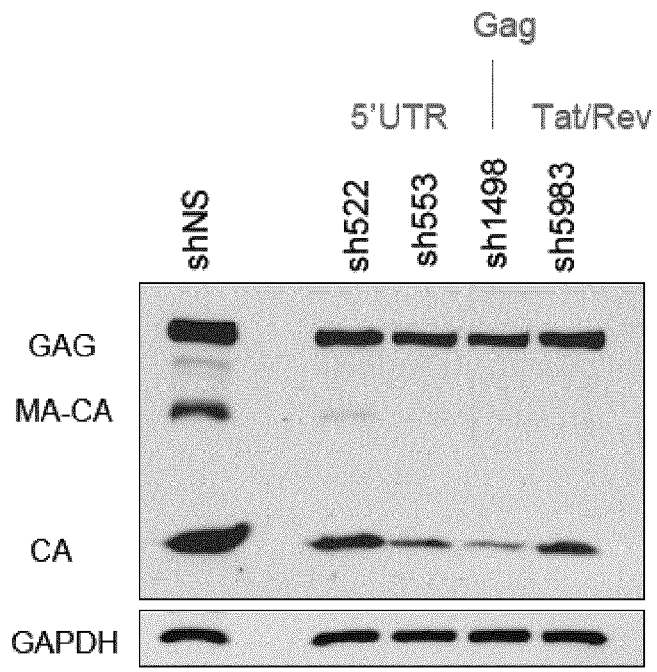
FIGS. 11A and B show Gag and Capsid protein expression in cells co-transfected with HIV-1 pNL4-3 and different HIV-1 RNA specific shRNAs. HEK293T cells were seeded in 12 well plates and co-transfected with HIV-1 pNL4-3 plasmid DNA (150 ng) and one of the indicated psiRNA short hairpin (sh) RNA expression plasmids (300 ng). A nonsense (NS) shRNA was used as a control (shRNAns) and shRNAs targeting the 5'UTR (shRNA522 and shRNA553), the Gag coding sequence (shRNA1498) and the overlapping tat/rev coding sequence (shRNA5983) of HIV-1 were evaluated. Cell lysates were obtained 48 h after co-transfection.
Figure 11B:
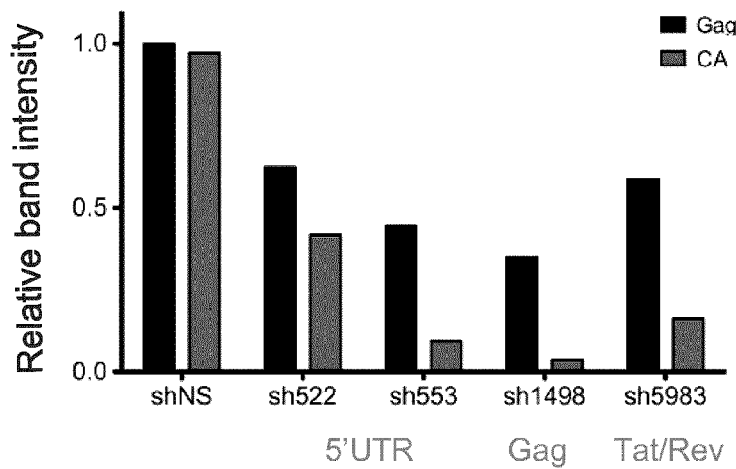
FIG. 11B: Relative band intensities for Gag and CA were calculated using Image J™ software and are expressed as a fraction of the intensity of Gag in the shNS control lane.

The detection of HIV-1 protein expression using an HIV-1 p24 antibody in HEK293T cells has been previously described[50]. Briefly, 100 µg of total protein was resolved on a 10% denaturing poly-acrylamide gel and transferred to a Hybond® ECL nitrocellulose membrane (GE Healthcare, Little Chalfont, United Kingdom). Membranes were incubated first with anti-HIVp24 (183-H12-5C) followed by anti-GAPDH (sc-32233, Santa Cruz Biotechnology, Dallas, Tex.), bands were visualized using ECL (GE Healthcare, Little Chalfont, United Kingdom). The relative intensity of bands was calculated using Image J densitometry software (Version 1.48, National Institutes of Health, USA). Data are expressed as Gag or CA band intensities relative to the intensity of the Gag band in the control SOFA-HDV-RzHBV (FIG. 5B) or shRNAns (FIGS. 11A and B) lanes.

Gene Expression Profiling

Gene expression levels relative to control transfections were analyzed by human gene expression microarrays (Atlantic Cancer Research Institute (ACRI) proprietary slides).

RNA Extraction and mRNA Analysis:

Total RNA extracts were harvested from transfected cells using Trizol® reagent (Invitrogen®) according to the manufacturer's instructions and purified using an RNeasy® column (Qiagen®). Quality of total RNA samples was assessed using the Experion® bioanalyzer system with RNA Stdsens chips and associated reagents (BIO-RAD®). All RNA used in these experiments had an RNA Quality Index (RQI) value greater than nine. 1 μg of each total RNA sample was amplified using the Amino Allyl MessageAmp® II aRNA amplification kit and subsequently labeled with AlexaFluor® 555 or 647 (Life Technologies®). Quantity and quality of amplified aRNA was assessed using a Nanodrop spectrophotometer and the Experion® bioanalyzer. Samples were compared in triplicate dye swap experiments, with 1.5 μg of each labeled, fragmented aRNA (3 μg total per slide) hybridized to proprietary human cDNA microarray slides. These arrays consist of roughly 35000 spots, representing roughly 17000 different 50-mer oligonucleotides spotted in duplicate on Nexterion-E® epoxy microarray slides (Schott, Mainz, Germany).

Hybridizations were performed in Ambion® SlideHyb #2 buffer (Life Technologies®) at 42° C. for 16 h using the automated TECAN® 4800 Hybridization station (TECAN®). Following hybridization, slides were scanned at 10 μm resolution using an Axon GenePix® 4200AL scanner (Molecular Devices, Sunnyvale, Calif.) and gridded using SpotReader® (Niles Scientific). Fine tuning of spot rejection was subsequently done by visual inspection of the gridded image and of a scatter plot of M=log(532/635) versus A=log(532)+log(635), special attention being paid to outliers. A GPR file was generated that was subsequently processed to flag spots with a signal to noise ratio of less than 5.

Data analysis was done with Acuity™ 4.0 (Axon Instruments, Sunnyvale, Calif.) and subsequently normalized using Lowess. The resulting log 2 ratios of SOFA-HDV-Rz or shRNA1498 transfected cells compared to the empty vector (psiRNA) transfected cells were then further analyzed using various statistical and visual methods such as SOM (Self Organizing Maps), t-Test, PCA (Principal Component Analysis) and volcano plot.

HIV-1 Infection Assay

Stable Jurkat T lymphocytes were generated by electroporation of psiRNA constructs followed by selection with Zeocin (InvivoGen). The relative expression of psiRNA constructs in the stable cell populations was estimated by measuring GFP expression from the integrated vector with a FACSCalibur® flow cytometer (BD), and proliferation was determined by counting live cells by Trypan blue (Wisent) exclusion using a hemocytometer. Prior to infection, SOFA-HDV-Rz or shRNA expressing cells were plated in 6 well plates at 2×10⁵ cells per well. Viral replication was monitored by measuring RT activity in culture supernatants at various days post infection.

Generation and Characterization of Stable Jurkat T Cells

1×10⁶ Jurkat T cells were electroporated at 250 mV for 10 msec (GenePulserII®, Biorad) with 15 μg of psiRNA plasmids and cultured in 5 mL RPMI overnight. Cells were transferred to 20 mL culture media containing 600 μg/mL Zeocin (InvivoGen®) and cultured for 4 weeks with selection media changed every 3-4 days. Cells were split at various times during the selection to maintain a high cell density in the first 2 weeks of selection, and a low cell density in the last 2 weeks of selection. At the end of the selection period cells were frozen, or cultured for an additional day in the absence of Zeocin prior to infection with HIV-1 virions. The expression of GFP in the different cell populations was determined using a FACSCalibur® flow cytometer (BD) and data analysis was performed using FlowJo® Version 8.7 (Tree Star). Cell proliferation was determined by plating cells at 1×10⁵ cells/mL in a 6 well plate followed by counting live cells diluted in Trypan blue (Wisent) with a hemocytometer. Duplicate wells were counted for each cell line out to four days.

Virus Infection:

A 20 mL culture of HEK293T cells was transfected with 20 μg of HIV-1 pNL4-3 plasmid DNA. The supernatant was harvested 48 h later, cleared of cell debris by centrifugation, and stored at −80° C. in 1 mL aliquots. SOFA-HDV-Rz and shRNA expressing Jurkat T cells were plated in 6 well plates at $2 \times 10^5$ cells/well and infected with the HEK293T cell supernatant corresponding to $6 \times 10^5$ cpm equivalent of HIV-1 RT activity per well. Viral replication was monitored by measuring RT activity in the culture supernatants at various days post infection. All infections were performed in triplicate wells, cells were split twice a week.

HIV-1 RT Assay

The HIV-1 RT assay used in this study was performed as previously described[45]. Briefly, 5 μl of supernatant was incubated with a polyadenylic acid template (Roche, Basel, Switzerland), an oligodT primer (Life Tech., Carlsbad, Calif.) and [$^{32}$P]-dTTP (3,000 Ci/mmol, Perkin Elmer, Waltham, Mass.) for 2 h at 37° C. in 50 μl total reaction mixture. 5 μl of the reaction mixture was then spotted onto Diethylaminoethyl (DEAE) filter mat (Perkin Elmer, Waltham, Mass.) and washed five times in 2×SSC buffer, followed by two washes in 95% ethanol to remove [$^{32}$P]-dTTP not incorporated into the polydT RT product. Counts per minute (cpm) were calculated for each sample using a microplate scintillation counter (Microbeta TriLux, Perkin Elmer,) and are proportional to the amount of HIV-1 RT enzyme present in the reaction mixture.

EXAMPLE 2

Identification of SOFA-HDV-Rz Target Sites in HIV-1 RNA

Figure 2B:
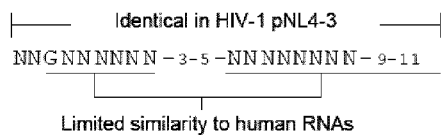
Figure 9:
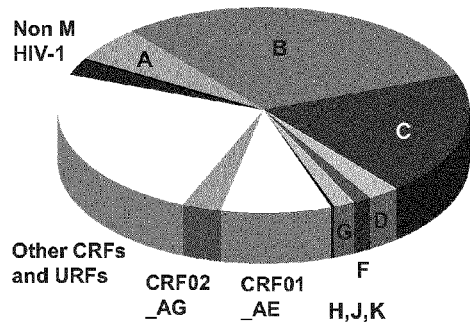
FIG. 9 shows the subtype distribution of HIV-1 sequences used to calculate conservation estimates in comparison to global distribution estimates. HIV-1 Group M subtypes A-D, F-H, J, K, circulating recombinant forms (CRFs) 01_AE and 02_AG, other CRFs and unique recombinant forms (URFs) and non M-group HIV-1 sequences are illustrated over or next to their proportional representation in the Los Alamos National Laboratory (LANL) dataset used to evaluate sequence conservation (left) and global estimates reproduced from reference #44 (right).
Figure 9:
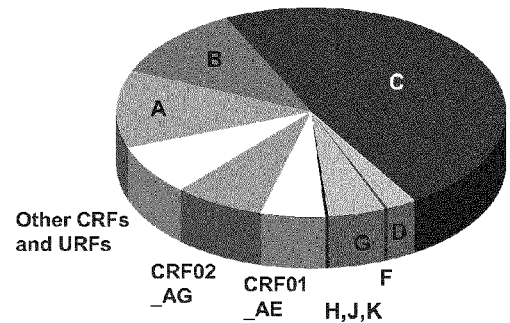

HIV-1 sequence conservation was estimated to identify target sites that are relevant for the majority of HIV-1 strains. Estimates at the nt level were made (Reference #51) using all complete sequences available in the Los Alamos National Laboratory (LANL) database (1850 at the time of analysis, subtype distribution shown in FIG. 9). These estimates were used to identify highly conserved SOFA-HDV-Rz target sites (FIG. 2A) that were identical in HIV-1 strain NL4-3 (FIG. 2B). The Ribosubstrates informatics tool[26] was used to exclude SOFA-HDV-Rzs targeting 12 highly conserved and 19 moderately conserved regions in HIV-1 RNA, due to their potential to target human RNAs.

Figure 2C:
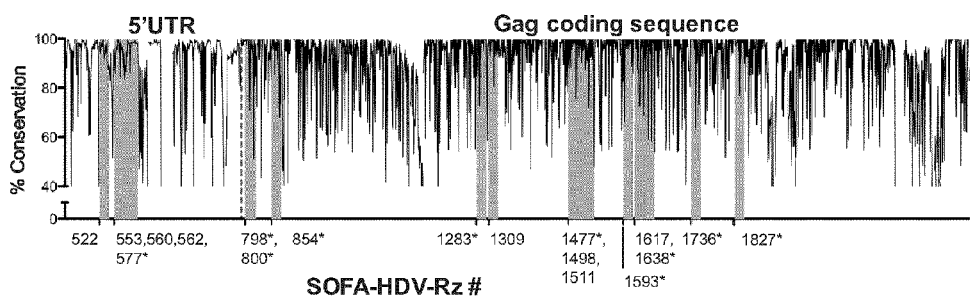

Several highly conserved target sites were identified in the 5'LTR U5 region within the 5'UTR (FIG. 2C). The Gag coding sequence had much lower overall conservation; however, four highly conserved and, with some exceptions to the conservation criteria (FIG. 2A), nine moderately conserved target sites were identified in this region (FIG. 2C). Of the Rzs that we have previously evaluated targeting the Tat/Rev exon1 coding sequence of HIV-1 RNA[16], the target sites for Tat1 and Tev1 were highly and moderately conserved, respectively. Conservation exceptions and sequences of all target sites used in this study are illustrated, along with the DNA sequences of the corresponding SOFA-HDV-Rz variable regions, in Table 5.

TABLE 5

SOFA-HDV-Rz target sites and DNA coding sequences

| Rz | HIV-1 NL4-3 target sites: 5'-3'[1] RD Bs | SEQ ID NO: | SOFA-HDV-Rz DNA sequences 5'-3'[2] Bs | RD | BI | SEQ ID NO (Bs) |
|---|---|---|---|---|---|---|
| HBV | — | | GAGACAAGAA | AAACCAT | GTTT | 56 |
| Tat1 | TA<u>GATCCTA</u>ga<u>CTAGAGCCCTGGAA</u> | 36 | CCAGGGCTCT | TAGGATT | CCTA | 57 |
| Tev1 | CA<u>GGAAGAAGCGGAGACA</u>a<u>CGA</u>CGA | 37 | GTCGCTGTCT | TTCTTCT | AGAA | 58 |
| 522 | AA<u>GCCTCAATAAAGCTTGCCTTGAG</u> | 38 | CAAGGCAAGC | TTGAGGT | TCAA | 59 |
| 553 | AA<u>GTAGTGTGTGCCCGTCTGTTGTG</u> | 39 | ACAACAGACGG | ACACTAT | GTGT | 60 |
| 560 | GT<u>GTGCCCGTCTGTTGTGTGACTCT</u> | 40 | AGTCACACAA | CGGGCAT | CCCG | 61 |
| 562 | GT<u>GCCCGTCTGTTGTGTGACTCTGG</u> | 41 | AGAGTCACAC | GACGGGT | CGTC | 62 |
| 577 | GT<u>GACTCTGGTAACTAGAGATCCCT</u> | 42 | GGATCTCTAG | CAGAGTT | TCTG | 63 |
| 798 | GC<u>GAGAGCGTC</u>gg<u>TATTAAGc</u>GGGG | 43 | CCGCTTAATA | CGCTCTT | AGCG | 64 |
| 800 | GA<u>GAGCGTC</u>gg<u>TATTAAGc</u>GGGGGA | 44 | CCGCTTAAT | GACGCTT | CGTC | — |
| 854 | AA<u>GGCCAGGGGGAAAGAAAcAa</u>TAT | 45 | ATTGTTTCTT | CCTGGCT | CAGG | 65 |
| 1283 | c<u>AGCCCAGA</u>a<u>GTAATACCCATGTTT</u> | 46 | ACATGGGTAT | TCTGGGT | CAGA | 66 |
| 1309 | CAGCATTATCAGAa<u>GGAGCCACCCC</u> | 47 | GGTGGCTCC | ATAATGT | TTAT | — |
| 1477 | Ga<u>GAACCAAGGGGAAGTGA</u>c<u>ATAGC</u> | 48 | ATGTCACTTC | TTGGTTT | CCAA | 67 |
| 1498 | TA<u>GCAGGAACTACTAGTACCCTTCA</u> | 49 | AAGGGTACTA | TTCCTGT | GGAA | 68 |
| 1511 | TA<u>GTACCCTTCA</u>g<u>GAACAAATAG</u>gA | 50 | CTATTTGTTC | AGGGTAT | CCCT | 69 |
| 1593 | CT<u>GGG</u>a<u>TTAAATAAAATAGTAAGAA</u> | 51 | CTTACTATTT | TAATCCT | ATTA | 70 |
| 1617 | AT<u>GTATAGCCCT</u>ac<u>CAGCATT</u>c<u>TGG</u> | 52 | CCAGAATGCTG | GCTATAT | TAGC | 71 |
| 1638 | c<u>TGGACATAA</u>g<u>ACAAGGa</u>CC<u>AAAgG</u> | 53 | CTTTGGTCCTT | TATGTCT | CATA | 72 |
| 1736 | TT<u>GGATGACAGA</u>a<u>ACCTTG</u>t<u>TGGTC</u> | 54 | CCAACAAGGT | GTCATCT | TGAC | 73 |
| 1827 | AT<u>GATGACAGCATG</u>t<u>CAGGGAGTGG</u> | 55 | ACTCCCTGAC | TGTCATT | GACA | 74 |

[1] The target sites of the SOFA-HDV-Rzs identified are shown with the recognition domain (RD) and the biosensor (Bs) binding sites underlined. Nucleotides with identities different in HIV-1 pNL4-3 in comparison to the consensus sequence are in lower case, those conserved in less than 80% of the sequences are shown as bold lower case.
[2] The variable DNA sequences used to clone SOFA-HDV-Rzs into the psiRNA vector are shown for the RD, Bs and Blocker (BI) regions.

EXAMPLE 3

SOFA-HDV Rz Screen for Inhibition of HIV-1 Production

Figure 3:
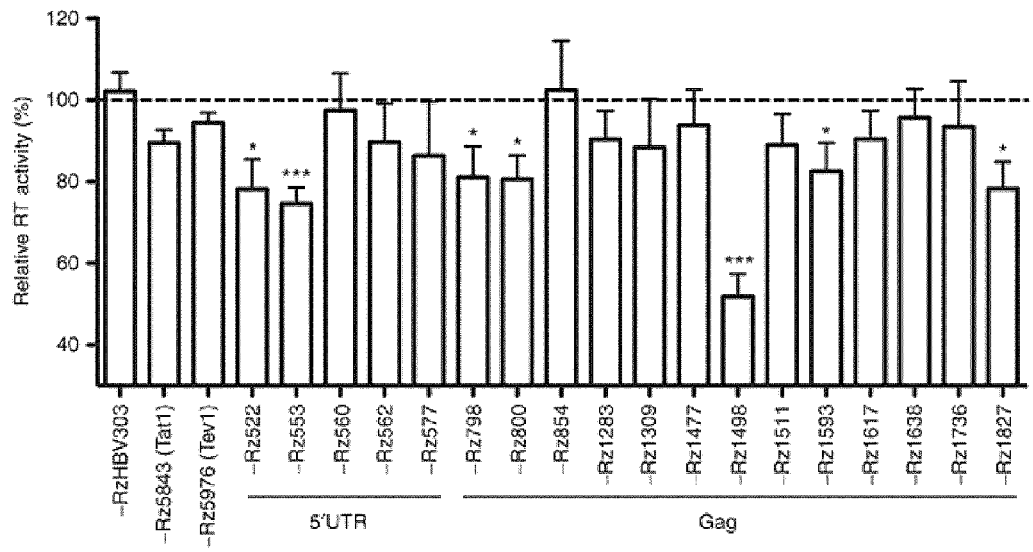
FIG. 3 shows the inhibition of HIV-1 production by SOFA-HDV-Rzs. HEK293T cells were seeded in 24 well plates and co-transfected with HIV-1 pNL4-3 plasmid DNA (75 ng) and one of the indicated psiRNA SOFA-HDV-Rz expression plasmids (750 ng). Viral production was estimated 48 h following transfection by measuring the activity of HIV-1 RT in culture supernatants. Each replicate was expressed as a percentage of the value obtained for co-transfection with the empty Rz expression plasmid tested in parallel (Relative RT activity). Rzs were evaluated in at least three independent experiments with one to three replicate transfections, data are expressed as the mean+/−standard error mean (SEM) (n=5-10). Graph Pad Prism™ was used to calculate P values for the effects of each HIV-1 specific SOFA-HDV-Rz compared to the irrelevant control (-RzHBV). Results from un-paired t-tests are shown above each SOFA-HDV-Rz that demonstrated a significant inhibition of viral production compared to the control (* P<0.05,  P<0.01, * P<0.001).

The effect of each SOFA-HDV-Rz expressing plasmid on HIV-1 production was evaluated by co-transfection with HIV-1 molecular clone pNL4-3 in HEK293T cells, using conditions similar to those reported for other Rzs[7,18,27] and shRNAs[21,22]. HIV-1 RT activity was measured to estimate the production of virus released into the medium of transfected cells and effects of Rzs were normalized to co-transfection of pNL4-3 with an empty Rz expression plasmid. An irrelevant Rz targeting Hepatitis B Virus RNA (SOFA-HDV-RzHBV, adapted from SOFA-δRz-303[9]) was used as a negative control and previously described SOFA-HDV-Rzs Tat1 and Tev1[16] were used as positive controls. Compared to SOFA-HDV-RzHBV, Rzs targeting both the 5'UTR and Gag coding sequences significantly inhibited viral production, with the top candidate (SOFA-HDV-Rz-1498) targeting the Gag coding sequence (FIG. 3).

EXAMPLE 4

Figure 4A:
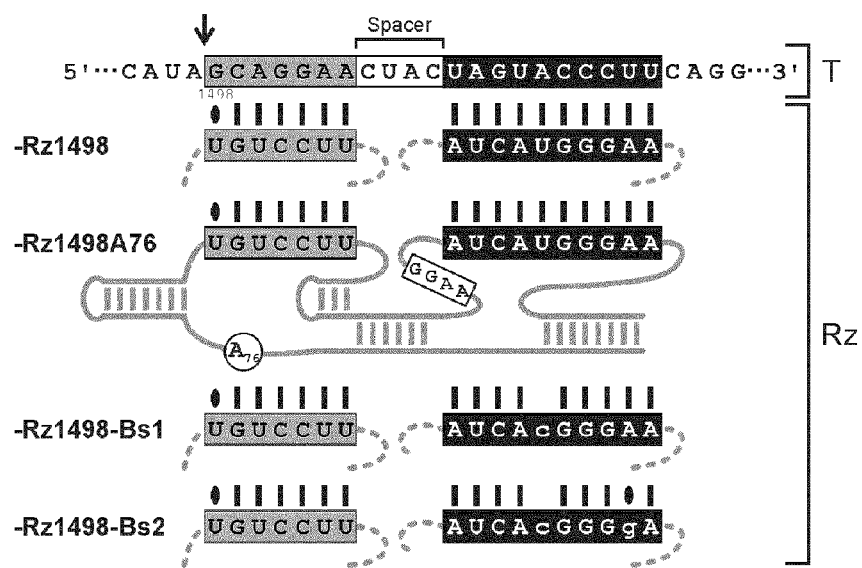
FIGS. 4A to C show the effects of SOFA-HDV-Rz1498 variants on HIV-1 production.
Figure 4B:
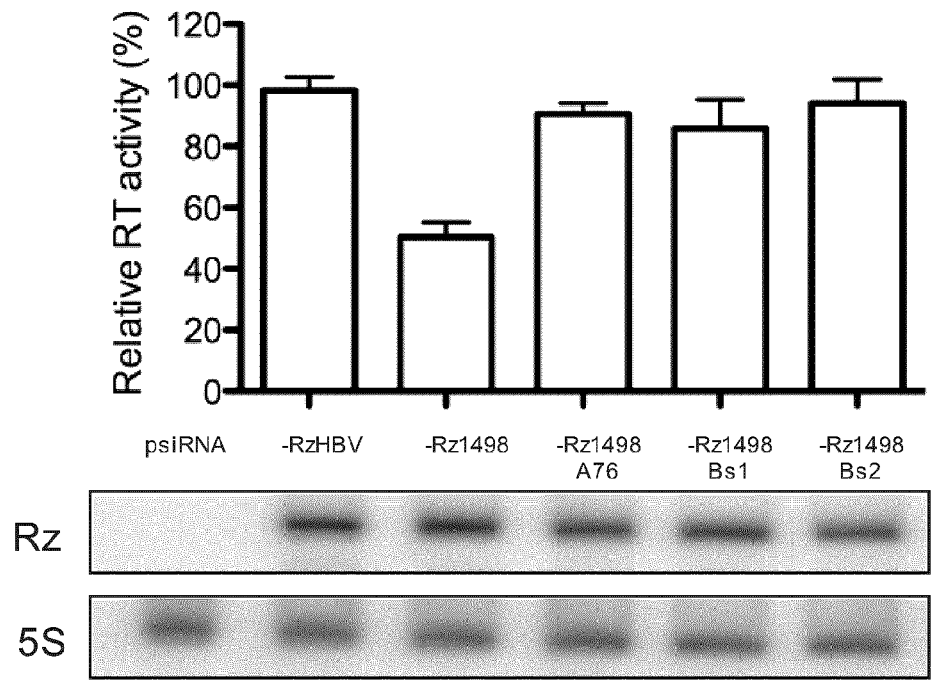
Figure 10A:
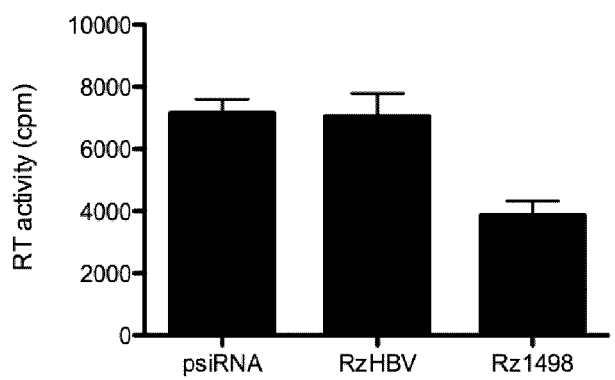
FIGS. 10A and B show the effect of SOFA-HDV-Rz1498 on the quality of virions produced from co-transfected HEK293T cells.
Figure 10B:
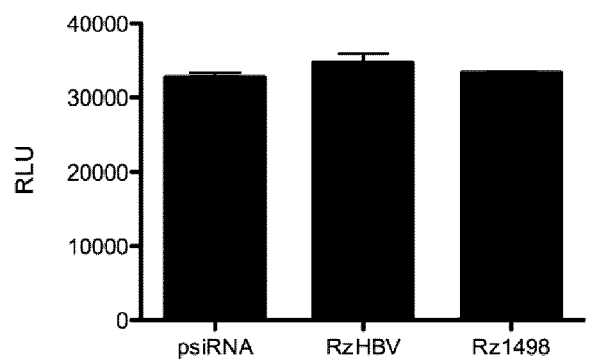
FIG. 10B: Supernatants from FIG. 10A were normalized by volume to the same RT activity and used to infect TZM-bl cells seeded in 12 well plates 24 h prior to infection. 48 h after infection, intracellular luciferase activity was measured (expressed as relative luciferase units, RLU). Luciferase activity is proportional to the level of Tat protein produced from viral genomes that integrated into the TZM-bl genome following infection and is a measure of viral infectivity.

Antisense and Mismatched Variants of SOFA-HDV-Rz1498 are not Effective Inhibitors of HIV-1 Production To evaluate the antisense effect of SOFA-HDV-Rz1498, we generated an inactive variant (SOFA-HDV-Rz1498A76) in which a C to A mutation at position 76 in its backbone disables its cleaving capability[28] (FIG. 4A). SOFA-HDV-Rz1498A76 did not significantly inhibit HIV-1 production at similar expression levels to SOFA-HDV-Rz1498 (FIG. 4B), suggesting that Rz catalytic cleavage is primarily responsible for the effects of SOFA-HDV-Rz1498. No effect on the infectivity of virus from SOFA-HDV-Rz1498 expressing cells was observed (FIG. 10), suggesting that the Rz reduces the amount of virus produced but does not affect the quality of the virions.

Figure 4C:
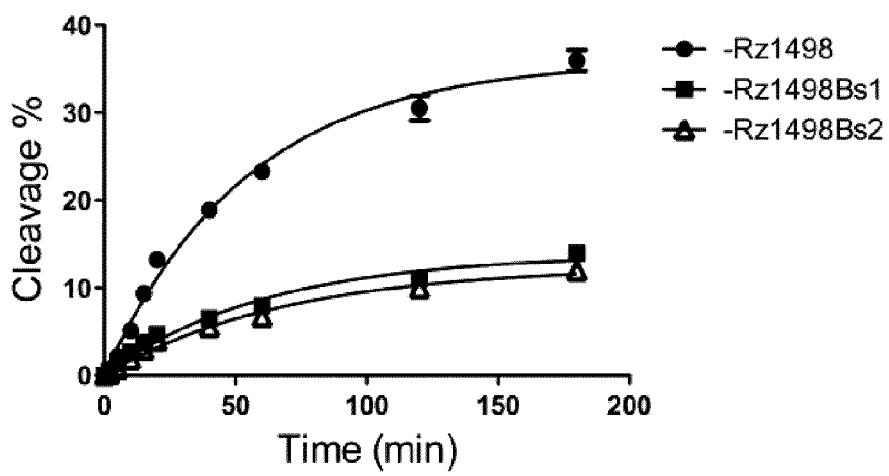

SOFA-HDV-Rz1498 variants with either a single or double mutation in their biosensor (Bs) sequence were also generated to evaluate the potential for SOFA-HDV-Rz1498 to tolerate mismatches with its target (SOFA-HDV-Rz1498Bs1 and SOFA-HDV-Rz1498Bs2, FIG. 4A). Neither variant inhibited HIV-1 production (FIG. 4B), suggesting that the effect of SOFA-HDV-Rz1498 is sensitive to mismatches with its target. The mismatched Rzs had similar in vitro cleavage rate constants ($k_{obs}$) with significantly reduced maximum cleavage ($F_{max}$) values (FIG. 4C), suggesting that part of their failure to inhibit HIV-1 production in cells is related to a reduced capacity to cleave their target.

EXAMPLE 5

An shRNA Targeting the 1498 Site is a Potent Inhibitor of HIV-1 Production and Provides an Additive Effect in Combination with SOFA-HDV-Rz1498

Figure 5A:
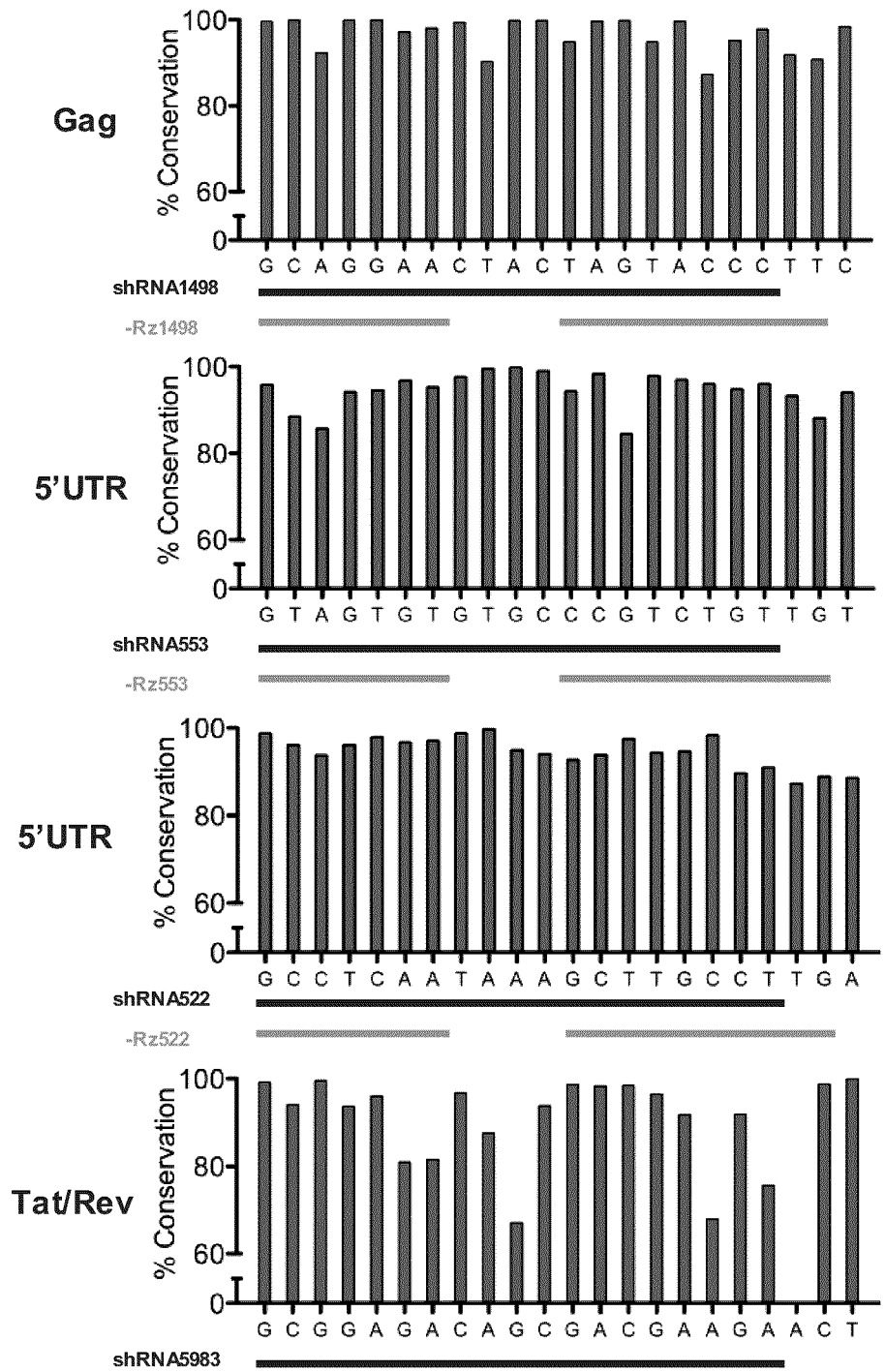
Figure 5B:
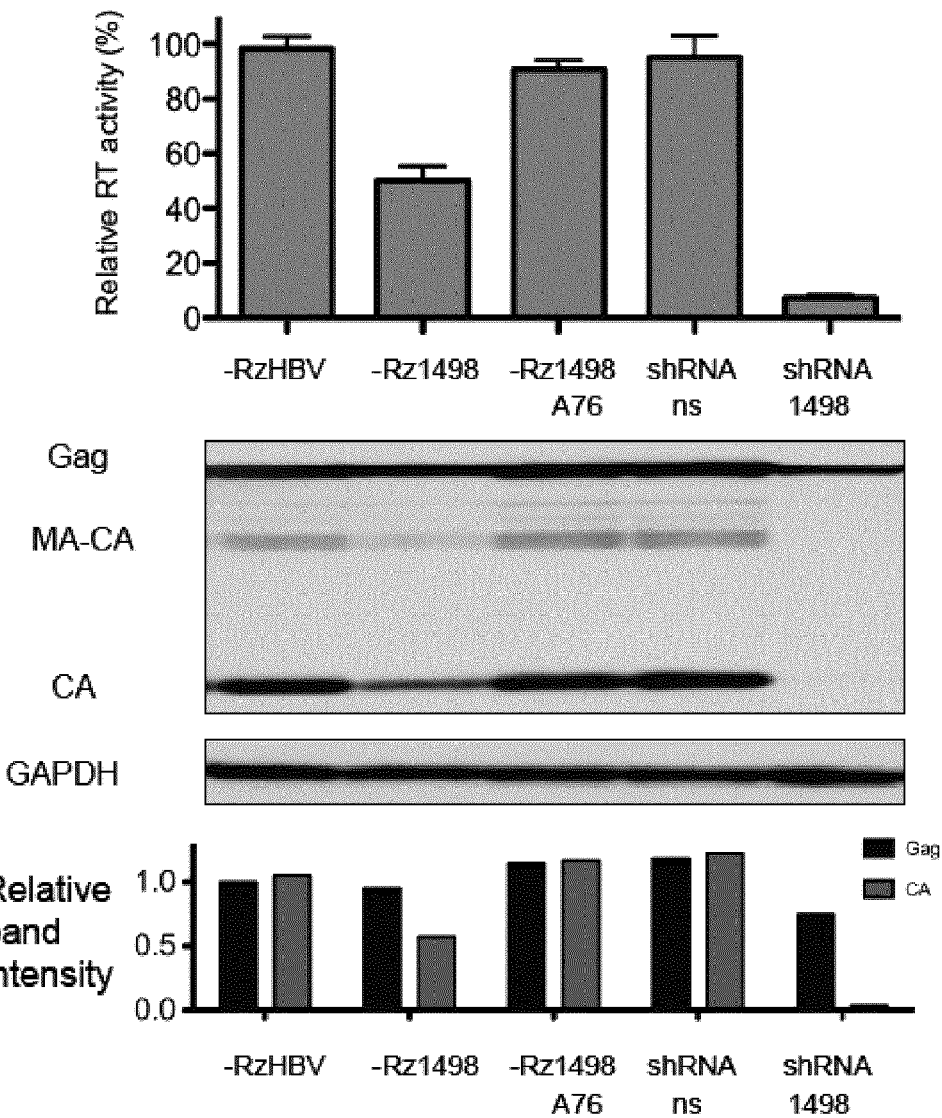

To evaluate the potential for other antisense molecules targeting the SOFA-HDV-Rz1498 target site to inhibit HIV-1 production, shRNA1498 was designed. According to the conservation estimates, each nt in the shRNA1498 target site was conserved at >80% (FIG. 5A, Gag). Compared to a nonsense shRNA (shRNAns) as well as SOFA-HDV-Rz1498 and its controls, shRNA1498 provided a near complete inhibition of viral production (FIG. 5B). This inhibition correlated with a decrease in intracellular expression of the HIV-1 Gag polyprotein and one of its processing products, capsid (CA). Unexpectedly, the decrease in CA expression was much more pronounced for both the Rz and shRNA compared to their effects on Gag expression. A similar effect was observed for shRNAs targeting sequences in the 5'UTR and Tat/Rev coding sequences of HIV-1 RNA (FIGS. 11A and B), suggesting that it is not specific to an shRNA targeting the Gag 1498 sequence.

Figure 5C:
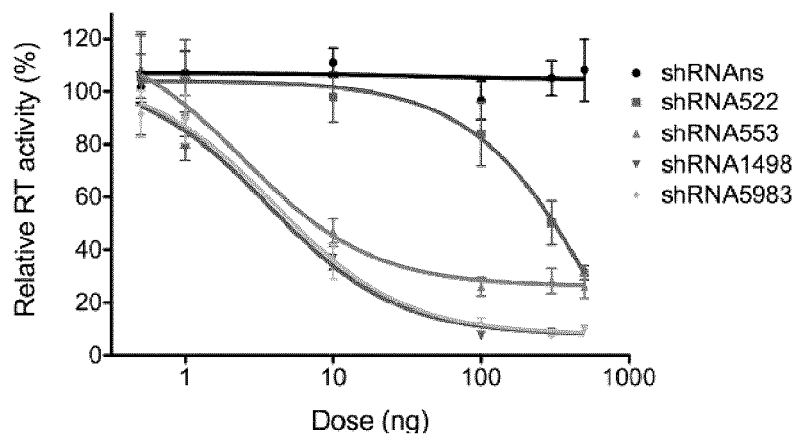

To compare the potency of shRNA1498 to other candidate shRNAs, shRNA522 and shRNA553 were designed, modeled after previously characterized siRNAs[20] and shRNAs[22] targeting the 5'UTR (FIG. 5A, 5'UTR) and shRNA5983, modeled after a construct in clinical development targeting the Tat/Rev exon1 coding sequence[29] (FIG. 5A, Tat/Rev). All four shRNAs inhibited HIV-1 production (FIG. 5C). The potency of shRNA1498 was comparable to that of shRNA553 and shRNA5983, with 50% effective concentrations (EC50s) for shRNA plasmids below 5 ng of input DNA, whereas shRNA522 was much less potent with an EC50 value of 702 ng.

To evaluate the potential for shRNA1498 and shRNA5983 to be used in combination with SOFA-HDV-Rz1498, HEK293T cells were co-transfected with HIV-1 pNL4-3 and different combinations of Rzs and shRNAs (FIG. 5D). To quantify the effect of the combinations, an input level of shRNA DNA that did not completely inhibit viral production in FIG. 5C was chosen. In combination with both shRNA1498 and shRNA5983, SOFA-HDV-Rz1498 provided an additional inhibition of HIV-1 production compared to the control Rz, SOFA-HDV-Rz-HBV. The level of inhibition was similar to its effect when co-transfected alone (50%) (FIG. 5B), suggesting that the Rz can provide an additive effect in combination with both an shRNA targeting the same site (shRNA1498) and an shRNA targeting a different site (shRNA5983).

EXAMPLE 6

SOFA-HDV-Rz1498 and shRNA1498 Inhibit Viral Production from Diverse HIV-1 Strains As the Gag 1498 target site was shown to be accessible to both Rz and shRNA activity in HIV-1 strain pNL4-3, it was next evaluated whether this inhibition extended to diverse viral strains representing subtype B (Mal[30] and AD8[31]), C (Indie-C1[32] and MJ4[33]), D (94UG114[34]) and circulating recombinant form (CRF) 02_AG (97GH-AG1[35]). SOFA-HDV-Rz1498 inhibited HIV-1 production from viral strains (Mal, ADB, MJ4 and 97GH-AG1) with nt variants in proximity to their target sites compared to NL4-3 (FIG. 6), suggesting that the structure of the target site is equally accessible to the Rz in these strains. Consistent with results using SOFA-HDV-Rz binding site variants (FIG. 4, -Bs1 and -Bs2), SOFA-HDV-Rz1498 did not inhibit HIV-1 production from the strains Indie-C1 and 94UG114, which harbor a single nt variant within their Bs binding sites (FIG. 6). In contrast, shRNA1498 inhibited HIV-1 production from all strains suggesting that it can tolerate a single nt mismatch in its binding site at position 17 and can inhibit HIV-1 production in diverse strains.

EXAMPLE 7

SOFA-HDV-Rz1498 and shRNA1498 have Minimal Off Target Effects on Human RNAs

Figure 7:
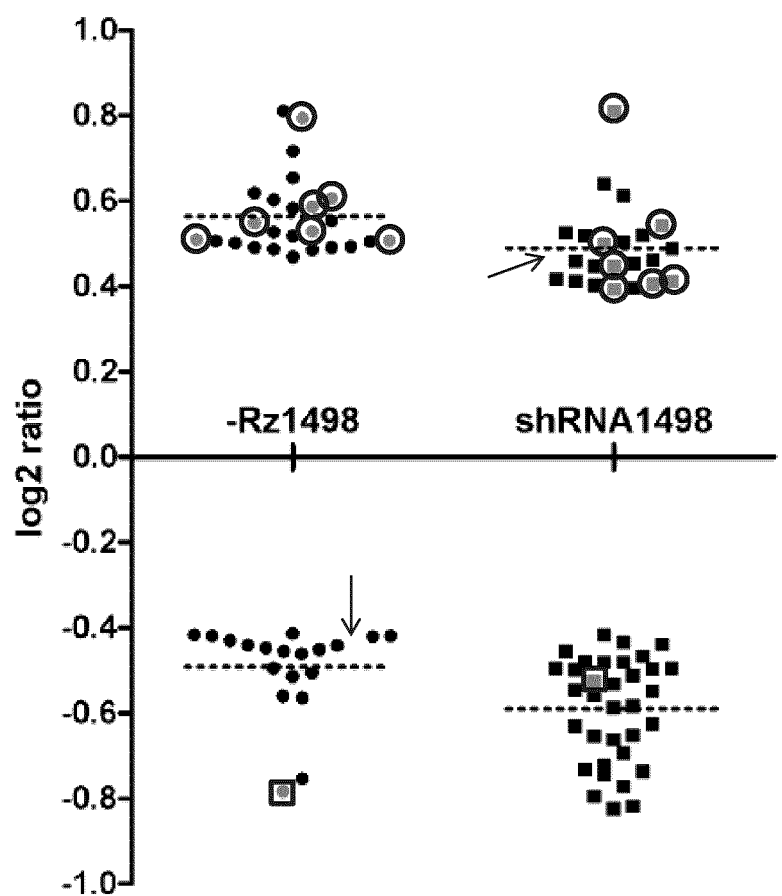
FIG. 7 shows gene expression changes in cells transfected with SOFA-HDV-Rz1498 and shRNA1498. HEK293T cells were seeded in 12-well plates and co-transfected with HIV-1 pNL4-3 (150 ng) and either SOFA-HDV-Rz1498, shRNA1498 or the empty Rz/shRNA expression plasmid (1.5 µg). 48 h after transfection, total RNA was harvested and analyzed by microarray. The log 2 ratios of mRNAs with the greatest differential variation between SOFA-HDV-Rz1498 or shRNA1498 expressing cells and the empty expression vector expressing cells are shown. RNAs that were up- or down-regulated in both conditions are shown in circles and squares, respectively. One gene that was down-regulated by SOFA-HDV-Rz1498 and up-regulated by shRNA1498 is shown with an arrow. The gene identities and log 2 ratio values are provided in FIGS. 15A-D.
Figure 12:
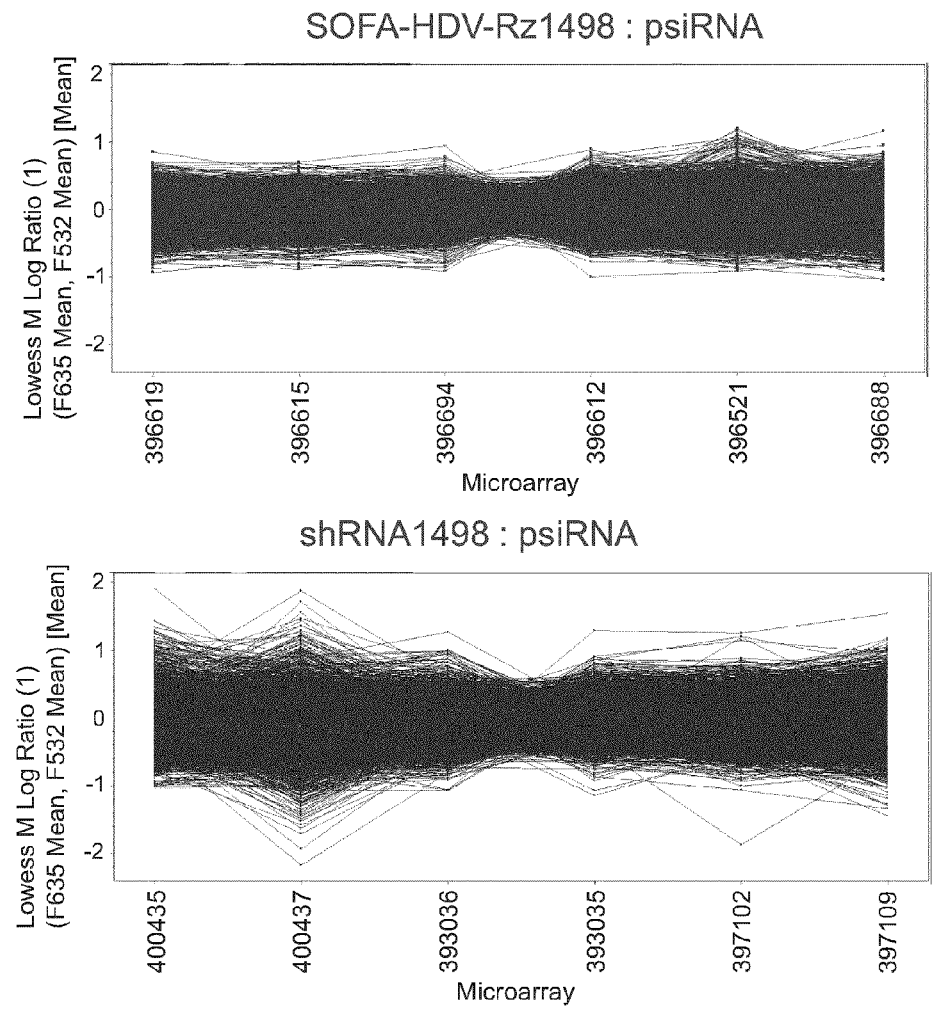
FIG. 12 shows the change in mRNA expression ratios compared to a control vector for SOFA-HDV-Rz1498 (upper panel) and shRNA1498 (lower panel) transfected HEK293T cells as detected by microarray: RNA extracts were obtained from HEK293T cells transfected with SOFA-HDV-Rz1498, shRNA1498 or the empty Rz/shRNA expression vector (psiRNA) and then analyzed using triplicate dye-swap microarray experiments. The results are expressed as Lowess log 2 ratio plots comparing all detectable mRNA species from SOFA-HDV-Rz1498 or shRNA1498-transfected cells with those from empty vector-transfected cells. Each individual line represents one detectable mRNA species and differences are reflected in the magnitude of change in log 2 ratio between the triplicates on the left and right halves of each plot.

The potential for both SOFA-HDV-Rz1498 and shRNA1498 to affect the expression of human mRNAs was next evaluated in HEK293T cells co-transfected with HIV-1 pNL4-3. Prior to gene expression profiling, the inhibition of viral production was confirmed for each condition and agreed with results presented in FIG. 5B. Microarray experiments were performed as triplicate dye swaps and the results were expressed as the log 2 ratio of SOFA-HDV-Rz1498 or shRNA1498 compared to the empty vector co-transfected cells (FIG. 12). All average log 2 ratios were low (below 1.0) suggesting that both SOFA-HDV-Rz1498 and shRNA1498 can inhibit HIV-1 production with minimal effects on human mRNA expression. The log 2 ratios for mRNAs with the greatest extent of up- or down-regulation are illustrated in FIG. 7 and listed in FIGS. 15A-D. Several of these mRNAs were found in both SOFA-HDV-Rz1498 and shRNA1498 conditions, suggesting that part of the observed changes may be target site specific.

EXAMPLE 8

Figure 8A:
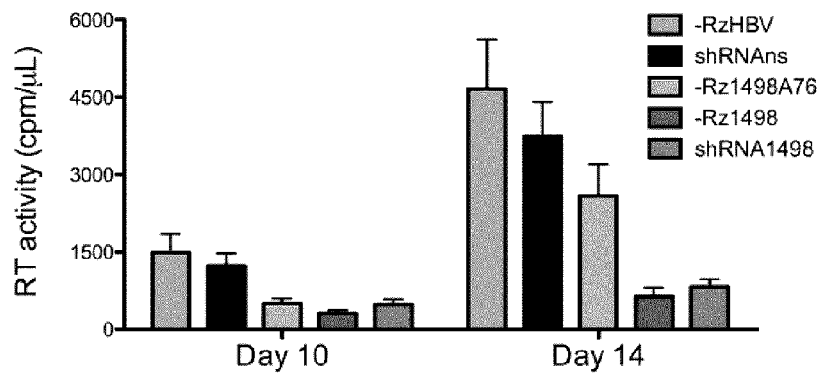
FIGS. 8A and B show the inhibition of HIV-1 replication by SOFA-HDV-Rz1498 and shRNA1498.
Figure 8B:
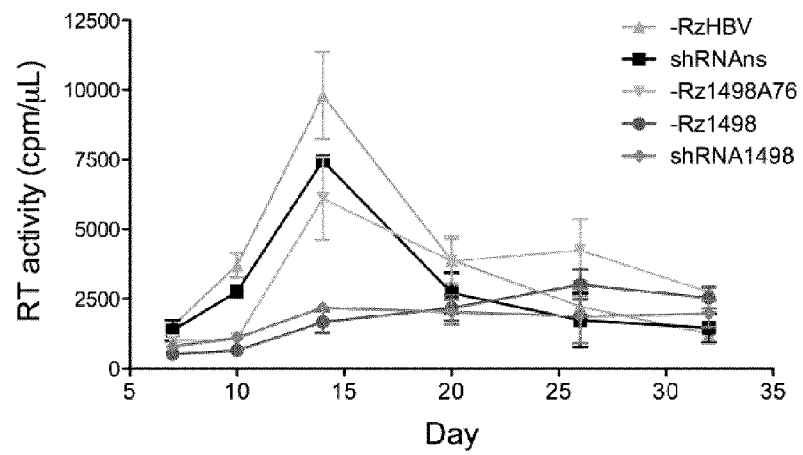
FIG. 8B: Time course of a representative infection (n=3) followed out to 32 days post-infection.
Figure 13A:
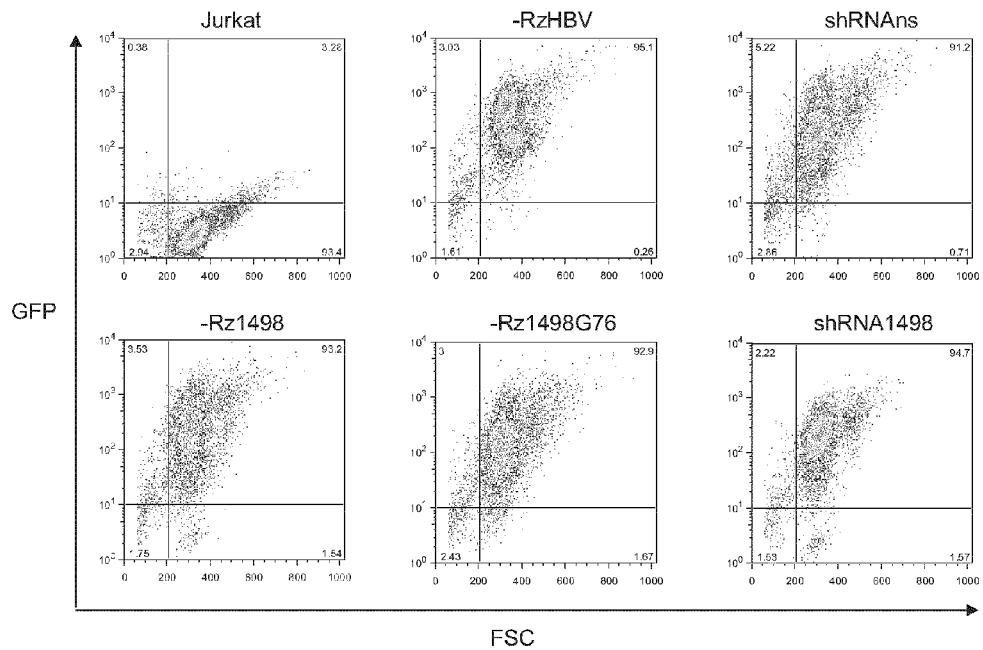
FIGS. 13A and B show stable Jurkat cell lines analysis.
Figure 13B:
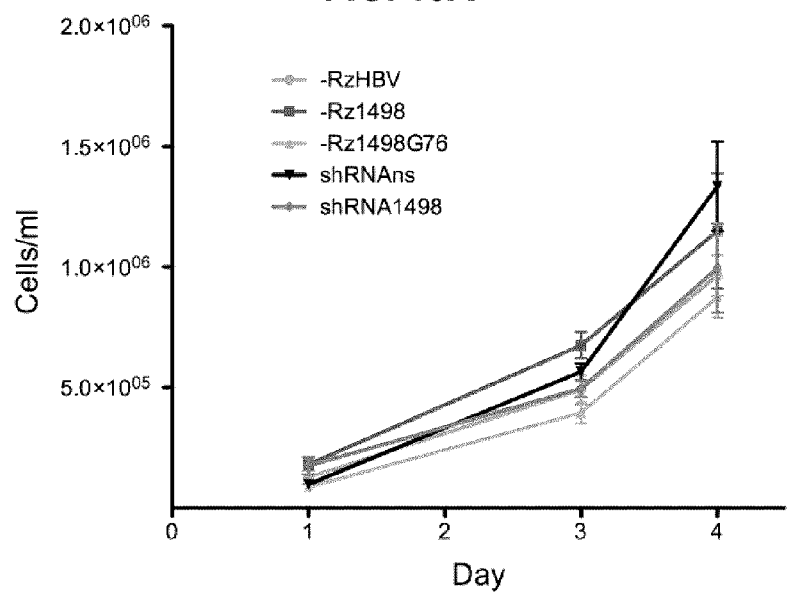
FIG. 13B: Live cell counts+/−SEM (n=2) out to four days after plating different cell lines at $1.0\times10^5$ cells/mL.

SOFA-HDV-Rz1498 and shRNA1498 Inhibit HIV-1 Replication in a T Lymphocyte Cell Line To evaluate the potential for SOFA-HDV-Rz1498 and shRNA1498 to inhibit HIV-1 replication, Jurkat cell lines were transfected with the same constructs used for their delivery to HEK293T cells, and stably transfected cells were selected in the presence of Zeocin. All cell lines had a similar distribution of GFP expression from the integrated plasmids and proliferated at similar levels (FIG. 13A). Following infection with HIV-1 pNL4-3, both SOFA-HDV-Rz1498 and shRNA1498 expressing cells were able to suppress viral replication compared to cells expressing SOFA-HDV-RzHBV and shRNAns (FIG. 8A). SOFA-HDV-Rz1498A76 expressing cells displayed a moderate inhibition, likely representing an antisense activity of the inactive Rz. SOFA-HDV-Rz1498 and shRNA1498 expressing cells maintained low levels of viral production past the peak of infection in control cell lines (FIG. 8B), providing evidence that the active molecules can restrict viral replication over several weeks in culture.

EXAMPLE 9 siRNAs Targeting the Identified Target Site in the Gag ORF Also Inhibit HIV-1 Production in a Dose Dependent Manner To determine whether or not the identified target site in the gag ORF could be used to design active siRNAs, siRNAs based on a Dicer substrate design (IDT) were designed with different start sites around the target site.

TABLE 6 siRNAs targeting HIV NL4-3 at starting position 1497 to 1499 with 25 and 27 bp duplexes.

| Target claimed: | ATAGCAGGAACTACTAGTACCCTTCAGGAA (NL4-3: 1495-1524) | SEQ ID NOs |
|---|---|---|
| 1497-25 | 5'-AGCAGGAACUACUAGUACCCUUC*dAd*G-3' | 75 |
| | 3'-UAUCGUCCUUGAUGAUCAUGGGAAGUC-5' | 76 |
| 1498-25 | 5'-GCAGGAACUACUAGUACCCUUCA*dGdG*-3' | 77 |
| | 3'-AUCGUCCUUGAUGAUCAUGGGAAGUCC-5' | 78 |
| 1498-27 | 5'-GCAGGAACUACUAGUACCCUUCAGGAA-3' | 79 |
| | 3'-*dAdT*CGUCCUUGAUGAUCAUGGGAAGUCC UU-5' | 80 |
| 1499-25 | 5'-CAGGAACUACUAGUACCCUUCAG*dGdA*-3' | 81 |
| | 3'-UCGUCCUUGAUGAUCAUGGGAAGUCCU-5' | 82 |
| Positive control 5983-25 | 5'-GCGGAGACAGCGACGAAGAGCUC*dAdT*-3' | 83 |
| | 3'-UUCGCCUCUGUCGCUGCUUCUCGAGUA-5' | 84 |
| 5983-27 (published)[1] | 5'-GCGGAGACAGCGACGAAGAGCUCAUCA | 85 |
| | 3'-*dTdT*CGCCUCUGUCGCUGCUUCUCGAGUA GU-5' | 86 |

Figure 14A:
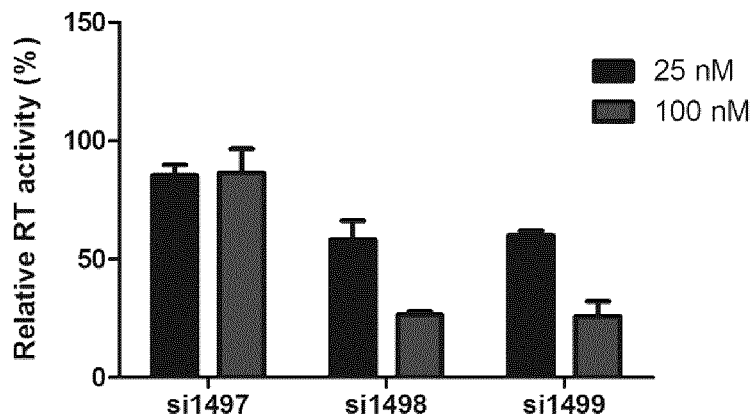
FIGS. 14A and B show that additional siRNAs directed against the targeted site inhibit HIV replication. HEK293T cells were seeded in 24 well plates and co-transfected with HIV-1 pNL4-3 plasmid DNA (100 ng) and one of the indicated siRNAs (Dharmacon) at 25 and 100 nM using Dharmafect reagent 1. Viral production was estimated 48 h following transfection by measuring the activity of HIV-1 RT in culture supernatants. Each replicate was expressed as a percentage of the value obtained for co-transfection with a 25 bp nonsense siRNA (Relative RT activity). Data are expressed as the mean+/−standard error mean (SEM) (n=2-6).
Figure 14B:
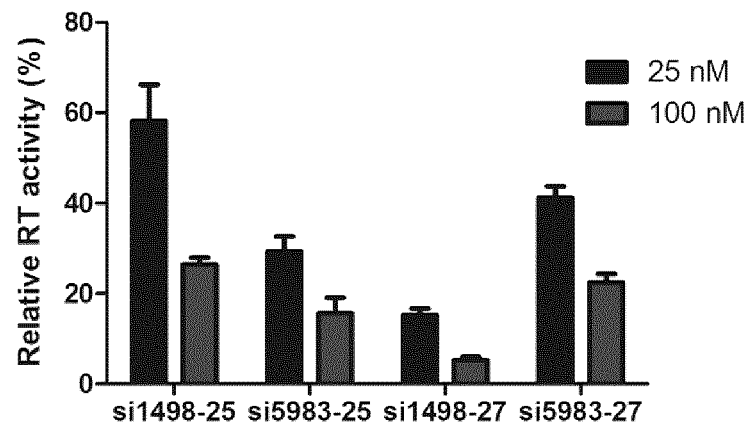
FIG. 14B: Results for 25 and 27 bp versions of si1498 targeting the Gag coding sequence of HIV-1 RNA and si5983 targeting the overlapping Tat/Rev coding sequence of HIV-1 RNA.
Figure 15C:

[1]Zhou, J, Neff, CP, Liu, X, Zhang, J, Li, H, Smith, DD, et al. (2011). Mol Ther 19: 2228-2238 si1498 (si1498-25) and si1499 (si1499-25) were able to inhibit HIV-1 production (FIG. 14A). Similarly, the 27 bp version of si1498 also inhibits HIV-1 production (FIG. 14B).

EXAMPLE 10

Other shRNAs Directed Against the Identified Target Site in the Gag ORF

The shRNA depicted in Tables 7 and 8 were prepared and tested.

TABLE 7

20 bp shRNA sequences targeting HIV-1 NL4-3 (Genbank M19921) from starting positions 1495 to 1501 (sh1498 disclosed above shown in bold).

Target claimed: ATAGCAGGAACTACTAGTACCCTTCA

| shRNA | Vector | NL4-3: 1495-1520 Stem | Loop |
|---|---|---|---|
| 1495-20 | <u>ACCTC</u> GTTT | 5'-ATAGCAGGAACTACTAGTAC-3' (SEQ ID NO: 87) 3'-TTGTATCGTCCTTGATGATCATG-5' (SEQ ID NO: 88) | GCTCGAGG |
| 1496-20 | <u>ACCTC</u> GTTT | 5'-TAGCAGGAACTACTAGTACC-3' (SEQ ID NO: 89) 3'-TTATCGTCCTTGATGATCATGG-5' (SEQ ID NO: 90) | GCTCGAGG |
| 1497-20 | <u>ACCTC</u> GTTT | 5'-AGCAGGAACTACTAGTACCC-3'(SEQ ID NO: 91) 3'-TTATCGTCCTTGATGATCATGGG-5' (SEQ ID NO: 92) | ACTCGAGA |

TABLE 7-continued 20 bp shRNA sequences targeting HIV-1 NL4-3 (Genbank M19921) from starting positions 1495 to 1501 (sh1498 disclosed above shown in bold).

Target claimed: ATAGCAGGAACTACTAGTACCCTTCA

| shRNA | Vector | NL4-3: 1495-1520 Stem | Loop |
|---|---|---|---|
| 1498-20 | ACCTC GTTT | 5'-GCAGGAACTACTAGTACCCT-3' (SEQ ID NO: 93)<br>3'-TTCGTCCTTGATGATCATGGGA-5' (SEQ ID NO: 94) | ACTCGAGA |
| 1499-20 | ACCTC GTTT | 5'-CAGGAACTACTAGTACCCTT-3' (SEQ ID NO: 95)<br>3'-TTGTCCTTGATGATCATGGGAA-5' (SEQ ID NO: 96) | GCTCGAGG |
| 1500-20 | ACCTC GTTT | 5'-AGGAACTACTAGTACCCTTC-3' (SEQ ID NO: 97)<br>3'-TTGTCCTTGATGATCATGGGAAG-5' (SEQ ID NO: 98) | TCTCGAGT |
| 1501-20 | ACCTC GTTT | 5'-GGAACTACTAGTACCCTTCA-3' (SEQ ID NO: 99)<br>3'-TTCCTTGATGATCATGGGAAGT-5' (SEQ ID NO: 100) | CCTCGAGC |

TABLE 8 shRNAs targeting HIV NL4-3 at starting position 1498 with 17 to 29 bp hairpins
(20 bp hairpin sh1498 disclosed above shown in bold)

Target claimed: TAGCAGGAACTACTAGTACCCTTCAGGAACA

| shRNA | Vector | Stem | NL4-3: 1496-1526 | Loop |
|---|---|---|---|---|
| 1498-17 | ACCTC GTTT | 5'-GCAGGAACTACTAGTAC-3' (SEQ ID NO: 101)<br>3'-TTCGTCCTTGATGATCATG-5' (SEQ ID NO: 102) | G<br>G | CTCGAG |
| 1498-18 | ACCTC GTTT | 5'-GCAGGAACTACTAGTACC-3' (SEQ ID NO: 103)<br>3'-TTCGTCCTTGATGATCATGG-5' (SEQ ID NO: 104) | G<br>G | CTCGAG |
| 1498-19 | ACCTC GTTT | 5'-GCAGGAACTACTAGTACCC-3' (SEQ ID NO: 105)<br>3'-TTCGTCCTTGATGATCATGGG-5' (SEQ ID NO: 106) | A<br>A | CTCGAG |
| 1498-20 | ACCTC GTTT | 5'-GCAGGAACTACTAGTACCCT-3' (SEQ ID NO: 93)<br>3'-TTCGTCCTTGATGATCATGGGA-5' (SEQ ID NO: 94) | A<br>A | CTCGAG |
| 1498-21 | ACCTC GTTT | 5'-GCAGGAACTACTAGTACCCTT-3' (SEQ ID NO: 107)<br>3'-TTCGTCCTTGATGATCATGGGAA-5' (SEQ ID NO: 108) | G<br>G | CTCGAG |
| 1498-23 | ACCTC GTTT | 5'-GCAGGAACTACTAGTACCCTTCA-3' (SEQ ID NO: 109)<br>3'-TTCGTCCTTGATGATCATGGGAAGT-5' (SEQ ID NO: 110) | C<br>C | CTCGAG |
| 1498-25 | ACCTC GTTT | 5'-GCAGGAACTACTAGTACCCTTCAGG-3' (SEQ ID NO: 111)<br>3'-TTCGTCCTTGATGATCATGGGAAGTCC-5' (SEQ ID NO: 112) | T<br>T | CTCGAG |
| 1498-27 | ACCTC GTTT | 5'-GCAGGAACTACTAGTACCCTTCAGGAA-3' (SEQ ID NO: 113)<br>3'-TTCGTCCTTGATGATCATGGGAAGTCCTT-5' (SEQ ID NO: 114) | G<br>G | CTCGAG |
| 1498-29 | ACCTC GTTT | 5'-GCAGGAACTACTAGTACCCTTCAGGAACA-3' (SEQ ID NO: 115)<br>3'-TTCGTCCTTGATGATCATGGGAAGTCCTTGT-5' (SEQ ID NO: 116) | T<br>T | CTCGAG |

The shRNA inserts were generated by annealing complementary sense (S) and antisense (AS) oligonucleotides corresponding to the above-noted sequences (vector+stem+loop) using the methods described in Example 1.

Figure 16A:
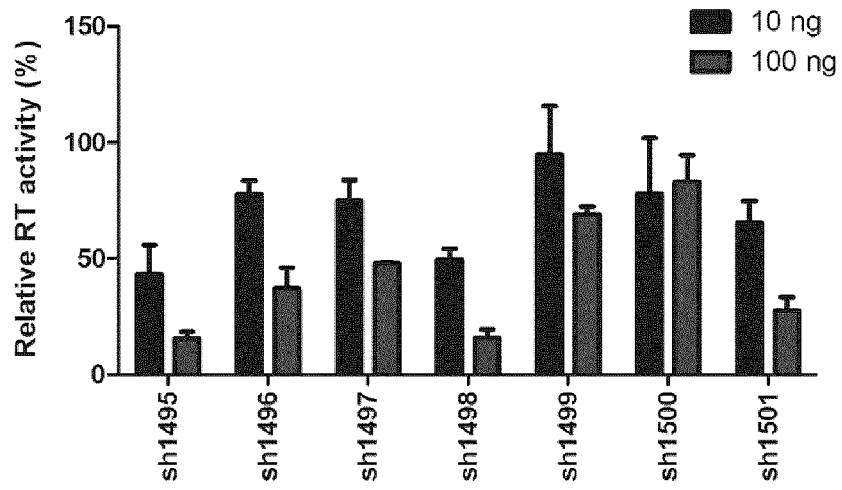
FIG. 16A shows the activity of 20 bp shRNAs targeting HIV-1 NL4-3 from starting positions 1495 to 1501. HEK293T cells were seeded in 24-well plates and co-transfected with HIV-1 pNL4-3 plasmid DNA (100 ng) and one of the indicated psiRNA-shRNA expression plasmids (10 and 100 ng). Viral production was estimated 48 h following transfection by measuring the activity of HIV-1 RT in culture supernatants. Each replicate was expressed as a percentage of the value obtained for co-transfection with the empty shRNA expression plasmid tested in parallel (Relative RT activity). Data are expressed as the mean+/−standard error mean (SEM) (n=2-6).
Figure 16B:
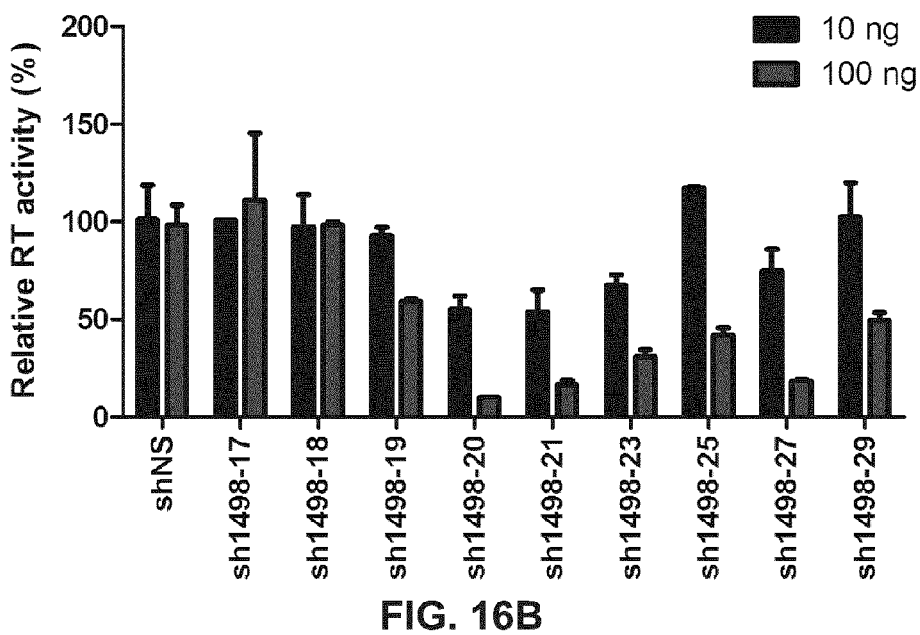
FIG. 16B shows the activity of shRNAs with 17 to 29 bp hairpins targeting HIV NL4-3 at starting position 1498. HEK293T cells were seeded in 24-well plates and co-transfected with HIV-1 pNL4-3 plasmid DNA (100 ng) and one of the indicated psiRNA-shRNA expression plasmids (10 and 100 ng). Viral production was estimated 48 h following transfection by measuring the activity of HIV-1 RT in culture supernatants. Each replicate was expressed as a percentage of the value obtained for co-transfection with the empty shRNA expression plasmid tested in parallel (Relative RT activity). Data are expressed as the mean+/−standard error mean (SEM) (n=2-6).

FIG. 16A shows that sh1495, sh1496, sh1497, sh1498 and sh1501 exhibit HIV-1 inhibitory activity at 10 and 100 ng, and sh1499 exhibits HIV-1 inhibitory activity at 100 ng, confirming that shRNAs directed against different starting positions within the targeted site may be used to inhibit HIV-1. Also, the results depicted in FIG. 16B demonstrate that shRNAs targeting HIV NL4-3 at starting position 1498 with 19 to 29 bp hairpins all exhibit HIV-1 inhibitory activity at 100 ng, with some shRNA being also active at 10 ng (sh1498-20, sh1498-21 and sh1498-23). This data provide evidence that shRNAs directed against the targeted site and having hairpins of different lengths are able to block HIV-1 viral production.

Although the present invention has been described hereinabove by way of specific embodiments thereof, it can be modified, without departing from the spirit and nature of the subject invention as defined in the appended claims. In the claims, the word "comprising" is used as an open-ended term, substantially equivalent to the phrase "including, but not limited to". The singular forms "a", an and the include corresponding plural references unless the context clearly dictates otherwise.

REFERENCES

1. De Clercq, E. (2010). Antiretroviral drugs. Curr Opin Pharmacol 10: 507-15.
2. Le Douce, V., Janossy, A., Hallay, H., Ali, S., Riclet, R., Rohr, O. et al. (2012). Achieving a cure for HIV infection: do we have reasons to be optimistic? J Antimicrob Chemother 67: 1063-74.
3. Scherer, L. J. and Rossi, J. J. (2011). Ex vivo gene therapy for HIV-1 treatment. Hum Mol Genet 20: R100-7.
4. Burnett, J. C. and Rossi, J. J. (2012). RNA-based therapeutics: current progress and future prospects. Chem Biol 19: 60-71.
5. Haasnoot, J. and Berkhout, B. (2009). Nucleic acids-based therapeutics in the battle against pathogenic viruses. Handb Exp Pharmacol: 243-63.
6. Rossi, J. J. (2000). Ribozyme therapy for HIV infection. Adv Drug Deliv Rev 44: 71-8.
7. Zeng, W., Chen, Y. C., Bai, Y., Trang, P., Vu, G. P., Lu, S. et al. (2012). Effective Inhibition of Human Immunodeficiency Virus 1 Replication by Engineered RNase P Ribozyme. PLoS One 7: e51855.
8. Asif-Ullah, M., Lévesque, M., Robichaud, G. and Perreault, J. P. (2007). Development of ribozyme-based gene-inactivations; the example of the hepatitis delta virus ribozyme. Curr Gene Ther 7: 205-16.
9. Bergeron, L. J. and Perreault, J. P. (2005). Target-dependent on/off switch increases ribozyme fidelity. Nucleic Acids Res 33: 1240-8.
10. Bergeron, L. J., Reymond, C. and Perreault, J. P. (2005). Functional characterization of the SOFA delta ribozyme. RNA 11: 1858-68.
11. Robichaud, G. A., Perreault, J. P. and Ouellette, R. J. (2008). Development of an isoform-specific gene suppression system: the study of the human Pax-5B transcriptional element. Nucleic Acids Res 36: 4609-20.
12. D'Anjou, F., Routhier, S., Perreault, J. P., Latil, A., Bonnel, D., Fournier, I. et al. (2011). Molecular Validation of PACE4 as a Target in Prostate Cancer. Transl Oncol 4: 157-72.
13. Lévesque, M. V., Lévesque, D., Brière, F. P. and Perreault, J. P. (2010). Investigating a new generation of ribozymes in order to target HCV. PLoS One 5: e9627.
14. Motard, J., Rouxel, R., Paun, A., von Messling, V., Bisaillon, M. and Perreault, J. P. (2011). A novel ribozyme-based prophylaxis inhibits influenza A virus replication and protects from severe disease. PLoS One 6: e27327.
15. Fiola, K., Perreault, J. P. and Cousineau, B. (2006). Gene targeting in the Gram-Positive bacterium Lactococcus lactis, using various delta ribozymes. Appl Environ Microbiol 72: 869-79.
16. Lainé, S., Scarborough, R. J., Lévesque, D., Didierlaurent, L., Soye, K. J., Mougel, M. et al. (2011). In vitro and in vivo cleavage of HIV-1 RNA by new SOFA-HDV ribozymes and their potential to inhibit viral replication. RNA Biol 8: 343-53.
17. Bramlage, B., Luzi, E. and Eckstein, F. (2000). HIV-1 LTR as a target for synthetic ribozyme-mediated inhibition of gene expression: site selection and inhibition in cell culture. Nucleic Acids Res 28: 4059-67.
18. Unwalla, H. J., Li, H., Li, S. Y., Abad, D. and Rossi, J. J. (2008). Use of a U16 snoRNA-containing ribozyme library to identify ribozyme targets in HIV-1. Mol Ther 16: 1113-9.
19. Müller-Kuller, T., Capalbo, G., Klebba, C., Engels, J. W. and Klein, S. A. (2009). Identification and characterization of a highly efficient anti-HIV pol hammerhead ribozyme. Oligonucleotides 19: 265-72.
20. Naito, Y., Nohtomi, K., Onogi, T., Uenishi, R., Ui-Tei, K., Saigo, K. et al. (2007). Optimal design and validation of antiviral siRNA for targeting HIV-1. Retrovirology 4: 80.
21. ter Brake, O., Konstantinova, P., Ceylan, M. and Berkhout, B. (2006). Silencing of HIV-1 with RNA interference: a multiple shRNA approach. Mol Ther 14: 883-92.
22. McIntyre, G. J., Groneman, J. L., Yu, Y. H., Jaramillo, A., Shen, S. and Applegate, T. L. (2009). 96 shRNAs designed for maximal coverage of HIV-1 variants. Retrovirology 6: 55.
23. DeYoung, M. B. and Hampel, A. (1997). Computer analysis of the conservation and uniqueness of ribozyme-targeted HIV sequences. Methods Mol Biol 74: 27-36.
24. Sajic, R., Lee, K., Asai, K., Sakac, D., Branch, D. R., Upton, C. et al. (2007). Use of modified U1 snRNAs to inhibit HIV-1 replication. Nucleic Acids Res 35: 247-55.
25. Lee, S. K., Dykxhoorn, D. M., Kumar, P., Ranjbar, S., Song, E., Maliszewski, L. E. et al. (2005). Lentiviral delivery of short hairpin RNAs protects CD4 T cells from multiple clades and primary isolates of HIV. Blood 106: 818-26.
26. Lucier, J. F., Bergeron, L. J., Brière, F. P., Ouellette, R., Elela, S. A. and Perreault, J. P. (2006). RiboSubstrates: a web application addressing the cleavage specificities of ribozymes in designated genomes. BMC Bioinformatics 7: 480.
27. Sánchez-Luque, F. J., Reyes-Darias, J. A., Puerta-Fernández, E. and Berzal-Herranz, A. (2010). Inhibition of HIV-1 replication and dimerization interference by dual inhibitory RNAs. Molecules 15: 4757-72.
28. Lévesque, M. V. and Perreault, J. P. (2012). Target-induced SOFA-HDV ribozyme. Methods Mol Biol 848: 369-84.
29. DiGiusto, D. L., Krishnan, A., Li, L., Li, H., Li, S., Rao, A. et al. (2010). RNA-based gene therapy for HIV with 29. lentiviral vector-modified CD34(+) cells in patients undergoing transplantation for AIDS-related lymphoma. Sci Transl Med 2: 36ra43.
30. Peden, K., Emerman, M. and Montagnier, L. (1991). Changes in growth properties on passage in tissue culture of viruses derived from infectious molecular clones of HIV-1LAI, HIV-1MAL, and HIV-1 ELI. Virology 185: 661-72.
31. Theodore, T. S., Englund, G., Buckler-White, A., Buckler, C. E., Martin, M. A. and Peden, K. W. (1996). Construction and characterization of a stable full-length macrophage-tropic HIV type 1 molecular clone that directs the production of high titers of progeny virions. AIDS Res Hum Retroviruses 12: 191-4.
32. Mochizuki, N., Otsuka, N., Matsuo, K., Shiino, T., Kojima, A., Kurata, T. et al. (1999). An infectious DNA clone of HIV type 1 subtype C. AIDS Res Hum Retroviruses 15: 1321-4.
33. Ndung'u, T., Renjifo, B. and Essex, M. (2001). Construction and analysis of an infectious human Immunodeficiency virus type 1 subtype C molecular clone. J Virol 75: 4964-72.
34. Gao, F., Robertson, D. L., Carruthers, C. D., Morrison, S. G., Jian, B., Chen, Y. et al. (1998). A comprehensive panel of near-full-length clones and reference sequences for non-subtype B isolates of human immunodeficiency virus type 1. J Virol 72: 5680-98.
35. Kusagawa, S., Takebe, Y., Yang, R., Motomura, K., Ampofo, W., Brandful, J. et al. (2001). Isolation and characterization of a full-length molecular DNA clone of Ghanaian HIV type 1 intersubtype A/G recombinant CRF02_AG, which is replication competent in a restricted host range. AIDS Res Hum Retroviruses 17: 649-55.
36. Rossi, J. J., June, C. H. and Kohn, D. B. (2007). Genetic therapies against HIV. Nat Biotechnol 25: 1444-54.
37. Mitsuyasu, R. T., Merigan, T. C., Carr, A., Zack, J. A., Winters, M. A., Workman, C. et al. (2009). Phase 2 gene therapy trial of an anti-HIV ribozyme in autologous CD34+ cells. Nat Med 15: 285-92.
38. Good, P. D., Krikos, A. J., Li, S. X., Bertrand, E., Lee, N. S., Giver, L. et al. (1997). Expression of small, therapeutic RNAs in human cell nuclei. Gene Ther 4: 45-54.
39. Puerta-Fernandez, E., Barroso-del Jesus, A., Romero-Lopez, C., Tapia, N., Martinez, M. A. and Berzal-Herranz, A. (2005). Inhibition of HIV-1 replication by RNA targeted against the LTR region. AIDS 19: 863-70.
40. Chang, Z., Westaway, S., Li, S., Zaia, J. A., Rossi, J. J. and Scherer, L. J. (2002). Enhanced expression and HIV-1 inhibition of chimeric tRNA(Lys3)-ribozymes under dual U6 snRNA and tRNA promoters. Mol Ther 6: 481-9.
41. Michienzi, A., Cagnon, L., Bahner, I. and Rossi, J. J. (2000). Ribozyme-mediated inhibition of HIV 1 suggests nucleolar trafficking of HIV-1 RNA. Proc Natl Acad Sci USA 97: 8955-60.
42. Watts, J. M., Dang, K. K., Gorelick, R. J., Leonard, C. W., Bess, J. W., Jr., Swanstrom, R. et al. (2009). Architecture and secondary structure of an entire HIV-1 RNA genome. Nature 460: 711-6.
43. Mandal, D., Feng, Z. and Stoltzfus, C. M. (2010). Excessive RNA splicing and inhibition of HIV-1 replication induced by modified U1 small nuclear RNAs. J Virol 84: 12790-800.
44. Hemelaar, J., Gouws, E., Ghys, P. D. and Osmanov, S. (2011). Global trends in molecular epidemiology of HIV-1 during 2000-2007. AIDS 25: 679-89.
45. Scarborough, R. J., Lévesque, M. V., Perreault, J. P. and Gatignol, A. (2014). Design and Evaluation of Clinically Relevant SOFA-HDV Ribozymes Targeting HIV RNA. Methods Mol Biol 1103: 31-43.
46. Sabariegos, R., Giménez-Barcons, M., Tápia, N., Clotet, B. and Martinez, M. A. (2006). Sequence homology required by human immunodeficiency virus type 1 to escape from short interfering RNAs. J Virol 80: 571-7.
47. Waterhouse, A. M., Procter, J. B., Martin, D. M., Clamp, M. and Barton, G. J. (2009). Jalview Version 2—a multiple sequence alignment editor and analysis workbench. Bioinformatics 25: 1189-91.
48. Altschul, S. F., Madden, T. L., Schäffer, A. A., Zhang, J., Zhang, Z., Miller, W. et al. (1997). Gapped BLAST and PSI-BLAST: a new generation of protein database search programs. Nucleic Acids Res 25: 3389-402.
49. Li, M. J., Kim, J., Li, S., Zaia, J., Yee, J. K., Anderson, J. et al. (2005). Long-term inhibition of HIV-1 infection in primary hematopoietic cells by lentiviral vector delivery of a triple combination of anti-HIV shRNA, anti-CCR5 ribozyme, and a nucleolar-localizing TAR decoy. Mol Ther 12: 900-9.
50. Clerzius, G., Shaw, E., Daher, A., Burugu, S., Gelinas, J. F., Ear, T. et al. (2013). The PKR activator, PACT, becomes a PKR inhibitor during HIV-1 replication. Retrovirology 10: 96.
51. Scarborough, R J, Lévesque, MV, Boudrias-Dalle, E, Chute, I C, Daniels, S M, Ouellette, R J, et al. (2014). A Conserved Target Site in HIV-1 Gag RNA is Accessible to Inhibition by Both an HDV Ribozyme and a Short Hairpin RNA. *Mol Ther Nucleic Acids* 3: e178.

What is claimed is:

1. A short hairpin RNA (shRNA) molecule encoded by a nucleic acid comprising a stem consisting of one of the following sequences (i) to (iii):

(i)
(SEQ ID NO: 93)
5'-GCAGGAACTACTAGTACCCT-3'

(SEQ ID NO: 118)
3'-CGTCCTTGATGATCATGGGA-5';

(ii)
(SEQ ID NO: 107)
5'-GCAGGAACTACTAGTACCCTT-3'

(SEQ ID NO: 125)
3'-CGTCCTTGATGATCATGGGAA-5'; or (iii)
(SEQ ID NO: 109)
5'-GCAGGAACTACTAGTACCCTTCA-3'

(SEQ ID NO: 126)
3'-CGTCCTTGATGATCATGGGAAGT-5'.

2. The shRNA molecule of claim 1, wherein the shRNA comprises a 3'-overhang.

3. The shRNA molecule of claim 2, wherein the shRNA is encoded by a nucleic acid comprising one of the following sequences (i) to (iii):

(i)
(SEQ ID NO: 130)
GCAGGAACTACTAGTACCCTACTCGAGAAGGGTACTAGTAGTTCCTGCT;

(ii)
(SEQ ID NO: 137)
GCAGGAACTACTAGTACCCTTGCTCGAGGAAGGGTACTAGTAGTTCCTGCTT; or (iii)
(SEQ ID NO: 138)
GCAGGAACTACTAGTACCCTTCACCTCGAGCTGAAGGGTACTAGTAGTTCCTGCTT.

4. A vector comprising a nucleic acid encoding the shRNA molecule of claim 1.

5. A cell comprising the shRNA molecule of claim 1.

6. A composition comprising (a) the shRNA molecule of claim 1; and (b) an excipient.

7. A method for inhibiting HIV-1 replication in a cell, the method comprising contacting said cell with an effective amount of the shRNA molecule of claim 1, or of a nucleic acid encoding said shRNA molecule.

8. A method for treating HIV-1 infection in a subject in need thereof, the method comprising administering to said subject an effective amount of the shRNA molecule of claim 1, or of a nucleic acid encoding said shRNA molecule.

9. The shRNA molecule of claim 2, wherein the 3'-overhang has 1- to 5 nucleotides.

10. The shRNA molecule of claim 9, wherein the 3'-overhang has 2 nucleotides.

11. The shRNA molecule of claim 9, wherein the 3'-overhang consists of the sequence UU.

12. The shRNA molecule of claim 2, wherein the nucleic acid encoding the shRNA further comprises a loop having a length of 4 to 11 nucleotides.

13. The shRNA molecule of claim 12, wherein the loop has a length of 6 to 10 nucleotides, or 7 to 9 nucleotides.

14. The shRNA molecule of claim 13, wherein the loop has a length of 8 nucleotides.

15. The shRNA molecule of claim 12, wherein the loop comprises or consists of one of the following sequences: CTCGAG, GCTCGAGG, ACTCGAGA, TCTCGAGT or CCTCGAGC.

16. . A method for inhibiting HIV-1 replication in a cell, the method comprising contacting said cell with an effective amount of the vector of claim 4.

17. A method for treating HIV-1 infection in a subject in need thereof, the method comprising administering to said subject an effective amount of the vector of claim 4.

* * * * *

SEQUENCE LISTING

<160> NUMBER OF SEQ ID NOS: 142

<210> SEQ ID NO 1
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 1
gcaggaacta ctagtaccct actcgagaag ggtactagta gttcctgc                    48

<210> SEQ ID NO 2
<211> LENGTH: 48

-continued

<212> TYPE: DNA
<213> ORGANISM: Artificial Sequence
<220> FEATURE:
<223> OTHER INFORMATION: Synthetic oligonucleotide

<400> SEQUENCE: 2
gcaggaacta ctagtaccct tctcgagtag ggtactagta gttcctgc                48

<210> SEQ ID NO 3
<211> LENGTH: 25
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (24)..(25)
<223> OTHER INFORMATION: deoxyribonucleotide

<400> SEQUENCE: 3
agcaggaacu acuaguaccc uucag                                         25

<210> SEQ ID NO 4
<211> LENGTH: 27
<212> TYPE: RNA
<213> ORGANISM: Artificial Sequence
<220> FEATURE:
<223> OTHER INFORMATION: Synthetic oligonucleotide

<400> SEQUENCE: 4
uaucguccuu gaugaucaug ggaaguc                                       27

<210> SEQ ID NO 5
<211> LENGTH: 25
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (24)..(25)
<223> OTHER INFORMATION: deoxyribonucleotide

<400> SEQUENCE: 5
gcaggaacua cuaguacccu ucagg                                         25

<210> SEQ ID NO 6
<211> LENGTH: 27
<212> TYPE: RNA
<213> ORGANISM: Artificial Sequence
<220> FEATURE:
<223> OTHER INFORMATION: Synthetic oligonucleotide

<400> SEQUENCE: 6
aucguccuug augaucaugg gaagucc                                       27

<210> SEQ ID NO 7
<211> LENGTH: 25
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (24)..(25)
<223> OTHER INFORMATION: deoxyribonucleotide

<400> SEQUENCE: 7
caggaacuac uaguacccuu cagga                                          25

<210> SEQ ID NO 8
<211> LENGTH: 27
<212> TYPE: RNA
<213> ORGANISM: Artificial Sequence
<220> FEATURE:
<223> OTHER INFORMATION: Synthetic oligonucleotide

<400> SEQUENCE: 8
ucguccuuga ugaucauggg aaguccu                                        27

<210> SEQ ID NO 9
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 9
tataagttct gtatgagttc acggaagacc gacctcgggc cagctagttt               50

<210> SEQ ID NO 10
<211> LENGTH: 61
<212> TYPE: DNA
<213> ORGANISM: Artificial Sequence
<220> FEATURE:
<223> OTHER INFORMATION: Synthetic oligonucleotide

<400> SEQUENCE: 10
caacaacagt gttcggatga actgatgcta tgaagactcc aaaaaccagc tagaaagggt    60
c                                                                   61

<210> SEQ ID NO 11
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 11
ccagctagaa agggtccctt agccatccgc gaacggatgc cc                       42

<210> SEQ ID NO 12
<211> LENGTH: 67
<212> TYPE: DNA
<213> ORGANISM: Artificial Sequence
<220> FEATURE:
<223> OTHER INFORMATION: Synthetic oligonucleotide

<400> SEQUENCE: 12
taatacgact cactataggg ccagctagtt tcagggtcca cctcctcgcg gtgggcatcc    60
gttcgcg                                                             67

<210> SEQ ID NO 13
<211> LENGTH: 55
<212> TYPE: DNA
<213> ORGANISM: Artificial Sequence
<220> FEATURE:
<223> OTHER INFORMATION: Synthetic oligonucleotide

<400> SEQUENCE: 13
acctcgcctc aataaagctt gccttcctcg agcaaggcaa gctttattga ggctt         55

```
<210> SEQ ID NO 14
<211> LENGTH: 55
<212> TYPE: DNA
<213> ORGANISM: Artificial Sequence
<220> FEATURE:
<223> OTHER INFORMATION: Synthetic oligonucleotide

<400> SEQUENCE: 14
caaaaagcct caataaagct tgccttgctc gaggaaggca agctttattg aggcg      55

<210> SEQ ID NO 15
<211> LENGTH: 55
<212> TYPE: DNA
<213> ORGANISM: Artificial Sequence
<220> FEATURE:
<223> OTHER INFORMATION: Synthetic oligonucleotide

<400> SEQUENCE: 15
acctcgtagt gtgtgcccgt ctgttcctcg agcaacagac gggcacacac tactt      55

<210> SEQ ID NO 16
<211> LENGTH: 55
<212> TYPE: DNA
<213> ORGANISM: Artificial Sequence
<220> FEATURE:
<223> OTHER INFORMATION: Synthetic oligonucleotide

<400> SEQUENCE: 16
caaaaagtag tgtgtgcccg tctgttgctc gaggaacaga cgggcacaca ctacg      55

<210> SEQ ID NO 17
<211> LENGTH: 55
<212> TYPE: DNA
<213> ORGANISM: Artificial Sequence
<220> FEATURE:
<223> OTHER INFORMATION: Synthetic oligonucleotide

<400> SEQUENCE: 17
acctcgtacc gcacgtcatt cgtatcctcg agcatacgaa tgacgtgcgg tactt      55

<210> SEQ ID NO 18
<211> LENGTH: 55
<212> TYPE: DNA
<213> ORGANISM: Artificial Sequence
<220> FEATURE:
<223> OTHER INFORMATION: Synthetic oligonucleotide

<400> SEQUENCE: 18
caaaaagtac cgcacgtcat tcgtatgctc gaggatacga atgacgtgcg gtacg      55

<210> SEQ ID NO 19
<211> LENGTH: 55
<212> TYPE: DNA
<213> ORGANISM: Artificial Sequence
<220> FEATURE:
<223> OTHER INFORMATION: Synthetic oligonucleotide

<400> SEQUENCE: 19
acctcgcagg aactactagt accctactcg agaagggtac tagtagttcc tgctt      55

<210> SEQ ID NO 20
<211> LENGTH: 55
<212> TYPE: DNA
<213> ORGANISM: Artificial Sequence
<220> FEATURE:
<223> OTHER INFORMATION: Synthetic oligonucleotide
```

<400> SEQUENCE: 20
caaaaagcag gaactactag taccttctc gagtagggta ctagtagttc ctgcg    55

<210> SEQ ID NO 21
<211> LENGTH: 55
<212> TYPE: DNA
<213> ORGANISM: Artificial Sequence
<220> FEATURE:
<223> OTHER INFORMATION: Synthetic oligonucleotide

<400> SEQUENCE: 21
acctcgcgga gacagcgacg aagaggctcg aggctcttcg tcgctgtctc cgctt    55

<210> SEQ ID NO 22
<211> LENGTH: 55
<212> TYPE: DNA
<213> ORGANISM: Artificial Sequence
<220> FEATURE:
<223> OTHER INFORMATION: Synthetic oligonucleotide

<400> SEQUENCE: 22
caaaaagcgg agacagcgac gaagagcctc gagcctcttc gtcgctgtct ccgcg    55

<210> SEQ ID NO 23
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 23
tctacggggt ctgacgc    17

<210> SEQ ID NO 24
<211> LENGTH: 25
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (24)..(25)
<223> OTHER INFORMATION: deoxyribonucleotide

<400> SEQUENCE: 24
agcaggaacu acuaguaccc uucag    25

<210> SEQ ID NO 25
<211> LENGTH: 27
<212> TYPE: RNA
<213> ORGANISM: Artificial Sequence
<220> FEATURE:
<223> OTHER INFORMATION: Synthetic oligonucleotide

<400> SEQUENCE: 25
uaucguccuu gaugaucaug ggaaguc    27

<210> SEQ ID NO 26
<211> LENGTH: 25
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (24)..(25)
<223> OTHER INFORMATION: deoxyribonucleotide -continued

```
<400> SEQUENCE: 26
gcaggaacua cuaguacccu ucagg                                          25

<210> SEQ ID NO 27
<211> LENGTH: 27
<212> TYPE: RNA
<213> ORGANISM: Artificial Sequence
<220> FEATURE:
<223> OTHER INFORMATION: Synthetic oligonucleotide

<400> SEQUENCE: 27
aucguccuug augaucaugg gaagucc                                        27

<210> SEQ ID NO 28
<211> LENGTH: 25
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (24)..(25)
<223> OTHER INFORMATION: deoxyribonucleotide

<400> SEQUENCE: 28
caggaacuac uaguacccuu cagga                                          25

<210> SEQ ID NO 29
<211> LENGTH: 27
<212> TYPE: RNA
<213> ORGANISM: Artificial Sequence
<220> FEATURE:
<223> OTHER INFORMATION: Synthetic oligonucleotide

<400> SEQUENCE: 29
ucguccuuga ugaucauggg aaguccu                                        27

<210> SEQ ID NO 30
<211> LENGTH: 25
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (24)..(25)
<223> OTHER INFORMATION: deoxyribonucleotide

<400> SEQUENCE: 30
guaccgcacg ucauucguau ccuat                                          25

<210> SEQ ID NO 31
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 31
ttcauggcgu gcaguaagca uaggaua                                        27

<210> SEQ ID NO 32
<211> LENGTH: 35
<212> TYPE: DNA
<213> ORGANISM: Artificial Sequence
<220> FEATURE:
```

<223> OTHER INFORMATION: Synthetic oligonucleotide

<400> SEQUENCE: 32
gaaagggtcc cttagccatc gcgaacgga tgccc                35

<210> SEQ ID NO 33
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 33
aaagcctaca gcacccggta ttccc               25

<210> SEQ ID NO 34
<211> LENGTH: 66
<212> TYPE: DNA
<213> ORGANISM: Artificial Sequence
<220> FEATURE:
<223> OTHER INFORMATION: Synthetic oligonucleotide

<400> SEQUENCE: 34
taatacgact cactataggg catagcagga actactagta cccttgggtc ggcagggtcc    60
acctcc                                                              66

<210> SEQ ID NO 35
<211> LENGTH: 66
<212> TYPE: DNA
<213> ORGANISM: Artificial Sequence
<220> FEATURE:
<223> OTHER INFORMATION: Synthetic oligonucleotide

<400> SEQUENCE: 35
gggtccctta gccatgcgaa gccgcatgcc caggtcggac cgcgaggagg tggaccctgc    60
cgaccc                                                              66

<210> SEQ ID NO 36
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 36
tagatcctag actagagccc tggaa               25

<210> SEQ ID NO 37
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 37
caggaagaag cggagacagc gacga               25

<210> SEQ ID NO 38
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 38
aagcctcaat aaagcttgcc ttgag                                            25

<210> SEQ ID NO 39
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 39
aagtagtgtg tgcccgtctg ttgtg                                            25

<210> SEQ ID NO 40
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 40
gtgtgcccgt ctgttgtgtg actct                                            25

<210> SEQ ID NO 41
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 41
gtgcccgtct gttgtgtgac tctgg                                            25

<210> SEQ ID NO 42
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 42
gtgactctgg taactagaga tccct                                            25

<210> SEQ ID NO 43
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 43
gcgagagcgt cggtattaag cgggg                                            25

<210> SEQ ID NO 44
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 44
gagagcgtcg gtattaagcg gggga                                            25

<210> SEQ ID NO 45
<211> LENGTH: 25
<212> TYPE: DNA

```
<213> ORGANISM: Artificial Sequence
<220> FEATURE:
<223> OTHER INFORMATION: Synthetic oligonucleotide

<400> SEQUENCE: 45
aaggccaggg ggaaagaaac aatat                                          25

<210> SEQ ID NO 46
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 46
cagcccagaa gtaataccca tgttt                                          25

<210> SEQ ID NO 47
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 47
cagcattatc agaaggagcc acccc                                          25

<210> SEQ ID NO 48
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 48
gagaaccaag gggaagtgac atagc                                          25

<210> SEQ ID NO 49
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 49
tagcaggaac tactagtacc cttca                                          25

<210> SEQ ID NO 50
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 50
tagtacccTt caggaacaaa tagga                                          25

<210> SEQ ID NO 51
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 51
ctgggattaa ataaatagt aagaa                                           25
```

<210> SEQ ID NO 52
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 52
atgtatagcc ctaccagcat tctgg                                          25

<210> SEQ ID NO 53
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 53
ctggacataa gacaaggacc aaagg                                          25

<210> SEQ ID NO 54
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 54
ttggatgaca gaaaccttgt tggtc                                          25

<210> SEQ ID NO 55
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 55
atgatgacag catgtcaggg agtgg                                          25

<210> SEQ ID NO 56
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 56
gagacaagaa                                                           10

<210> SEQ ID NO 57
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 57
ccagggctct                                                           10

<210> SEQ ID NO 58
<211> LENGTH: 10
<212> TYPE: DNA
<213> ORGANISM: Artificial Sequence
<220> FEATURE:

<223> OTHER INFORMATION: Synthetic oligonucleotide

<400> SEQUENCE: 58
gtcgctgtct                                                              10

<210> SEQ ID NO 59
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 59
caaggcaagc                                                              10

<210> SEQ ID NO 60
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 60
acaacagacg g                                                            11

<210> SEQ ID NO 61
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 61
agtcacacaa                                                              10

<210> SEQ ID NO 62
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 62
agagtcacac                                                              10

<210> SEQ ID NO 63
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 63
ggatctctag                                                              10

<210> SEQ ID NO 64
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 64
ccgcttaata                                                              10

-continued

```
<210> SEQ ID NO 65
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 65
attgtttctt                                                          10

<210> SEQ ID NO 66
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 66
acatgggtat                                                          10

<210> SEQ ID NO 67
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 67
atgtcacttc                                                          10

<210> SEQ ID NO 68
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 68
aagggtacta                                                          10

<210> SEQ ID NO 69
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 69
ctatttgttc                                                          10

<210> SEQ ID NO 70
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 70
cttactattt                                                          10

<210> SEQ ID NO 71
<211> LENGTH: 11
<212> TYPE: DNA
<213> ORGANISM: Artificial Sequence
<220> FEATURE:
<223> OTHER INFORMATION: Synthetic oligonucleotide
```

```
<400> SEQUENCE: 71
ccagaatgct g                                                          11

<210> SEQ ID NO 72
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 72
ctttggtcct t                                                          11

<210> SEQ ID NO 73
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 73
ccaacaaggt                                                            10

<210> SEQ ID NO 74
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 74
actccctgac                                                            10

<210> SEQ ID NO 75
<211> LENGTH: 25
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (24)..(25)
<223> OTHER INFORMATION: DNA

<400> SEQUENCE: 75
agcaggaacu acuaguaccc uucag                                           25

<210> SEQ ID NO 76
<211> LENGTH: 27
<212> TYPE: RNA
<213> ORGANISM: Artificial Sequence
<220> FEATURE:
<223> OTHER INFORMATION: Synthetic oligonucleotide

<400> SEQUENCE: 76
cugaagggua cuaguaguuc cugcuau                                         27

<210> SEQ ID NO 77
<211> LENGTH: 25
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (24)..(25)
<223> OTHER INFORMATION: DNA
```

```
<400> SEQUENCE: 77
gcaggaacua cuaguacccu ucagg                                          25

<210> SEQ ID NO 78
<211> LENGTH: 27
<212> TYPE: RNA
<213> ORGANISM: Artificial Sequence
<220> FEATURE:
<223> OTHER INFORMATION: Synthetic oligonucleotide

<400> SEQUENCE: 78
ccugaagggu acuaguaguu ccugcua                                        27

<210> SEQ ID NO 79
<211> LENGTH: 27
<212> TYPE: RNA
<213> ORGANISM: Artificial Sequence
<220> FEATURE:
<223> OTHER INFORMATION: Synthetic oligonucleotide

<400> SEQUENCE: 79
gcaggaacua cuaguacccu ucaggaa                                        27

<210> SEQ ID NO 80
<211> LENGTH: 29
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: DNA

<400> SEQUENCE: 80
uuccugaagg guacuaguag uuccugcta                                      29

<210> SEQ ID NO 81
<211> LENGTH: 25
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (24)..(25)
<223> OTHER INFORMATION: DNA

<400> SEQUENCE: 81
caggaacuac uaguacccuu cagga                                          25

<210> SEQ ID NO 82
<211> LENGTH: 27
<212> TYPE: RNA
<213> ORGANISM: Artificial Sequence
<220> FEATURE:
<223> OTHER INFORMATION: Synthetic oligonucleotide

<400> SEQUENCE: 82
uccugaaggg uacuaguagu uccugcu                                        27

<210> SEQ ID NO 83
<211> LENGTH: 25
<212> TYPE: DNA
<213> ORGANISM: Artificial Sequence
<220> FEATURE:
```

```
<223> OTHER INFORMATION: Synthetic oligonucleotide
<220> FEATURE:
<221> NAME/KEY: misc_feature
<222> LOCATION: (24)..(25)
<223> OTHER INFORMATION: DNA

<400> SEQUENCE: 83
gcggagacag cgacgaagag cucat                                    25

<210> SEQ ID NO 84
<211> LENGTH: 27
<212> TYPE: RNA
<213> ORGANISM: Artificial Sequence
<220> FEATURE:
<223> OTHER INFORMATION: Synthetic oligonucleotide

<400> SEQUENCE: 84
uucgccucug ucgcugcuuc ucgagua                                  27

<210> SEQ ID NO 85
<211> LENGTH: 27
<212> TYPE: RNA
<213> ORGANISM: Artificial Sequence
<220> FEATURE:
<223> OTHER INFORMATION: Synthetic oligonucleotide

<400> SEQUENCE: 85
gcggagacag cgacgaagag cucauca                                  27

<210> SEQ ID NO 86
<211> LENGTH: 29
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: DNA

<400> SEQUENCE: 86
ttcgccucug ucgcugcuuc ucgaguagu                                29

<210> SEQ ID NO 87
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 87
atagcaggaa ctactagtac                                          20

<210> SEQ ID NO 88
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 88
ttgtatcgtc cttgatgatc atg                                      23

<210> SEQ ID NO 89
<211> LENGTH: 20
<212> TYPE: DNA
<213> ORGANISM: Artificial Sequence
```

```
<220> FEATURE:
<223> OTHER INFORMATION: Synthetic oligonucleotide

<400> SEQUENCE: 89
tagcaggaac tactagtacc                                              20

<210> SEQ ID NO 90
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 90
ttatcgtcct tgatgatcat gg                                           22

<210> SEQ ID NO 91
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 91
agcaggaact actagtaccc                                              20

<210> SEQ ID NO 92
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 92
ttatcgtcct tgatgatcat ggg                                          23

<210> SEQ ID NO 93
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 93
gcaggaacta ctagtaccct                                              20

<210> SEQ ID NO 94
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 94
ttcgtccttg atgatcatgg ga                                           22

<210> SEQ ID NO 95
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 95
caggaactac tagtaccctt                                              20
```

```
<210> SEQ ID NO 96
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 96
ttgtccttga tgatcatggg aa                                              22

<210> SEQ ID NO 97
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 97
aggaactact agtacccttc                                                 20

<210> SEQ ID NO 98
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 98
ttgtccttga tgatcatggg aag                                             23

<210> SEQ ID NO 99
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 99
ggaactacta gtacccttca                                                 20

<210> SEQ ID NO 100
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 100
ttccttgatg atcatgggaa gt                                              22

<210> SEQ ID NO 101
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 101
gcaggaacta ctagtac                                                    17

<210> SEQ ID NO 102
<211> LENGTH: 19
<212> TYPE: DNA
<213> ORGANISM: Artificial Sequence
<220> FEATURE:
<223> OTHER INFORMATION: Synthetic oligonucleotide
```

```
<400> SEQUENCE: 102
ttcgtccttg atgatcatg                                            19

<210> SEQ ID NO 103
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 103
gcaggaacta ctagtacc                                             18

<210> SEQ ID NO 104
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 104
ttcgtccttg atgatcatgg                                           20

<210> SEQ ID NO 105
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 105
gcaggaacta ctagtaccc                                            19

<210> SEQ ID NO 106
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 106
ttcgtccttg atgatcatgg g                                         21

<210> SEQ ID NO 107
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 107
gcaggaacta ctagtaccct t                                         21

<210> SEQ ID NO 108
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 108
ttcgtccttg atgatcatgg gaa                                       23

<210> SEQ ID NO 109
```

```
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 109
gcaggaacta ctagtaccct tca                                                23

<210> SEQ ID NO 110
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 110
ttcgtccttg atgatcatgg gaagt                                              25

<210> SEQ ID NO 111
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 111
gcaggaacta ctagtaccct tcagg                                              25

<210> SEQ ID NO 112
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 112
ttcgtccttg atgatcatgg gaagtcc                                            27

<210> SEQ ID NO 113
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 113
gcaggaacta ctagtaccct tcaggaa                                            27

<210> SEQ ID NO 114
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 114
ttcgtccttg atgatcatgg gaagtcctt                                          29

<210> SEQ ID NO 115
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 115
```

```
gcaggaacta ctagtaccct tcaggaaca                                     29

<210> SEQ ID NO 116
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 116
ttcgtccttg atgatcatgg gaagtccttg t                                  31

<210> SEQ ID NO 117
<211> LENGTH: 32
<212> TYPE: DNA
<213> ORGANISM: Human immunodeficiency virus

<400> SEQUENCE: 117
atagcaggaa ctactagtac ccttcaggaa ca                                 32

<210> SEQ ID NO 118
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 118
agggtactag tagttcctgc                                               20

<210> SEQ ID NO 119
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 119
gtactagtag ttcctgctat                                               20

<210> SEQ ID NO 120
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 120
ggtactagta gttcctgcta                                               20

<210> SEQ ID NO 121
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 121
gggtactagt agttcctgct                                               20

<210> SEQ ID NO 122
<211> LENGTH: 20
<212> TYPE: DNA
<213> ORGANISM: Artificial Sequence
<220> FEATURE:
```

<223> OTHER INFORMATION: Synthetic oligonucleotide

<400> SEQUENCE: 122
aagggtacta gtagttcctg                                                    20

<210> SEQ ID NO 123
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 123
tgaagggtac tagtagttcc                                                    20

<210> SEQ ID NO 124
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 124
gggtactagt agttcctgc                                                     19

<210> SEQ ID NO 125
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 125
aagggtacta gtagttcctg c                                                  21

<210> SEQ ID NO 126
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 126
tgaagggtac tagtagttcc tgc                                                23

<210> SEQ ID NO 127
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 127
cctgaagggt actagtagtt cctgc                                              25

<210> SEQ ID NO 128
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 128
ttcctgaagg gtactagtag ttcctgc                                            27

```
<210> SEQ ID NO 129
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 129
tgttcctgaa gggtactagt agttcctgc                                        29

<210> SEQ ID NO 130
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 130
gcaggaacta ctagtaccct actcgagaag ggtactagta gttcctgctt                 50

<210> SEQ ID NO 131
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 131
atagcaggaa ctactagtac gctcgagggt actagtagtt cctgctattt                 50

<210> SEQ ID NO 132
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 132
tagcaggaac tactagtacc gctcgagggg tactagtagt tcctgctatt                 50

<210> SEQ ID NO 133
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 133
agcaggaact actagtaccc actcgagagg gtactagtag ttcctgcttt                 50

<210> SEQ ID NO 134
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 134
caggaactac tagtaccctt gctcgaggaa gggtactagt agttcctgtt                 50

<210> SEQ ID NO 135
<211> LENGTH: 50
<212> TYPE: DNA
<213> ORGANISM: Artificial Sequence
<220> FEATURE:
<223> OTHER INFORMATION: Synthetic oligonucleotide
```

<400> SEQUENCE: 135
ggaactacta gtacccttca cctcgagctg aagggtacta gtagttcctt    50

<210> SEQ ID NO 136
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 136
gcaggaacta ctagtaccca ctcgagaggg tactagtagt tcctgctt    48

<210> SEQ ID NO 137
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 137
gcaggaacta ctagtaccct tgctcgagga aggtactag tagttcctgc tt    52

<210> SEQ ID NO 138
<211> LENGTH: 56
<212> TYPE: DNA
<213> ORGANISM: Artificial Sequence
<220> FEATURE:
<223> OTHER INFORMATION: Synthetic oligonucleotide

<400> SEQUENCE: 138
gcaggaacta ctagtaccct tcacctcgag ctgaagggta ctagtagttc ctgctt    56

<210> SEQ ID NO 139
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 139
gcaggaacta ctagtaccct tcaggtctcg agtcctgaag ggtactagta gttcctgctt    60

<210> SEQ ID NO 140
<211> LENGTH: 64
<212> TYPE: DNA
<213> ORGANISM: Artificial Sequence
<220> FEATURE:
<223> OTHER INFORMATION: Synthetic oligonucleotide

<400> SEQUENCE: 140
gcaggaacta ctagtaccct tcaggaagct cgaggttcct gaagggtact agtagttcct    60
gctt    64

<210> SEQ ID NO 141
<211> LENGTH: 68
<212> TYPE: DNA
<213> ORGANISM: Artificial Sequence
<220> FEATURE:
<223> OTHER INFORMATION: Synthetic oligonucleotide

<400> SEQUENCE: 141
gcaggaacta ctagtaccct tcaggaacat ctcgagttgt tcctgaaggg tactagtagt    60
tcctgctt    68

```
<210> SEQ ID NO 142
<211> LENGTH: 98
<212> TYPE: DNA
<213> ORGANISM: Hepatitis D virus

<400> SEQUENCE: 142
gggccagcta gtttaagggt actaggaaca gggtccacct cctcgcggtt tcctgtgggc    60
atccgttcgc ggatggctaa gggacccttt ctagctgg                           98
```